(12) United States Patent
Henschke et al.

(10) Patent No.: US 8,952,139 B2
(45) Date of Patent: Feb. 10, 2015

(54) PROCESS FOR THE PREPARATION OF β-C-ARYL GLUCOSIDES

(71) Applicant: ScinoPharm Taiwan, Ltd., Tainan (TW)

(72) Inventors: Julian Paul Henschke, Summertown (AU); Chen-Wei Lin, Chiayi (TW); Ping-Yu Wu, Tainan (TW); Chi-Nung Hsiao, New Taipei (TW); Jyh-Hsiung Liao, Hsinchu (TW); Tsung-Yu Hsiao, Kaohsiung (TW)

(73) Assignee: ScinoPharm Taiwan, Ltd, Tainan (TW)

( * ) Notice: Subject to any disclaimer, the term of this patent is extended or adjusted under 35 U.S.C. 154(b) by 184 days.

(21) Appl. No.: 13/671,461

(22) Filed: Nov. 7, 2012

(65) Prior Publication Data

US 2014/0128595 A1    May 8, 2014

Related U.S. Application Data

(60) Provisional application No. 61/556,780, filed on Nov. 7, 2011, provisional application No. 61/661,793, filed on Jun. 19, 2012.

(51) Int. Cl.
| | | |
|---|---|---|
| *C07H 1/00* | (2006.01) | |
| *C07H 7/06* | (2006.01) | |
| *C07H 3/00* | (2006.01) | |
| *C08B 37/00* | (2006.01) | |
| *C07D 309/00* | (2006.01) | |

(52) U.S. Cl.
CPC ................................... *C07D 309/00* (2013.01)
USPC .......................... 536/1.11; 536/29.2; 536/124

(58) Field of Classification Search
CPC ................................ C07D 309/00; C07H 1/00
See application file for complete search history.

(56) References Cited

U.S. PATENT DOCUMENTS 7,847,074 B2    12/2010    Eckhardt et al.

FOREIGN PATENT DOCUMENTS

WO    WO2004063209 A2    7/2004

*Primary Examiner* — Lawrence E Crane
(74) *Attorney, Agent, or Firm* — Sam L. Nguyen; Hamilton, DeSanctis & Cha, LLP

(57) ABSTRACT

The present invention provides processes (e.g., arylation reaction) for stereoselectively preparing C-arylglucosides that can be useful as synthetic building block or drugs, including SGLT2 inhibitors. A representative process of the present application includes the preparation of the compound of formula IV starting from a compound of the formula II with a metalated aryl compound, as disclosed below:

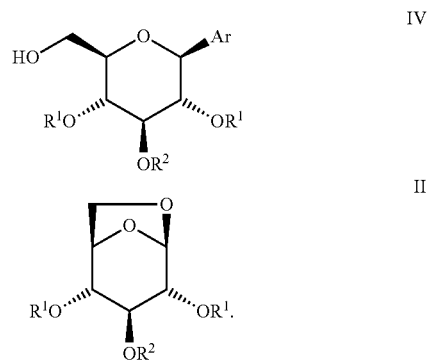

30 Claims, 4 Drawing Sheets

R²X (R² is protecting group)

IX; R$^1$= protecting group,
R$^2$ = protecting group or H

IV; R$^1$= protecting group,
R$^2$ = protecting group or H

PROCESS FOR THE PREPARATION OF β-C-ARYL GLUCOSIDES

CROSS-REFERENCES TO RELATED APPLICATIONS

This application claims the benefit of U.S. Provisional Application Ser. Nos. 61/556,780, filed Nov. 7, 2011, and 61/661,793, filed Jun. 19, 2012, the contents are each being incorporated herein by reference in their entirety.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Diabetes mellitus is a serious and chronic metabolic disease that is characterized by high blood glucose (hyperglycemia) and affects millions of people world-wide. SGLT2 is a Sodium-dependent GLucose co-Transporter protein which affects the reabsorption of glucose in the kidney. It is estimated that 90% of renal glucose reabsorption is facilitated by SGLT2. Since glucose reabsorption is mediated predominantly by SGLT2 and because high glucose levels have been identified as a cause of disease in diabetes, SGLT2 has become a drug target for type 2 diabetes therapy. Selective inhibition of SGLT2 has the potential to reduce hyperglycemia by inhibiting glucose reabsorption in the kidney with elimination of glucose by excretion in the urine (glucosuria).

A significant number of SGLT2 inhibitors are currently in clinical development and a significant portion of these are β-C-arylglucosides. Of these, dapagliflozin, developed by Bristol-Myers Squibb and AstraZeneca, is at the most advanced stage of the development with its new drug application (NDA) having been accepted for review by the Food and Drug Administration (FDA) in 2011.

In addition to dapagliflozin, there are a significant number of other β-C-arylglucoside derived drug candidates, most of which differ only in the aglycone moiety (i.e., these compounds comprise a central 1-deoxy-glucose ring moiety that is arylated at C1). It is this fact that makes them attractive targets for a novel synthetic platform technology, since a single methodology should be able to furnish a plurality of products. Among β-C-arylglucosides that possess known SGLT2 inhibition also currently in clinical development are canagliflozin, empagliflozin, and ipragliflozin.

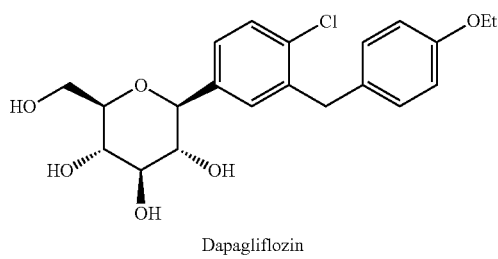

Dapagliflozin

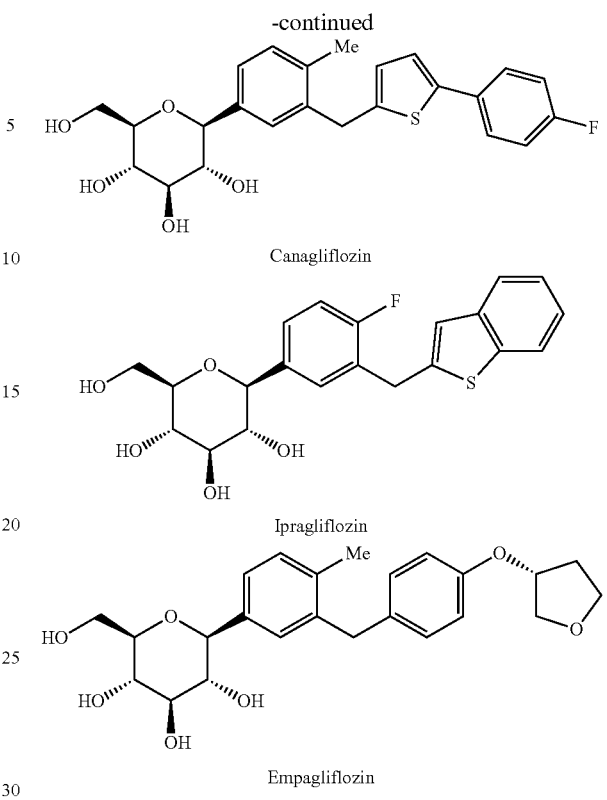

Canagliflozin

Ipragliflozin

Empagliflozin

A series of synthetic methods have been reported in the peer-reviewed and patent literature that can be used for the preparation of β-C-arylglucosides. These methods are described below and are referred herein as the gluconolactone method, the metalated glucal method, the glucal epoxide method and the glycosyl leaving group substitution method.

The gluconolactone method: In 1988 and 1989 a general method was reported to prepare C-arylglucosides from tetra-O-benzyl protected gluconolactone, which is an oxidized derivative of glucose (see *J. Org. Chem.* 1988, 53, 752-753 and *J. Org. Chem.* 1989, 54, 610-612). The method comprises: 1) addition of an aryllithium derivative to the hydroxy-protected gluconolactone to form a hemiketal (a.k.a., a lactol), and 2) reduction of the resultant hemiketal with triethylsilane in the presence of boron trifluoride etherate. Disadvantages of this classical, but very commonly applied method for β-C-arylglucoside synthesis include:

1) poor "redox economy" (see *J. Am. Chem. Soc.* 2008, 130, 17938-17954 and Anderson, N. G. *Practical Process Research & Development*, 1st Ed.; Academic Press, 2000 (ISBN-10: 0120594757); pg 38)—that is, the oxidation state of the carbon atom at C1, with respect to glucose, is oxidized in the gluconolactone and then following the arylation step is reduced to provide the requisite oxidation state of the final product.

2) due to a lack of stereospecificity, the desired β-C-arylglucoside is formed along with the undesired α-C-arylglucoside stereoisomer (this has been partially addressed by the use of hindered trialkylsilane reducing agents (see *Tetrahedron: Asymmetry* 2003, 14, 3243-3247) or by conversion of the hemiketal to a methyl ketal prior to reduction (see *J. Org. Chem.* 2007, 72, 9746-9749 and U.S. Pat. No. 7,375,213)).

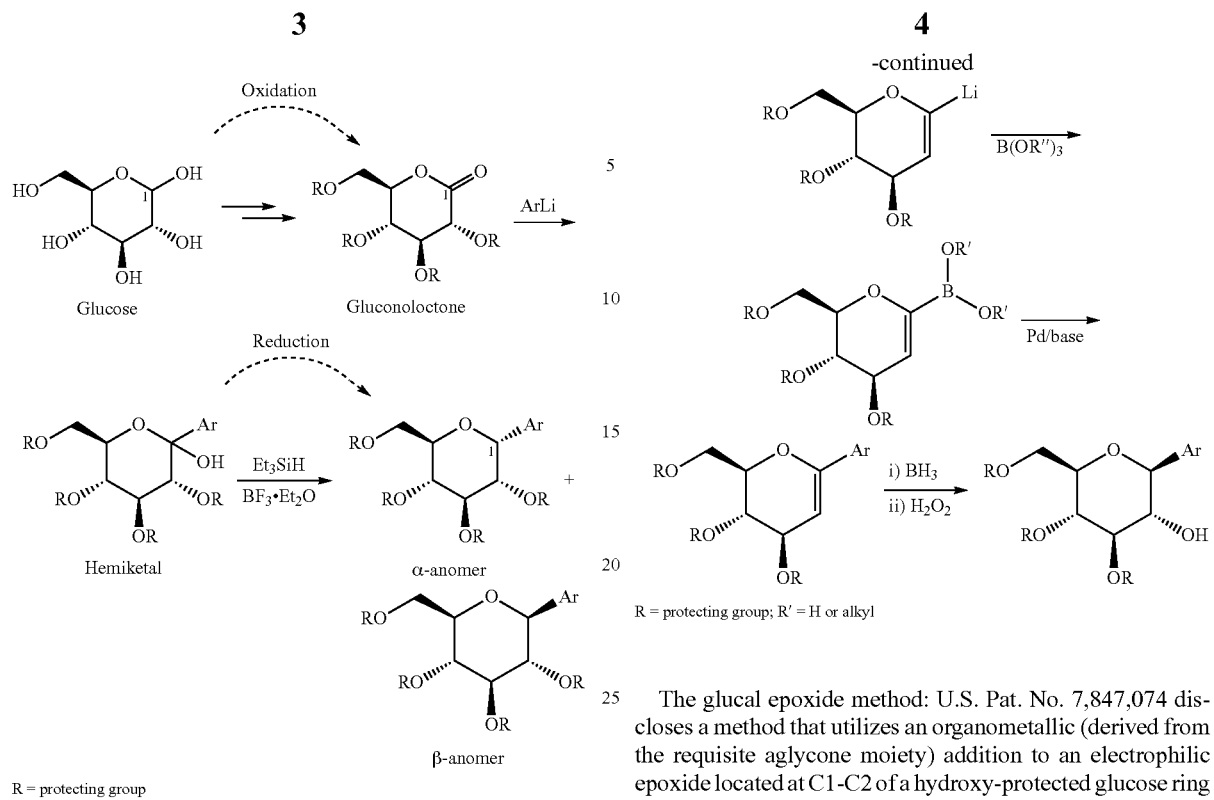

R = protecting group

The metalated glucal method: U.S. Pat. No. 7,847,074 discloses preparation of SGLT2 inhibitors that involves the coupling of a hydroxy-protected glucal that is metalated at C1 with an aryl halide in the presence of a transition metal catalyst. Following the coupling step, the requisite formal addition of water to the C-arylglucal double bond to provide the desired C-aryl glucoside is effected using i) hydroboration and oxidation, or ii) epoxidation and reduction, or iii) dihydroxylation and reduction. In each case, the metalated glucal method represents poor redox economy because oxidation and reduction reactions must be conducted to establish the requisite oxidation states of the individual C1 and C2 carbon atoms.

U.S. Pat. Appl. 2005/0233988 discloses the utilization of a Suzuki reaction between a C1-boronic acid or boronic ester substituted hydroxy-protected glucal and an aryl halide in the presence of a palladium catalyst. The resulting 1-C-arylglucal is then formally hydrated to provide the desired 1-C-arylglucoside skeleton by use of a reduction step followed by an oxidation step. The synthesis of the boronic acid and its subsequent Suzuki reaction, reduction and oxidation, together, comprise a relatively long synthetic approach to C-arylglucosides and exhibits poor redox economy. Moreover, the coupling catalyst comprises palladium which is toxic and therefore should be controlled to very low levels in the drug substance.

R = protecting group; R' = H or alkyl

The glucal epoxide method: U.S. Pat. No. 7,847,074 discloses a method that utilizes an organometallic (derived from the requisite aglycone moiety) addition to an electrophilic epoxide located at C1-C2 of a hydroxy-protected glucose ring to furnish intermediates useful for SGLT2 inhibitor synthesis. The epoxide intermediate is prepared by the oxidation of a hydroxy-protected glucal and is not particularly stable. In *Tetrahedron* 2002, 58, 1997-2009 it was taught that organometallic additions to a tri-O-benzyl protected glucal-derived epoxide can provide either the α-C-arylglucoside, mixtures of the α- and β-C-arylglucoside or the β-C-arylglucoside by selection of the appropriate counterion of the carbanionic aryl nucleophile (i.e., the organometallic reagent). For example, carbanionic aryl groups countered with copper (i.e., cuprate reagents) or zinc (i.e., organozinc reagents) ions provide the β-C-arylglucoside, magnesium ions provide the α- and β-C-arylglucosides, and aluminum (i.e., organoaluminum reagents) ions provide the α-C-arylglucoside.

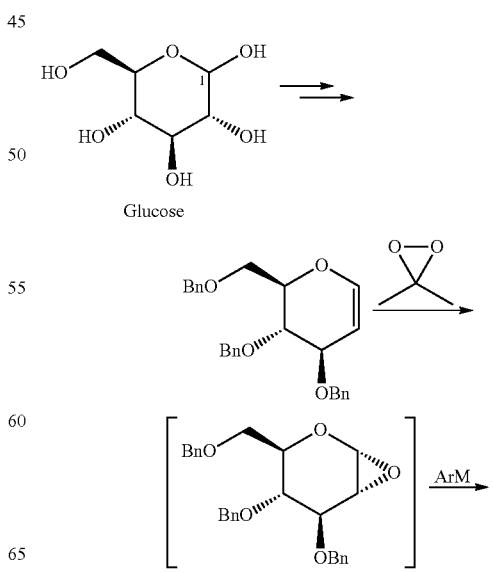

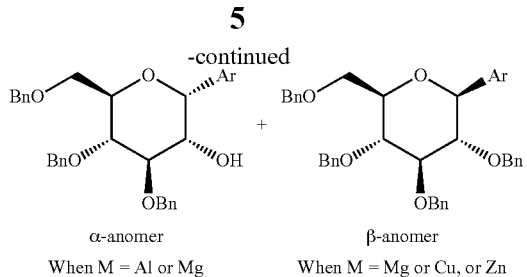

α-anomer
When M = Al or Mg

β-anomer
When M = Mg or Cu, or Zn

The glycosyl leaving group substitution method: U.S. Pat. No. 7,847,074, also disclosed a method comprising the substitution of a leaving group located at C1 of a hydroxy-protected glucosyl species, such as a glycosyl halide, with a metalated aryl compound to prepare SGLT2 inhibitors. U.S. Pat. Appl. 2011/0087017 disclosed a similar method to prepare the SGLT2 inhibitor canagliflozin and preferably diarylzinc complexes are used as nucleophiles along with tetra-O-pivaloyl protected glucosylbromide.

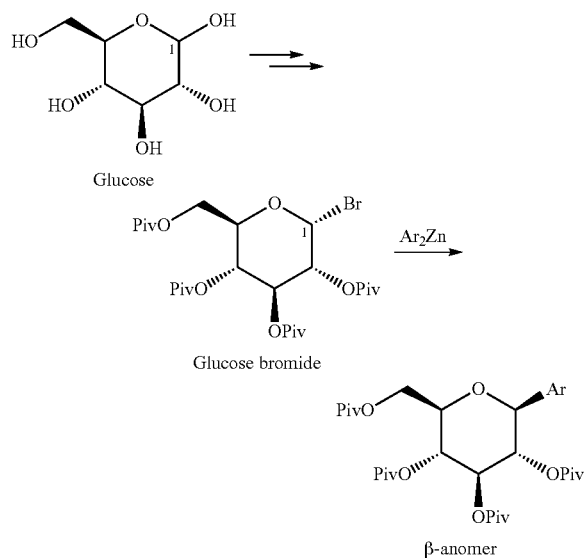

Methodology for alkynylation of 1,6-anhydroglycosides reported in *Helv. Chim. Acta*. 1995, 78, 242-264 describes the preparation of 1,4-dideoxy-1,4-diethynyl-β-D-glucopyranoses (a.k.a., glucopyranosyl acetylenes), that are useful for preparing but-1,3-diyne-1,4-diyl linked polysaccharides, by the ethynylating opening (alkynylation) of partially protected 4-deoxy-4-C-ethynyl-1,6-anhydroglucopyranoses. The synthesis of β-C-arylglucosides, such as could be useful as precursors for SLGT2 inhibitors, was not disclosed. The ethynylation reaction was reported to proceed with retention of configuration at the anomeric center and was rationalized (see *Helv. Chim. Acta* 2002, 85, 2235-2257) by the C3-hydroxyl of the 1,6-anhydroglucopyranose being deprotonated to form a C3-O-aluminium species, that coordinated with the C6-oxygen allowing delivery of the ethyne group to the β-face of the an oxycarbenium cation derivative of the glucopyranose. Three molar equivalents of the ethynylaluminium reagent was used per 1 molar equivalent of the 1,6-anhydroglucopyranose. The ethynylaluminium reagent was prepared by the reaction of equimolar (i.e., 1:1) amounts of aluminum chloride and an ethynyllithium reagent that itself was formed by the reaction of an acetylene compound with butyllithium. This retentive ethynylating opening method was also applied (see *Helv. Chim. Acta*. 1998, 81, 2157-2189) to 2,4-di-O-triethylsilyl-1,6-anhydroglucopyranose to provide 1-deoxy-1-C-ethynyl-β-D-glucopyranose. In this example, 4 molar equivalents of the ethynylaluminium reagent was used per 1 molar equivalent of the 1,6-anhydroglucopyranose. The ethynylaluminium regent was prepared by the reaction of equimolar (i.e., 1:1) amounts of aluminum chloride and an ethynyl lithium reagent that itself was formed by reaction of an acetylene compound with butyllithium.

It can be seen from the peer-reviewed and patent literature that the conventional methods that can be used to provide C-arylglucosides possess several disadvantages. These include (1) a lack of stereoselectivity during formation of the desired anomer of the C-arylglucoside, (2) poor redox economy due to oxidation and reduction reaction steps being required to change the oxidation state of C1 or of C1 and C2 of the carbohydrate moiety, (3) some relatively long synthetic routes, (4) the use of toxic metals such as palladium, and/or (5) atom uneconomic protection of four free hydroxyl groups. With regard to the issue of redox economy, superfluous oxidation and reduction reactions that are inherently required to allow introduction of the aryl group into the carbohydrate moiety of the previously mention synthetic methods and the subsequent synthetic steps to establish the required oxidation state, besides adding synthetic steps to the process, are particular undesirable for manufacturing processes because reductants can be difficult and dangerous to operate on large scales due to their flammability or ability to produce flammable hydrogen gas during the reaction or during work-up, and because oxidants are often corrosive and require specialized handling operations (see Anderson, N. G. *Practical Process Research & Development*, 1st Ed.; Academic Press, 2000 (ISBN-10: 0120594757); pg 38 for discussions on this issue).

In view of the above, there remains a need for a shorter, more efficient and stereoselective, redox economic process for the preparation of β-C-arylglucosides. A new process should be applicable to the industrial manufacture of SGLT2 inhibitors and their prodrugs, or for other medicinally useful drug candidates or drugs, or for synthetic building blocks for non-medicinal uses. This invention addresses those needs.

BRIEF SUMMARY OF THE INVENTION

The present invention provides novel and redox economic processes for preparing C-arylglucosides that can be useful as drugs, including SGLT2 inhibitors, prodrugs or synthetic building blocks (FIG. 1). The particular focus of the present processes is for, but not limited to, the manufacture of SGLT2 inhibitors. The glucoside may be in the D- or L-configuration. The present invention can also be applied to the preparation of C-arylglycosides that are derived from carbohydrates other than glucose such as mannose or galactose or that are derived from carbohydrate derivatives such as deoxycarbohydrates.

In one aspect, the present invention provides a method for the stereoselective synthesis of β-C-arylglucosides such as compounds of formula IV, VI, V and I. 2,4-Di-O-protected 1,6-anhydroglucopyranose protected compounds (i.e., the compound of formula II, where $R^2$=H and $R^1 \neq$H), are coupled with nucleophilic aryl compounds (Ar), wherein Ar is an aromatic ring, an aromatic heterocyclic ring, a biaryl ring system, a fused aromatic ring, a polyaromatic system, two or more aromatic rings bridged by methylene group, or a meta-substituted diarylmethane system to first provide a compound of formula IV (FIG. 2). In some embodiments, Ar is a meta-substituted diarylmethane (i.e., one in which the substituted benzene ring attached to the metal possesses a meta relationship between the metal and the methylene substituents) system. The 2,4-di-O-protected 1,6-anhydroglucopyranose compound (i.e., the compound of formula II) can be prepared from 1,6-anhydroglucopyranose (i.e., the compound of formula III) using methods disclosed herein (FIG. 3; $R^2$=H) or by methods known in the relevant art (see *J. Am. Chem. Soc.* 2002, 124, 10508-10518, *J. Am. Chem. Soc.* 2005, 127, 18085-18092, *Helv. Chim. Acta* 2002, 85, 2235-2257, *Synthesis* 2009, 3880-3896, *Carbohyd. Res.* 1971, 18, 357-361, *Carbohyd. Res.* 1988, 172, 311-318 and *J. Org. Chem.* 2011, 76, 10187-10197 for example). The nucleophilic aryl compounds include metalated aryl compounds (a.k.a., aromatic organometallic compounds, or metalated aryl compounds) represented by the chemical formula $[Ar_nM^1Y^1_p]M^2_q$. In the chemical formula $[Ar_nM^1Y^1_p]M^2_q$, the subscripted terms n, p and q represent numerical values that signify the stoichiometric relationship of the components of the formula and these values are a relative to metal atom $M^1$. The aryl moiety Ar can be selected for the preparation of known or novel SGLT2 inhibitors or for β-C-arylglucosides for drugs for the treatment of other medical conditions or for non-drug uses. In this aspect of the invention stereoselectivity for the desired β-C-arylglucosides can be high, with either no detectable amounts of the undesired α-C-arylglucosides being formed, or only small amounts. Features of the process are shown in FIG. 1, FIG. 2 and FIG. 4.

In a second aspect, 2,3,4-tri-O-protected 1,6-anhydroglucopyranose, protected with either the same protecting group or different protecting groups at C2-O, C3-O and C4-O, is stereoselectively arylated by contact with metalated aryl compounds $[Ar_nM^1Y^1_p]M^2_q$, preferably $Ar_3Al$, to provide the desired β-C-arylglucosides. In this aspect of the invention stereoselectivity for the desired β-C-arylglucosides can be high, with either no detectable amounts of the undesired α-C-arylglucosides being formed, or only small amounts. The tri-O-protected 1,6-anhydroglucopyranose II, where $R^1$=$R^2$ can be prepared by protection of 1,6-anhydroglucopyranose III (FIG. 3) using methods known in the relevant art. The tri-O-protected 1,6-anhydroglucopyranose II, where $R^1 \neq R^2$ can be prepared by di-O-protection of 1,6-anhydroglucopyranose III to provide a compound of formula II where $R^2$=H followed by protection of the C3-OH of the compound of formula II, where $R^2$=H to provide tri-O-protected 1,6-anhydroglucopyranose II, where $R^1 \neq R^2$.

In a third aspect, the present invention is related to a method for the synthesis of β-C-arylglucosides, without the protection of hydroxyl groups on sugar moiety, by contacting 1,6-anhydroglucopyranose III with metalated aryl compounds $[Ar_nM^1Y^1_p]M^2_q$. Thus, the compound of formula III can be directly converted to the compound of formula I without a separate protection step and without an in situ protection step. Features of the process are shown in FIG. 5.

In a fourth aspect, the present invention is related to a method for the synthesis of arylated compounds of formula VIII from 1,3-dioxolane compounds of formula VII by contact with metalated aryl compounds $[Ar_nM^1Y^1_p]M^2_q$ (FIG. 6). Preferably this aspect of the present invention is directed to, but not limited to, the synthesis of 1-aryl-3-hydroxymethyl cyclic ethers represented by the compounds formula VIII that are derived from anhydrocarbohydrates other than glucose or anhydrocarbohydrate derivatives or anhydrocarbohydrate analogues as represented by the compounds formula VII.

In a fifth aspect, the present invention is related to a method for the stereoselective synthesis of β-C-arylglucosides such as compounds of formula IV by contact of 1-O-alkyl or 1-O-aryl glucoside compounds of formula IX with metalated aryl compounds $[Ar_nM^1Y^1_p]M^2_q$ (FIG. 7).

DETAILED DESCRIPTION OF THE INVENTION

Definitions

Figure 1:
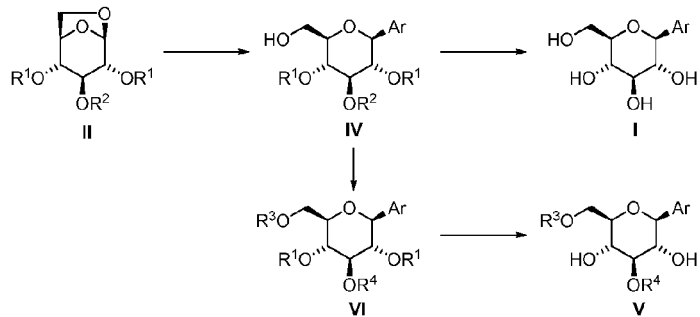
FIG. 1 provides a scheme for the stereoselective synthesis of β-C-arylglucosides according to the methods of the present invention.

As used herein, the term "glycoside" refers to a carbohydrate derivative wherein the carbohydrate is bound to a non-carbohydrate moiety (called an aglycone).

As used herein, the term "glucoside" refers to a glucose derivative wherein glucose is bound to a non-carbohydrate moiety (called an aglycone). A glucoside is a subset of the family glycoside.

As used herein, the term "C-glycoside" refers to a carbohydrate derivative, including a glucose derivative (so would be referred to as a "C-glucoside"), wherein the carbohydrate is bound to a non-carbohydrate moiety and the carbohydrate is bound to the non-carbohydrate moiety via a carbon-carbon covalent bond.

As used herein, the term "C-arylglycoside" refers to a carbohydrate derivative, including a glucose derivative (so would be referred to as a "C-arylglucoside"), wherein the carbohydrate is bound to an aromatic moiety via a carbon-carbon covalent bond.

As used herein, the prefix α- and β- refer to the configuration of the anomeric center of the C-arylglycoside. In the β-C-arylglycoside, the aryl group (i.e., the aglycone) is in the same relative positive with respect to the other chemical bonds at the anomeric center as the hydroxyl group is in β-glucose. In the α-C-arylglycoside, the aryl group (i.e., the aglycone) is in the same relative positive with respect to the other chemical bonds at the anomeric center as the hydroxyl group is in α-glucose.

As used herein, the compound of formula III is referred to as "1,6-anhydroglucopyranose", but is also known as "levoglucosan", "laevoglucosan", "1,6-anhydro-β-D-glucopyranose", "β-1,6-anhydro-glucopyranose", "1,6-anhydro-β-D-glucopyranose", 1,6-anhydro-β-D-glucose" and "(1R,2S,3S,4R,5R)-6,8-dioxabicyclo[3.2.1]octane-2,3,4-triol".

As used herein, the term "SGLT2" refers to sodium/glucose cotransporter 2, which is a sodium-dependent glucose transport protein. SGLT2 is the primary cotransporter involved in renal glucose reabsorption. As used herein, "SGLT2 inhibitor" refers to any molecule that can modulate SGLT2 activity in vitro or in vivo.

The term "alkyl," by itself or as part of another substituent, means, unless otherwise stated, a straight or branched chain hydrocarbon radical. Alkyl substituents, as well as other hydrocarbon substituents, may contain number designators indicating the number of carbon atoms in the substituent (i.e. $C_1$-$C_8$ means one to eight carbons), although such designators may be omitted. Unless otherwise specified, the alkyl groups of the present invention contain 1 to 20 carbon atoms. For example, an alkyl group can contain 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 or 5-6 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like.

As used herein, the terms "aryl", "arene" and "aromatic ring," by themselves or as part of another substituent, refer to a polyunsaturated, hydrocarbon group containing 6-18 carbon atoms which can be a single ring or a polyaromatic system (i.e. up to three rings which are fused together or linked covalently). Aryl includes biaryl, which consists of two aromatic rings directly covalently linked to one another via one ring atom of each aromatic ring. Non-limiting examples of aryl groups include phenyl, naphthyl and biphenyl.

"Heteroaryl", "heteroarene" and "aromatic heterocyclic ring" as used herein include an aromatic monocyclic or multicyclic ring system of 5 to 18 ring atoms in which at least one of the atoms in the ring system is an element other than carbon, i.e., nitrogen, oxygen or sulfur. The prefix "aza," "oxa," or "thia" before heteroaryl means that at least a nitrogen, oxygen or sulfur atom, respectively, is present as a ring atom. Representative heteroaryls include pyrazinyl, furanyl, thienyl, pyridyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazol[1,2-a]pyridine, imidazol[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

The term "arylate" as used herein means the chemical reaction of a metalated aryl compound with a carbohydrate compound to form a C-arylglycoside.

"Alkylene" as used herein includes a straight or branched bivalent hydrocarbon chain of 1 to 20 carbon atoms. Representative alkylene groups include methylene, ethylene, and the like.

"Cycloalkyl" as used herein includes a non-aromatic mono- or multicyclic ring system of 3 to 20 carbon atoms. A cycloalkyl group optionally comprises at least one sp²-hybridized carbon (e.g., a ring incorporating an endocyclic or exocyclic olefin). Representative monocyclic cycloalkyl groups include cyclopentyl, cyclohexyl, cyclohexenyl, cycloheptyl, and the like. Representative multicyclic cycloalkyl include 1-decalin, norbornyl, adamantyl, and the like.

As used herein, the term "amino acid" refers to a carboxylic acid bearing an amine functional group. Amino acids include α-amino acids, wherein the amine is bound to the carbon adjacent to the carbonyl carbon of the carboxylic acid. Examples of naturally occurring α-amino acids include L-alanine, L-cysteine, L-aspartic acid, L-glutamic acid, L-phenylalanine, L-glycine, L-histidine, L-isoleucine, L-lysine, L-leucine, L-methionine, L-asparagine, L-proline, L-arginine, L-glutamine, L-serine, L-threonine, L-valine, L-tryptophan, and L-tyrosine. Amino acids may also include the D-enantiomers of naturally occurring α-amino acids, as well as β-amino acids and other non-naturally occurring amino acids.

As used herein, "ester" refers to an alkyl, aryl, or cycloalkyl carboxylate group; i.e., a "—CO—O—R" group wherein R is alkyl, aryl, or cycloalkyl as defined herein.

As used herein, the term "protecting group" refers to a compound that renders a functional group unreactive, but is also removable so as to restore the functional group to its original state. Such protecting groups are well known to one of ordinary skill in the art and include compounds that are disclosed in Greene, T. W.; Wuts, P. G. M. *Protective Groups in Organic Synthesis*, 4th ed.; John Wiley & Sons, New York, 2006, which is incorporated herein by reference in its entirety.

As used herein, the term "metal" refers to elements of the periodic table that are metallic, including the alkali metals, alkaline earth metals, transition metals, post-transition metals, and lanthanides. Alkali metals include Li, Na, K, Rb and Cs. Alkaline earth metals include Be, Mg, Ca, Sr and Ba. Transition metals include Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg and Ac. Post-transition metals, also known as "poor metals," include Al, Ga, In, Tl, Ge, Sn, Pb, Sb, Bi and Po. Lanthanides include La, Ce, Pr, Nd, Pm, Sm, Eu, Gd, Tb, Dy, Ho, Er, Tm, Yb and Lu. Metal ions are negatively or positively charged as a result of having more or fewer electrons in the valence shell than is present for the neutral metallic element. One of skill in the art will appreciate that the metals described above can each adopt several different oxidation states, all of which are useful in the present invention. In some instances, the most stable oxidation state is formed, but other oxidation states are useful in the present invention. Metal ions useful in the present invention include, but are not limited to, Au (III), Pt (IV), Co (II), Ni (II), Fe (III), Ag (I) and Cd (II), Pd (II), Pb (II), Ru (IV), Cr (VI), Mn (VII), Zn (II), Os (IV), Ir (IV), Mo (VI), Cu (II) and Rh (III). "Metalloids" including, but not limited to, B, Si, As, and Te are also useful in the present invention. The term "non-metal" is used in the context of 'anions' and Lewis acids, and refers to for example, non-metal anions including halides, cyano, carbanions and the like. When used with reference to Lewis acids, for example, the term "non-metal" refers to B and Si (which are also classed as metalloids). A non-metal Lewis acid used herein, refers to a non-metal $M^3$ bound by at least one counterion ligand $Y^2$ (e.g., $BF_3$ and $Me_3SiOSO_2CF_3$ (i.e., TMSOTf)).

As used herein, the term "counterion" refers to a cation or anion associated with a metal or non-metal ion possessing the opposite charge. Examples of cations include, but are not limited to, $Li^+$, $Na^+$, $K^+$, and $Mg^{2+}$. Examples of anions include cyano, halide, $BF_4^-$, $PF_6^-$, and carbanion (i.e. an anion resulting from the abstraction of a proton from a hydrocarbon such as an alkane).

As used herein, the term "Lewis acid" has the meaning defined by IUPAC, i.e. "(a) molecular entity (and the corresponding chemical species) that is an electron-pair acceptor and therefore able to react with a Lewis base to form a Lewis adduct, by sharing the electron pair furnished by the Lewis base" (*IUPAC Gold Book*, International Union of Pure and Applied Chemistry, 2006). Lewis acids of the present invention contain a metal or metalloid $M^3$ bound by at least one counterion ligand $Y^2$. The Lewis acids may be boron-based, titanium-based, tin-based, zinc-based, aluminum-based and the like. Lewis acids may also be silicon-based. One of skill in the art will appreciate that other Lewis acids are useful in the methods of the present invention.

As used herein, the term "Lewis base" has the meaning defined by IUPAC, i.e. "A molecular entity (and the corresponding chemical species) able to provide a pair of electrons and thus capable of coordination to a Lewis acid, thereby producing a Lewis adduct." (*IUPAC Gold Book*, International Union of Pure and Applied Chemistry, 2006). Lewis bases of the present invention contain one or more nitrogen (N) atom(s), sulfur (S) atom(s), oxygen (O) atom(s) or phosphorous (P) atom(s). One of skill in the art will appreciate that other Lewis bases are useful in the methods of the present invention.

As used herein, the term "leaving group" refers to a functional group in a molecule that is suitable for substitution by an appropriate nucleophile. The bond between the leaving group and the molecule, whether covalent or non-covalent, is broken during the substitution so as to displace the leaving group from the molecule. Leaving groups including, but not limited to, halides, tosylates, mesylates, triflates, nosylates, and the like are useful in the methods of the present invention.

As used herein, the term "prodrug" refers to covalently bonded carriers which are capable of releasing a pharmaceutically active agent under physiological conditions. Release of the active agent can occur in vivo. Prodrugs can be prepared by techniques known to one skilled in the art. These techniques generally modify appropriate functional groups in a given compound. These modified functional groups regenerate original functional groups by routine manipulation or in vivo. Prodrug forms of the compounds of the present invention include compounds wherein a hydroxy, amino, carboxylic acid or similar group is modified.

As used herein, the term "stereoselective" refers to the preferential formation of one stereoisomer over another.

As used herein, the term "chemoselective" refers to selective reactivity of the arylating reagent towards the acetal functional group of the 1,6-anhydroglucopyranose moiety resulting in arylation of C1.

The atom numbering used herein is as in the following diagram:

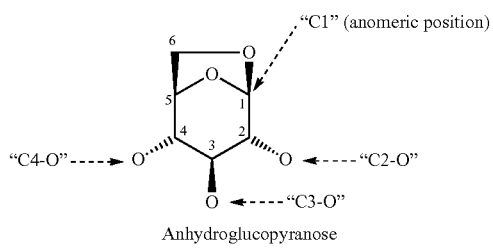

Anhydroglucopyranose

β-C-Arylglucoside

DESCRIPTION OF THE INVENTION

The present invention provides redox economic and novel processes to manufacture β-C-arylglucosides and analogues of C-arylglucosides as well as potential prodrugs of β-C-arylglucosides including prodrugs of SGLT2 inhibitors.

Figure 2:
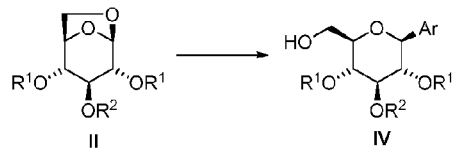
FIG. 2 provides a scheme for the stereoselective arylation of multiply-O-protected 1,6-anhydroglucopyranose.
Figure 3:
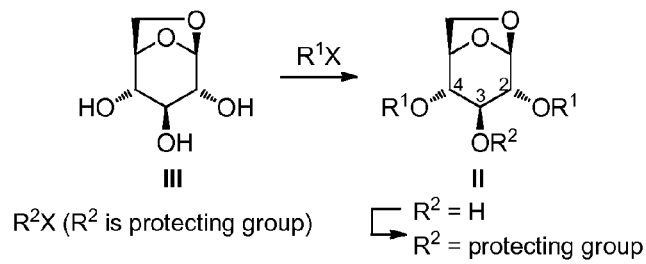
FIG. 3 provides a scheme for the preparation of 2,4-di-O-protected 1,6-anhydroglucopyranose and 2,3,4-tri-O-protected 1,6-anhydroglucopyranose derivatives.

In one aspect, the present invention provides a process for the synthesis of the compound of formula IV where $R^2$=H from a compound of formula II where $R^2$=H comprising contacting a compound of formula II with a metalated aryl compound $[Ar_n M^1 Y^1_p]M^2_q$ or contacting a metalated aryl compound $[Ar_n M^1 Y^1_p]M^2_q$ in the presence of a metallic or non-metallic Lewis acid compound $M^3 Y^2_r$. The Lewis acid can be a neutral compound, a coordination complex or a salt. This reaction step is herein referred to as the arylation reaction. FIG. 2 outlines the synthetic process of the present invention.

In FIG. 1 and FIG. 2, preferably $R^1$ is a protecting group, or each of $R^1$ together forms a chain between C2-O and C4-O (as depicted by compound X, where the atom X is B, Sn, Si, or Al or X is a Si—O—Si group), and $R^2$ comprises hydrogen. $R^1$ is selected from protecting groups that are resistance to the reaction conditions but which can be removed from the compound of formula IV or VI to provide the compound of formula I or V (FIG. 1). In some embodiments the protecting group $R^1$ might become removed without a specific deprotection step prior to the isolation of the arylation reaction product which thereby directly gives a compound of formula I. That is, the intermediate compound of formula IV is not isolated when a compound of formula XI or XII is arylated using the methods of this invention.

X

XI

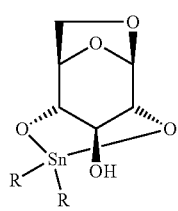

XII

In another aspect of the present invention, the invention provides a process for the synthesis of the compound of formula IV, where $R^2 \neq H$, from a compound of formula II, where $R^2 \neq H$, comprising contacting a compound of formula II, where optionally $R^2$, which is identical or different to $R^1$, is a protecting group, with a metalated aryl compound $[Ar_nM^1Y^1_p]M^2_q$ contacting a metalated aryl compound $[Ar_nM^1Y^1_p]M^2_q$ in the presence of a metallic or non-metallic Lewis acid compound $M^3Y^2_r$. $R^1$ is a protecting group, or each of $R^1$ together forms a chain between C2-O and C4-O. In this aspect, $R^1$ and $R^2$ are preferably selected from protecting groups that are resistant to the reaction conditions but which can be removed from the compound of formula IV or VI to provide the compound of formula I or V. In some embodiments the protecting group $R^1$ might become removed without a specific deprotection step prior to the isolation of the arylation reaction product.

In another aspect of the present invention, the compound of formula III can be directly converted to the compound of formula I without any of protection and deprotection steps. Given this, the desired β-C-arylglucosides can be manufactured in a very direct way.

In yet another aspect of the present invention, the compounds of formula IV are useful for making prodrugs of the formula V because the C6-O hydroxyl group of the compound of formula IV can be selectively derivatised while C2-O and C4-O are protected.

There are several methods disclosed in the literature for the preparation of 1,6-anhydroglucopyranose III which can be made from glucose by formal dehydration. For example, useful methods are described in *J. Chem. Soc. Perkin Trans.* 1, 1987, 1613-1621 and *Tetrahedron Lett.* 2009, 50, 2154-2157.

The C2-OH and C4-OH protecting groups of the invention include silicon based groups such as triethylsilyl (TES), tri-isopropylsilyl (TIPS), tert-butyldimethylsilyl (TBS or TBDMS), or tert-butyldiphenylsilyl (TBDPS), diethylisopropylsilyl (DEIPS), dimethylisopropylsilyl (IPDMS), di-tert-butylisobutylsilyl (BIBS) and the like; alkoxysilyl groups such as tert-butoxydiphenylsilyl; dialkylsilylidene (i.e., C2-O and C4-O are bridged as in compound of formula X, where X is a —Si(R$_2$)$_2$— group) such as di-tert-butylsilylidene (DTBS); disiloxanylidene (i.e., C2-O and C4-O are bridged as in compound of formula X, where X is a —(R$_2$)Si—O—Si(R$_2$)— group) such as tetraisopropyldisiloxanylidene (TIPDS). Other protecting groups can also be used including boronic esters (i.e., C2-O and C4-O are bridged by an alkyl or aryl-substituted boron atom as in the compound of formula XI, where R is alkyl, such as butyl, tert-butyl, or unsaturated alkyl (alkenes and acetylenes) or aryl, such as substituted or unsubstituted phenyl, or the same aryl group, Ar, as in the metalated arene compound of formula $[Ar_nM^1Y^1_p]M^2_q$, dibutylstannylene (i.e., C2-O and C4-O are bridged as in compound of formula X, where X is a —(R$_2$)Sn— group), allyl, benzyl, benzylidene derivatives, alkylidene derivatives, Boc, Cbz (a.k.a., Z), Fmoc, ester such as benzoyl or pivaloyl.

Methods for the synthesis of 2,4-di-O-protected 1,6-anhydroglucopyranoses of formula II where $R^2$=H can be found in the literature. For example, *Helv. Chim. Acta* 2002, 85, 2235-2257, *J. Am. Chem. Soc.* 2002, 124, 10508-10518 and *J. Am. Chem. Soc.* 2005, 127, 18085-18092 provide methods to make silyl protected derivatives of 1,6-anhydroglucopyranose, *J. Org. Chem.* 2011, 76, 10187-10197 provides a method to make a benzyl protected derivative of 1,6-anhydroglucopyranose, *Synthesis* 2009, 3880-3896 and *Carbohyd. Res.* 1971, 18, 357-361 provide a method to make the 1,6-anhydroglucopyranose 2,4-O-boronic ester protected derivative XIa and *Carbohyd. Res.* 1988, 172, 311-318 provides a method to make the 1,6-anhydroglucopyranose 2,4-O-dibutylstannylene protected derivative XIIa.

In some embodiments, silyl-based protecting groups are used, and bulky silyl-based protecting groups such as TIPS, IPDMS, TBS and TBDPS are more preferred because: 1) in some cases they can be installed selectively at C2-O and C4-O without substantial formation of isomers and/or 2,3,4-tri-O-protected co-products; 2) they are resistant to the arylation reaction conditions; 3) they can be removed following the arylation step to furnish the desired C-arylglucosides. Less bulky silyl-based protecting groups such as TMS and TES are less preferred because they are less resistant to the arylation reaction conditions and may inadvertently become partially or completely removed during the arylation reaction.

Although the compound of formula III can be arylated without protection of the hydroxyl groups, partial protection, such as protection of C2-O and C4-O, is more preferred because lesser amounts of the arylating reagent are required to effect efficient arylation.

In some embodiments, the C2-O and C4-O protecting group can be a boronic ester (i.e., a compound of formula XI). Compounds of formula XI are readily prepared from substituted boronic acids, RB(OH)$_2$ by dehydration in the presence of 1,6-anhydroglucopyranose (III). The dehydration is accomplished by contacting the boronic acid and 1,6-anhydroglucopyranose (III) in an organic solvent using a technique by which water is removed from the reaction system. The dehydration is conveniently achieved by methods known in the arts for boronic ester synthesis, including the continual removal of water from the reaction system by distillation of a water/organic solvent azeotrope (such as can be readily conducted using Dean-Stark apparatus) or by use of a drying aid such as molecular sieves or MgSO$_4$. Compounds of formula XI can also be prepared from substituted boronic acids, RB(OH)$_2$ and 1,6-anhydroglucopyranose (III) without the removal of water by conducting the esterification in a solvent such that the compounds of formula XI precipitates from the reaction mixture during the esterification reaction. Boronic esters of this invention can also be prepared by transesterification of boronic esters, RB(OR')$_2$, comprising low molecular weight alkoxy groups, OR (such as when R'=Me, Et, Pr, i-Pr; where the alcohol derivatives HOR' of the alkoxy groups are volatile compounds), with 1,6-anhydroglucopyranose (III) in an organic solvent. Boranediamines of formula RB(N(R')$_2$)$_2$ can also be used in the synthesis of compounds of formula XI. In some embodiments, boronic esters of formula XI are used wherein the R substituent is an aromatic group rather than an alkyl group, due to ease of preparation. Once the compound of formula XI has been synthesized, it can be either isolated, and optionally purified by precipitation or crystallisation or by other purification methods known in the arts, or it can be used directly in the arylation step without its purification and/or isolation.

Figure 8:
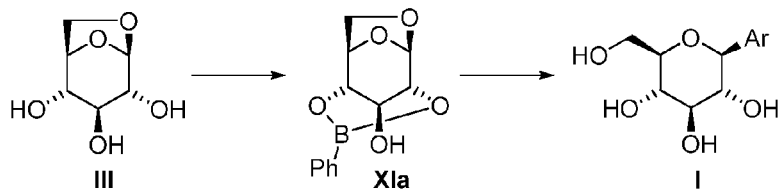
FIG. 8 provides a scheme for the preparation of β-C-arylglucosides from III through XIa without deprotection step.

The advantage of embodiments that use XI as a substrate for the arylation reaction are: i) good cost efficiency because XI is readily synthesized from cheap and boron containing reagents by heating a mixture of a suitable boronic acid or boronic acid derivative (such as boronic esters, RB(OR')$_2$, comprising low molecular weight alkoxy groups, OR' (such as when R'=Me, Et, Pr, i-Pr; wherein the parent alcohol HOR' is a volatile compound) or boranediamines of formula RB(N(R')$_2$)$_2$) and 1,6-anhydroglucopyranose (III) in a solvent with removal of water by azeotropic distillation), ii) good time and cost efficiency because the compound of formula XI does not require an aqueous reaction work-up step following its synthesis that would otherwise expend more time, iii) the compound of formula XI does not have to be purified and this saves time and cost, iv) the compound of formula XI does not have to be isolated meaning that the synthesis of XI and its subsequent arylation can be conducted in the same reactor vessel and this saves time and reduces costs, v) a specific step for deprotection of the boronic ester is not required and the compound of formula I can be directly isolated from the product mixture, without the need to isolate or specifically deprotect the compound of formula IV following the arylation reaction (FIG. 8) and this saves time and reduces costs, and vi) the boronic acid used to prepare XI can be recovered at the end of the arylation reaction and can be recycled, vii) experimental evidence indicates that the compounds of formula XI are more reactive in the arylation reaction than the compounds of formula II, and this means that compounds of formula XI can in be arylated at lower reaction temperatures than the compounds of formula II, viii) compared to syntheses of C-arylglucosides in the arts, this approach is redox economic because no oxidation or reduction step is utilized in conversion of the sugar substrate into the C-arylglucoside, ix) the boron substituent, R, in the compound of formula XI can be varied to suit manufacturing requirements, such as improved solubility, stability and cost for example, and can be an aryl, heteroaryl or alkyl group or R can be a second boron atom that forms a boron dimer as in the compound of formula XIII comprising a second molecule of a compound of formula II. Other dimeric compounds can be formed from diboronic acids in which two boron atoms are displaced by a bridging group. For example, the diboronic acid can be 1,4-aryldiboronic acid, such as 1,4-benzenediboronic acid, or diboronic acids linked by an alkyl chain, such as 1,4-butanediboronic acid. When a dimeric compound is formed from boronic acids, preferably 0.5 molar equivalent of the diboronic acid is used for every 1 molar equivalent of 1,6-anhydroglucopyranose (III). Other diboronic acid derivatives such tetrakis(dialkylamido)diboranes of formula (N(R$^1$)$_2$)$_2$BB(N(R$^1$)$_2$)$_2$, such as where R'=Me, Et, Pr, i-Pr, or reactive diboronic esters of formula (OR')$_2$BB(OR')$_2$, such as where R'=Me, Et, Pr, i-Pr, can be used in the synthesis of the dimeric compounds instead of diboronic acids.

In some embodiments, following the arylation of XI, the product mixture is cooled to ambient temperature, a protic reagent or solvent, such as an alcohol of formula R'OH, preferably methanol, is added, the solvents are evaporated and the compound of formula I is directly obtained. In this embodiment, the boron component of the boronic ester reaction input XI can be recovered from the reaction product mixture as a boronic acid, or alternatively as a boronic ester (namely of formula RB(OR')$_2$ or (OR')$_2$BB(OR')$_2$ wherein the alkoxy groups OR' originate from the alcohol, R'OH, added in the work-up step following arylation), that can be isolated, recycled and therefore used to prepare more compound of formula XI. Recycling of the boron-containing protecting group (e.g., the boronic acid RB(OH)$_2$) provides improved atom economy and can reduce impact to the environment and reduce disposal costs.

In some embodiment, the compound of formula XI is a B-aryl boronic ester compound of formula XIa, XIf, XIk, and XId. These B-aryl boronic ester compounds are readily prepared from aryl and substituted aryl boronic acids, ArB(OH)$_2$, by dehydration in the presence of 1,6-anhydroglucopyranose (III). In preferred embodiments, this esterification reaction is conveniently conducted by heating the boronic acid and 1,6-anhydroglucopyranose (III) in an organic solvent, such as toluene (PhMe) or the solvent that the subsequent arylation reaction will be conducted in, such as anisole (PhOMe), using a technique by which water is removed from the reaction system. The dehydration is conveniently achieved by methods known in the arts for boronic ester synthesis, including the continual removal of water from the reaction system by distillation of a water/organic solvent azeotrope (such as can be readily conducted using Dean-Stark apparatus) or by use of a drying aid such as molecular sieves or MgSO$_4$. The yields of the desired B-aryl boronic esters are high. When the R substituent in the B-aryl boronic esters of formula XI are simple aromatic compounds, such as phenyl, 4-fluorophenyl, 4-methoxyphenyl, 2,3,4,5,6-pentafluorophenyl, $^1$H NMR spectroscopic analysis indicates that these are produced as single isomers. In other cases, such as where XI is a diboronic acid derivative (such as 1,4-benzenediboronic acid and tetrahydroxydiboron), mixtures are formed upon dehydration of the diboronic derivative in the presence of 1,6-anhydroglucopyranose (III), as judged by $^1$H NMR spectroscopic analysis of the crude product mixture. Surprisingly, even when mixtures are formed, arylation of this boronic ester mixture using the methods of this invention still can provide the desired β-C-arylglucosides.

In other embodiments, the organic substituent R of the compound of formula XI attached to the boron is a group that does not substantially transfer to C1 of the carbohydrate substrate during the arylation reaction. That is, the organic substituent R of the compound of formula XI is selected from those substituents that exclude or minimize the formation of compounds of formula XIV where the anomeric position, C1, is substituted with the carbon-based substituent from the boron atom of the boronic ester rather than the aryl group of the arylating reagent. This is important because a known side reaction in the arylation of 2,4-O-boronic ester protected 1,6-anhydroglucopyranose compounds XI is exchange of the carbon-based substituents on the boron atom of the boronic ester and the aluminum atom of the arylating reagent. This can result in the formation of small amounts of compounds of formula XIV where the anomeric position is substituted with the carbon-based substituent from the boron atom of the boronic ester rather than the aryl group of the arylating reagent. For example, when 1 molar equivalent of the compound of formula XIf was arylated with 3 molar equivalents of Ph$_3$Al in a solvent mixture of PhOMe/di-n-butyl ether (Bu$_2$O) at 165° C. (external bath temperature) for 6 hours a mixture of the compound of formula Ia (i.e., wherein Ar in the compound of formula I is phenyl) and the compound of formula If (i.e., wherein Ar in the compound of formula I is 4-fluorophenyl) was obtained in a 98.5:1.5 mole ratio. In another example, when 1 molar equivalent of the compound of formula XId was arylated with 1 molar equivalent of Ph$_3$Al in a solvent mixture of benzonitrile (PhCN)/Bu$_2$O at 165° C. (external bath temperature) for 6 hours a mixture of the compound of formula Ia and the compound of formula Id (i.e., wherein Ar in the compound of formula I is 4-methoxyphenyl) was obtained in a 97.3:2.7 mole ratio. This side reaction can be suppressed in several ways, including i) by selection of boronic esters for which the boron substituent does not, or is less prone to, transfer such as aryl groups with suitable electronic and steric characteristics, ii) use of a boronic ester in which the carbon-based substituent from the boron atom is an identical aryl group, Ar, to the aryl group of the arylating reagent (that is, in the compound of formula XI, R=Ar, such as XIi in the synthesis of canagliflozin and such as XIj in the synthesis of dapagliflozin); iii) the use of diboronic esters of formula XIII, for which a carbon-based transferable group is absent in the reaction substrate.

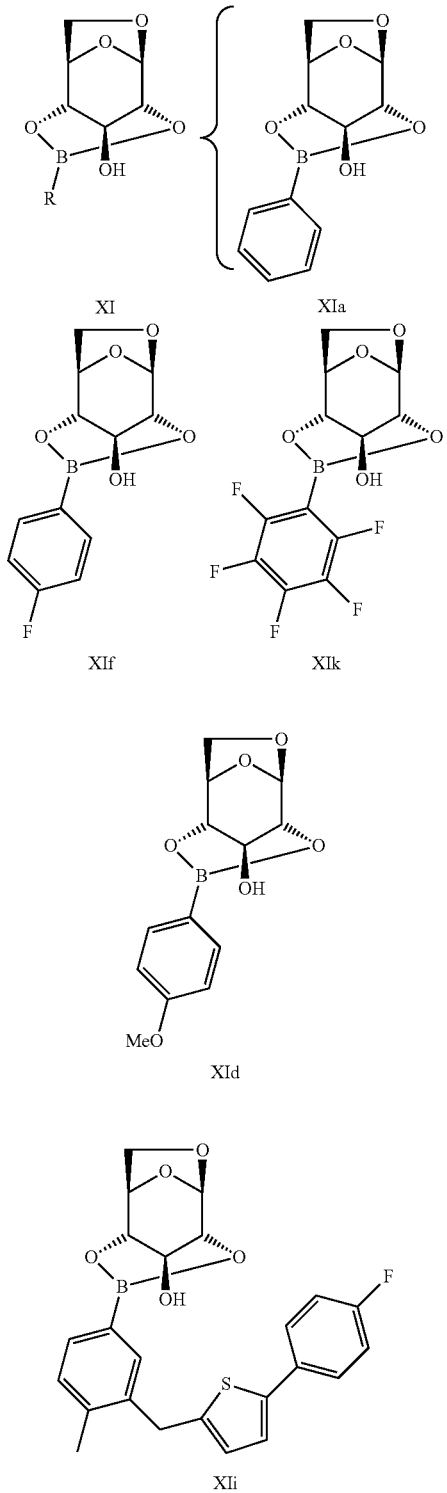

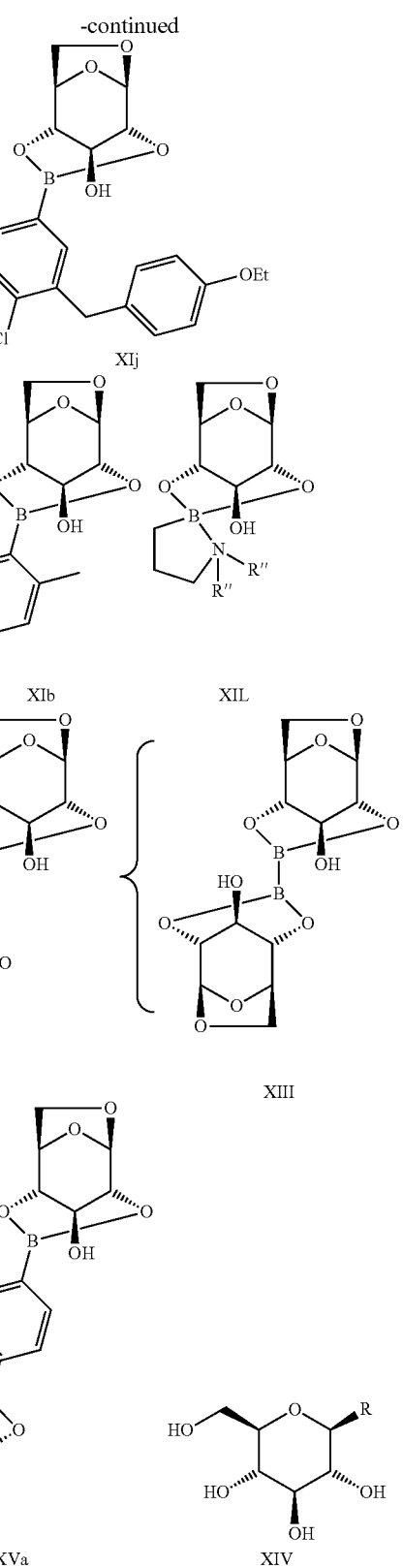

Additionally, boronic ester protection of the carbohydrate moiety is useful in the present methods as it can provide certain advantages over other protecting group systems. These advantages include i) ease of installation of the protecting group (not additional reagents such as acids or bases or activating agents are required), ii) no dedicated deprotection step is required (as stated above, the compounds of formula I are directly obtained following the arylation reaction), iii) cost savings, because boronic acids are readily and cheaply available on a commercial scale, iv) atom economy, because the boronic acids can be recycled following the arylation reaction, v) environmental, because boronic acids are generally considered to be non-toxic. In some embodiments, R of the compound of formula XI is identical to Ar of the metalated arene formula $[Ar_nM^1Y^1_p]M^2_q$.

In other embodiments, the protecting group on C2-O and C4-O can be a stannylene acetal (i.e., a compound of formula XII). Stannylene acetals of diols are known in the arts (see for example *J. Org. Chem.* 1990, 55, 5132-5139). In one embodiment, the compound of formula XII is the compound of formula XIIa and this compound is synthesized by reaction of 1,6-anhydroglucopyranose (III) with di-n-butyltin oxide (n-Bu$_2$SnO). After the compound of formula XII has been synthesized, it can be either isolated, optionally purified by precipitation, crystallisation or by other purification methods known in the arts, or can be used directly in the arylation step without purification and/or isolation. In some embodiments, following the arylation of XII, the product mixture is cooled to ambient temperature, a protic reagent or solvent, such as an alcohol, preferably methanol, or an aqueous acid solution is added, the solvents are separated or evaporated and the compound of formula I is directly obtained. In some embodiment, the compound of formula XII is the compound of formula XIIa.

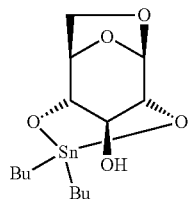

XIIa

In another embodiment, the protecting group on C2-O, C3-O, or C4-O can comprise aluminum and can be formed in situ upon reaction of 1,6-anhydroglucopyranose (III) with basic aluminum reagents (i.e., a compound of formula XVI). For example, in some embodiments, when the compound of formula III was pre-treated with aluminum reagents $R^a_2R^bAl$, wherein each of $R^a$ and $R^b$, independently, is H, substituted or unsubstituted alkyl or Ar, a compound of formula XVI might be formed although the exact molecular structure has not been determined. Preferably the aluminum reagent is a cheap chemical such as Me$_3$Al or i-Bu$_2$AlH (DIBAL). Following the pretreatment of $R^a_2R^bAl$, arylation of XVI is conducted by contact with the metalated arene formula $[Ar_nM^1Y^1_p]M^2_q$. The advantage of this embodiment is that the aluminum derivatives of compound III have improved solubility, as compared to the compound of formula III, in organic solvents that the arylation reaction can be conducted in. In another embodiment 2,4-di-O-protected compound II (where $R^1$ is a protecting group and $R^2$=H) or 2,4-di-O-protected compound XI can be reacted with basic aluminum compounds of formula $R^a_2R^bAl$ to form a compound of formula II-A or a compound of formula XI-A, respectively. These compounds can be isolated or used directly without isolation and then arylated using the methods of this invention. For example, the compound of formula XI-A, where R=Ph and $R^a$=i-Bu, was prepared at 0° C. by reaction of XIa in PhOMe with 1 molar equivalent of DIBAL in PhMe followed by arylation with Ph$_2$AlCl giving a 51% HPLC assay yield after 2.5 h at 110° C.

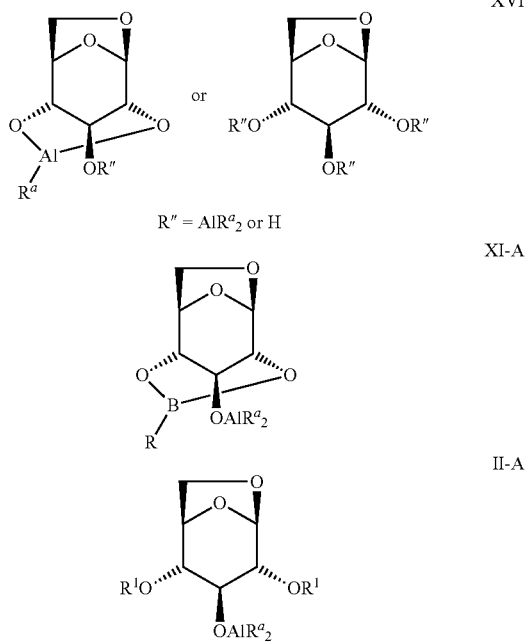

In a second aspect, the present invention provides a process for the synthesis of β-C-arylglucosides IV where $R^1$ and $R^2 \neq H$. This involves the arylation of 2,3,4-tri-O-protected 1,6-anhydroglucopyranose using $[Ar_nM^1Y^1_p]M^2_q$. In preferred embodiments of this aspect, the arylating reagent is a triarylaluminum reagent of formula Ar$_3$Al. In these methods, the arylation of 2,3,4-tri-O-protected 1,6-anhydroglucopyranose compounds of formula II, such as where $R^1=R^2$=Bn or $R^1=R^2$=TBS, with aluminum-based arylating reagents $[Ar_nAlY^1_p]M^2$, such as wherein n is <3.0 and $Y^1$ is a halide, such as chloride, provided no reaction or low yields due to a side reaction in which partial deoxygenation of the carbohydrate occurs. Furthermore, experimental examination of this aspect of the invention using triarylaluminum compounds as the arylating reagent in the presence of metal halide salts in the reaction mixture, such as MgCl$_2$, indicated that the metal halide salts had a detrimental impact on this reaction. By contrast, when arylating reagents of formula Ar$_3$Al were used in the absence of metal halide salts, good yields of the arylated products of formula IV could be obtained. Given this, in this aspect of the invention, the arylating reagent is preferably a triarylaluminum compound of formula Ar$_3$Al in the absence of other metal salts and in the absence of non-metallic halide salts. In this approach the protecting groups $R^1$ and $R^2$ of the compound of formula II can be identical or different, such as trisubstituted silyl, benzyl, methyl, boronic ester, and the like. Optionally, following initial protection of the C2-OH and C4-OH hydroxyl groups of the compound of formula III, C3-OH can subsequently be protected with a different protecting group from $R^1$ (that is, $R^1 \neq R^2$). Compounds of the formula II, where $R^1$ and $R^2 \neq H$, can be synthesized by methods described in the relevant art (see, for example, *J. Org. Chem.* 2011, 76, 10187-10197). Preferably $R^1$ and $R^2$ are selected from the group of protecting groups that are resistant to the arylation reagent and the arylation reaction conditions.

One skilled in the art will understand that different types of protecting groups (such as benzyl protecting groups compared to silyl protecting groups), or different configurations of protecting groups (2,3,4-tri-O-protected 1,6-anhydroglucopyranose compounds and 2,4-di-O-protected 1,6-anhydroglucopyranose compounds are examples of what is meant by different configurations of protecting groups), on the hydroxyl groups of the carbohydrate ring might influence the rate and or efficiency of the arylation reaction. For some protecting groups, the arylation reaction of 2,3,4-tri-O-protected 1,6-anhydroglucopyranose of the compound of formula II, where $R^1$ and $R^2 \neq H$, proceeds more slowly and provides lower chemical yields of the arylated products under identical or comparable reaction conditions than 2,4-di-O-protected 1,6-anhydroglucopyranose of the compound of formula II, where $R^2=H$ and $R^1$ is the same in both the di-O-protected and tri-O-protected systems. For example, arylation of the compound of formula II, where $R^1=R^2=TBS$, with 2 molar equivalents of the arylating reagent $Ph_3Al$ in $PhOMe/n-Bu_2O$ mixture at 150° C. (external bath temperature) gave a lower assay yield (15%) and lower isolated chemical yield (12%) of phenylated product of formula IVa'''' (the compound IV where Ar=Ph) than the similar arylation reaction performed on the compound of formula II, where $R^1=TBS$ and $R^2=H$ which gave about 68% isolated yield. But by further contrast, in another example of the arylation of a 2,3,4-tri-O-protected 1,6-anhydroglucopyranose compound, the arylation using about molar equivalents of $Ph_3Al$ in $PhOMe/n-Bu_2O$ mixture at 150° C. (external bath temperature) of the compound of formula II, where $R^1=R^2=Bn$, gave a 64% assay yield and 62% isolated chemical yield.

Therefore, some protecting groups and configurations of protecting groups are more preferred than others: in this invention, silyl protecting groups (such as TBDPS and TBS) and boronic ester protecting groups (such as B-aryl boronic esters) are most preferred for 2,4-di-O-protected 1,6-anhydroglucopyranose compounds, and benzyl groups and benzyl group derivatives are more preferred than silyl groups for 2,3,4-tri-O-protected 1,6-anhydroglucopyranose compounds. On grounds of atom economy, 2,4-di-O-protected 1,6-anhydroglucopyranose compounds are more preferred than 2,3,4-tri-O-protected 1,6-anhydroglucopyranose compounds.

In a third aspect, the present invention provides a straightforward and efficient process to prepare the compound of formula I comprising contacting a compound of formula III with a metalated aryl compound of formula $[Ar_nM^1Y^1_p]M^2_q$ optionally in the presence of metallic or non-metallic Lewis acid $M^3Y^2_r$ under conditions sufficient to form said compound of formula I. The key characteristic of this straightforward process is that when the compound of formula III is optionally pre-treated with inexpensive bases such as aluminum reagents $R^a_2R^bAl$, wherein each of $R^a$ and $R^b$, independently, is H, substituted or unsubstituted alkyl or Ar, meaning that less metalated aryl compound $[Ar_nM^1Y^1_p]M^2_q$ is required. Examples of aluminum reagents $R^a_2R^bAl$ include but are not limited to $Me_3Al$, diisobutylaluminium hydride (i-$Bu_2AlH$; DIBAL) and $Ph_3Al$. Not being bound by theory, the function of pretreatment of the compound of formula III might be to deprotonate between one to three of the three free hydroxyl groups at C2-O, C3-O and C4-O of compound III forming a carbohydrate-aluminum complex such as the compound of formula XVI before reaction with the metalated aryl compound $[Ar_nM^1Y^1_p]M^2_q$. Optionally, a Lewis acid $M^3Y^2_r$ can be added to improve the arylation reaction rate/and or the yield.

In some embodiments, the compound of formula I is provided by: i) pre-treating the compound of formula III with $Me_3Al$ in MeCN as a solvent or with DIBAL in PhMe as a solvent, and then contacting the resulting mixture with $Ar_3Al$, where Ar is an aryl group optionally followed by addition of $AlCl_3$ as Lewis acid, or ii) the compound of formula III directly reacted with excess amount of the metalated aryl compound $[Ar_nM^1Y^1_p]M^2_q$ in an appropriate solvent without the presence of an additional Lewis acid. The arylation reaction of compound of formula III is carried out at above 80° C., preferably at 110-180° C., most preferably at about 130° C. This arylation method, that does not utilise protection of the hydroxyl groups, is very economical in the number of synthetic steps. In processes where the cost of the arylating reagent is not prohibitive, this can be a cost and time competitive synthetic method for the preparation of β-C-arylglucosides because protection and deprotection steps are not required. For example, when the compound of formula III was reacted with excess amount of $Ph_3Al$ in 1,4-dioxane (dioxane) under reflux temperature for 6 days a 93% HPLC assay yield was achieved, and a 71% isolated yield of compound of formula I, where Ar=Ph, was obtained following column chromatographic purification. The arylation reaction was stereoselective for the desired β-C-arylglucoside, with the undesired α-anomer being formed in only about 2%.

The key synthetic step of the present invention is a redox economic and stereoselective arylation reaction of: i) 2,4-di-O-protected 1,6-anhydroglucopyranose (i.e., the conversion of a compound of formula II, where $R^1=H$ and $R^2=H$, to a compound of formula IV including the conversion of a compound of formula XI directly to a compound of formula I), of ii) 2,3,4-tri-O-protected 1,6-anhydroglucopyranose (i.e., the conversion of a compound of formula II, where $R^1$ and $R^2=H$, to a compound of formula IV), and of iii) unprotected 1,6-anhydroglucopyranose (i.e., the direct conversion of a compound of formula III to a compound of formula I). The arylation reaction can be accomplished using metalated aryl compounds represented by the formula $[Ar_nM^1Y^1_p]M^2_q$ or metalated aryl compounds $[Ar_nM^1Y^1_p]M^2_q$ in the presence of metallic or non-metallic Lewis acids represented by the formula $M^3Y^2_r$. The Lewis acid can be a neutral compound, a coordination complex or a salt. It has been discovered that in some reaction systems the arylation of protected and unprotected 1,6-anhydroglucopyranose using $[Ar_nM^1Y^1_p]M^2_q$ or $[Ar_nM^1Y^1_p]M^2_q$ in combination with Lewis acids $M^3Y^2_r$ can be more efficient when certain Lewis bases are used as additives or as solvents. The Lewis bases include N, S, O and P-containing compounds, such as nitriles (including substituted or unsubstituted benzonitriles) and ethers.

Therefore, in some embodiments Lewis bases can be used as additives the arylation reaction in stoichiometric or substoichiometric amounts with respect to compounds of the formula II or compounds of the formula III. In some instances, Lewis bases have proven useful as solvents. For example, the ether solvent PhOMe (anisole) and the nitrile compound PhCN (benzonitrile) improve the efficiency of the arylation reaction and can be used as additives, or also as solvents, or as co-solvents. Other nitriles, such as 4-methoxybenzonitrile, can be used as an additives even when an ether solvent such as anisole is used. Therefore, in some embodiments, the Lewis base can be used as an additive, as a co-solvent or as a solvent.

In some embodiments the C3-O group of the arylation substrate exists as a free hydroxyl group (i.e., C3-OH where $R^2$ is H in the compound of formula II or XI) that is optionally deprotonated by either of two modes: i) during the arylation reaction upon contact with the metalated aryl compound $[Ar_nM^1Y^1_p]M^2_q$, or ii) separately deprotonated before contact with the metalated aryl compound $[Ar_nM^1Y^1_p]M^2_q$ by contacting the compound of formula II or XI where $R^2$ is H with a base. When a base is used to deprotonate the C3-OH prior to the arylation reaction, preferably a strong base, such as NaH, LiH, KH, $MgH_2$, LHMDS, NaHMDS, n-BuLi, s-BuLi, t-BuLi, PhLi, i-$Bu_2AlH$ (DIBAL), PhMgBr (phenylmagnesium bromide), i-PrMgCl or LDA is used. In some embodiments, it is more preferable to deprotonate the compound of formula II or XI, where $R^2$=H, with a lithium base such as n-BuLi or an aluminum base such as i-$Bu_2AlH$ than to deprotonate with a magnesium halide base such as PhMgBr because higher yields of the arylated product can be obtained. Without being bound by theory, it is suspected that this is because magnesium halide salts have a negative impact on the arylation reaction and promote side reaction(s).

Therefore, in some embodiments it is preferred that 1 molar equivalent of the compound of formula II or XI, where $R^2$=H, is deprotonated with a 1 molar equivalent of the aluminum base i-$Bu_2AlH$ or the lithium base n-BuLi at below ambient temperature or at ambient temperature in the arylation reaction solvent, preferably PhOMe, prior to contact with the arylating reagent.

In other embodiments where the arylating reagent is used to deprotonate the C3-OH of the compound of formula II, where $R^2$=H, the aryl subscript n in the formula $[Ar_nM^1Y^1_p]M^2_q$ is preferably increased by an amount to account for the loss of some aryl moiety from the arylating reagent due to its protonation to form ArH.

With respect to cost considerations on manufacturing scales, of the two modes of deprotonation of the compound of formula II or XI, where $R^2$=H, the prior deprotonation with a cheap and readily available base such as i-$Bu_2AlH$ and n-BuLi are more preferred. In other embodiments, $R^2$ of the compound of formula II or XI, where $R^1$ and $R^2 \ne$H, and $R^1 \ne R^2$, might be a temporary protecting group that is removed during the arylation reaction to provide a free C3-alkoxy group. $R^2$ groups that might be removed during the arylation reaction can react with the arylating reagent and therefore is deprotected during the reaction, comprise protecting groups such as esters (for example acetyl) or sensitive silyl ethers (for example trimethylsilyl).

The metalated aryl compound $[Ar_nM^1Y^1_p]M^2_q$ comprises one (where n=1) or more (where n>1) aryl groups Ar, wherein Ar includes phenyl derivatives, aromatic heterocyclic compounds, biaryl compounds, fused aromatic compounds, poly aromatic compounds, methylene bridge aromatic compounds, preferably meta-substituted diarylmethane group. The molecular structure of the aryl group can also have a significant influence on the rate and also on the chemical yield of the arylation reaction. For some systems, the nature of the metalated aryl compound $[Ar_nM^1Y^1_p]M^2_q$, reaction conditions and mode of operation can all be modified, fine-tuned and optimized to provide the best chemical yields.

In one group of embodiments, Ar is selected from the group comprising:

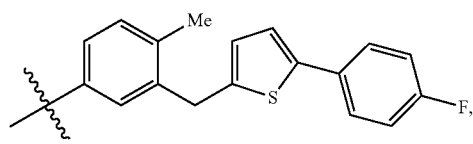

-continued

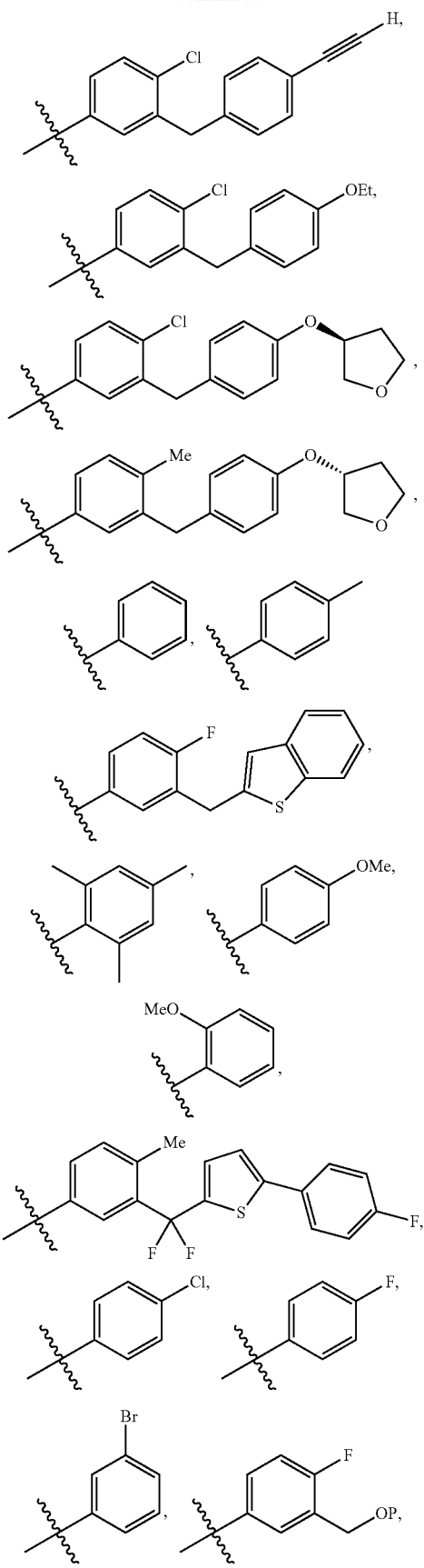

-continued

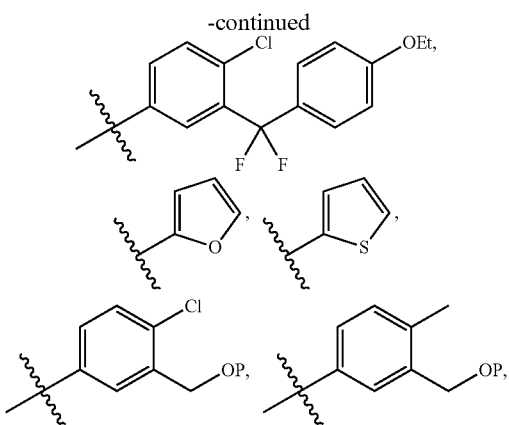

wherein P is a suitable protecting group selected from silyl groups such as TBS, TIPS, TBDPS, alkyl groups such as methyl, ethyl, isopropyl, tert-butyl and benzyl, and substituted benzyl groups such as 4-methoxybenzyl.

In the formula $[Ar_nM^1Y^1_p]M^2_q$, that is used herein to represent the empirical composition of the arylating reagent, the subscripted terms n, p and q represent the molar equivalents of the aryl moiety Ar, the molar equivalents of the anion $Y^1$ and the molar equivalents of the counter cation $M^2$, respectively, with respect to one molar equivalent of the metal $M^1$. The formula $[Ar_nM^1Y^1_p]M^2_q$ represent the empirical formula, based on the components that it was synthesized from, of the arylating reagent rather than necessarily representing the molecular formula. Those skilled in the art will be aware that for metal species possessing mixed ligands, the metal ligands can exchange in solution meaning that mixtures of related metal species can co-exist. Furthermore, those skilled in the art will be aware that some metal species can exist under certain conditions as either monomers or non-monomeric entities such as dimers, oligomers or polymers. Furthermore, those skilled in the art will recognize that on the molecular level, the anion $Y^1$ might be associated with either $M^1$ or $M^2$ or with both cations $M^1$ and $M^2$. Therefore, the formula $[Ar_nM^1Y^1_p]M^2_q$ is only provided to serve as representation of the arylating reagent and the exact species or mixture of species that bring about the arylation reaction might differ in composition with respect to this formula.

Variation of the chemical reactivity and chemoselectivity of the arylating reagent can be accessed by changing the relative molar quantities of the metal $M^1$'s ligands Ar and $Y^1$ also other associated ions $M^2$. In particular, increasing or decreasing the mole ratio of Ar to $M^1$ whilst at the same time decreasing or increasing the mole ratio of $Y^1$ to $M^1$ can have a large influence on the chemical reactivity and chemoselectivity of the arylating reagent $[Ar_nM^1Y^1_p]M^2_q$. Generally, decreasing the mole ratio of Ar to $M^1$ whilst increasing the mole ratio of $Y^1$ to $M^1$ increases the reactivity of the arylating reagent, but can also decrease its selectivity by promoting side reactions and also produces a less stable arylating reagent. On the other hand, increasing the mole ratio of Ar to $M^1$ whilst decreasing the mole ratio of $Y^1$ to $M^1$ decreases the reactivity of the arylating reagent, making the reaction slow (and requires more of the aryl group that can lead to raw material cost increases) but improves the reaction chemoselectivity. Changing the ions $M^2$ associated with the $M^1$ complex can also have an influence.

With all factors considered, and depending on the final product desired, a compromise in the reactivity and chemoselectivity of the arylating reagent may be required. Given that the mole ratio of Ar to $M^1$ and the mole ratio of $Y^1$ to $M^1$ was determined to be important for reactivity and chemoselectivity of the arylating reagent when $M^1$=Al, it is optimal when all organometallic reagents and aluminum(III) salt solutions, such as $AlCl_3$ in tetrahydrofuran (THF), are titrated prior to use to ensure that accurate amounts can be combined during preparation of the arylating reagent. To avoid or minimize changes in concentration or selected reagents when stored for significant periods of time between use, the Grignard reagents and $AlCl_3$ in THF are typically stored at about $-20°$ C. and then warmed to ambient temperature prior to use.

$M^1$ is a metal with an oxidation state (a.k.a., valence) o, where o=n+p−q. Given that the formula represents an empirical relationship of the constituents Ar, $M^1$, $Y^1$ and $M^2$ and does not necessarily represent a discrete chemical entity, the subscripts n, p and q can be integers or can be non-integer numbers. Generally, the subscript n is a number from 1 to 6, inclusive. The subscript p is also a number from 0 to 6 inclusive. And the subscript q is a number from 0 to 4 inclusive. For example, when $M^1$ is aluminum (Al), which has an oxidation state of +3 (i.e., o=3), n can be 2.5 while p is 0.5 such as represented by the formula $[Ar_{2.5}AlY^1_{0.5}]M^2_q$ such as in the arylating reagent represented by the formula $Ph_{2.5}AlCl_{0.5}$ that could be prepared from the transmetalation (salt metathesis) of 2 moles of $AlCl_3$ with 5 moles of PhMgCl.

Those skilled in the art will understand that the compound $Ph_{2.5}AlCl_{0.5}$ cannot exist as an isolated chemical entity. Instead the formula means that for every mole of aluminum ions, there are 2.5 moles of phenyl anion and 0.5 moles of chloride, which exists as a statistical mixture of species including $Ph_3Al$ and $Ph_2AlCl_1$ in various amounts, and potentially other species such as $PhAlCl_2$.

Figure 9:
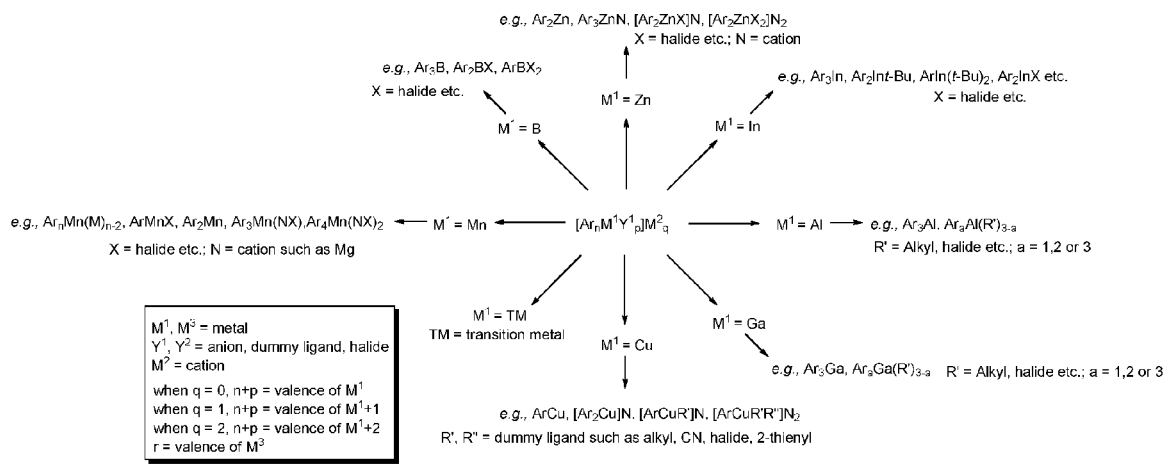
FIG. 9 shows some of the metalated aryl compounds $[Ar_nM^1Y^1_p]M^2_q$ that are useful in the methods of the present invention.

$M^1$ includes transition metals, poor metals, alkaline earth metals and lanthanides, particularly including Al, Ga, Zn, Cu, Mn, Mg, In, Li and metalloids such as B (see FIG. 9 below).

$Y^1$ is one or more anion(s) which includes but is not limited to halides, sulfonates, cyanide, alkoxides (including the C3-O hydroxyl group deprotonated form of compound of formula II or XI), phenolates, carboxylates or carbanions (which are non-participating and non-reacting ligands or only participate in the reaction by acting as a base for the deprotonation of the C3-OH group). Where there is more than one type of anion $Y^1$, then the subscript p is the total molar equivalents of anions with respect to 1 molar equivalent of $M^1$.

$M^2$ is one or more cation(s) including but is not limited to Li, Na, K and Mg. Where there is more than one cationic counterion $M^2$, then the subscript q is the total number of cations. $Y^1$ and $M^2$ are optional and when $M^2$ is absent $[Ar_nM^1Y^1_p]M^2_q$ is more simply represented by the formula $Ar_nM^1Y^1_p$, and when both $Y^1$ and $M^2$ are absent $[Ar_nM^1Y^1_p]M^2_q$ is more simply represented by the formula $Ar_nM^1$ (for example, such as in the arylating reagent $Ph_3Al$).

It is known in the relevant art (see for example *Tetrahedron: Asymmetry* 2009, 20, 1407-1412) that Lewis acid arylating reagents such as arylaluminum reagents form stable Lewis acid-Lewis base adducts with Lewis bases such as ethers. Therefore, the arylating reagent of the formula $[Ar_nM^1Y^1_p]M^2_q$ might be a used in the form of a Lewis acid-Lewis base complex, such as formed with Lewis basic organic compounds such as ethers (for example, diethyl ether ($Et_2O$), $Bu_2O$, PhOMe, or THF), however, although the existence or non-existence and nature of these complexes might influence the reactivity and chemoselectivity of the arylating reagent it is not the intention herein to specify these complexes in the formula of the arylating reagent. FIG. 9 shows some of the metalated aryl compounds $[Ar_nM^1Y^1_p]M^2_q$ useful in this invention.

In some instances $[Ar_nM^1Y^1_p]M^2_q$ can be a commercially available reagent (such as $Ph_3Al$ for example) or synthesized prior to the arylation reaction by mixing of the requisite staring materials. For example, $Ph_3Al$ can be purchased from commercial sources or can be synthesized prior to conducting the arylation reaction by the transmetalation of 1 molar equivalent of $AlCl_3$ or $AlBr_3$ and 3 molar equivalents of $PhMgBr$, $PhMgCl$ or PhLi, or other suitable organometallic reagents.

The purity of the arylating reagent, as well as the starting materials from which the arylating reagent is synthesized can influence the reactivity and chemoselectivity of the arylating reagent. Without being bound by theory, this appears to be because the transmetalation salt by-products such as LiCl, LiBr, $MgCl_2$, $MgBr_2$, if not removed prior to arylation, interact with the arylating reagent and alter its chemical nature. The arylating reagent can be used in a non-purified or in a purified form (such as obtained by precipitation, crystallization or extraction into a solvent that cannot substantially dissolve the transmetalation by-product salts) or formed in situ such as by the reaction of $M^1Y^1_p$ (where p=o) with $Ar_n.M^2$. In some embodiments when $M^1$ is Al, and the Ar anion originates from aryl lithium compounds (ArLi) or aryl Grignard reagents, it is preferred that the arylating reagent is used in its purified form as salt byproducts such as, LiCl and $MgCl_2$, from its synthesis can interfere in the arylation reaction. The synthesis and purification of trisubstituted organoaluminum species (organoalanes) has been described in the literature (for example, see the supporting information section of *J. Am. Chem. Soc.* 2006, 128, 14808-14809 for six triarylaluminum ($Ar_3Al$) complexes and see *Tetrahedron: Asymmetry* 2009, 20, 1407-1412 for several triphenylaluminum ($Ph_3Al$) complexes). The triarylaluminum compound $Ar_3Al$ may exist as dimers, $Ar_6Al_2$, but will be represented herein by the empirical formula $Ar_3Al$ for convenience. One way in which purification of the arylating reagent can be achieved is by mixing the crude arylating reagent, formed by the metathesis of $AlCl_3$ and $PhMgBr$, with $Bu_2O$ causing the unwanted magnesium halide salts to precipitate. The $Bu_2O$ solution of $Ph_3Al$ is then separated from the salts by filtration and can be used directly in the arylation reaction. $Ar_n.M^2$ includes but is not limited to aryl lithium compounds and aryl Grignard reagents.

Examples of $[Ar_nM^1Y^1_p]M^2_q$ include $Ar_3Al$, $Ar_{2.5}AlX_{0.5}$, $Ar_4AlLi$, $Ar_4AlMgX$, where X is a halide (such as chloride and bromide), phenoxide or substituted phenoxide, or sulfonate, where Ar is an aryl group as presented above.

Some metalated aryl compound of formula $[Ar_nM^1Y^1_p]M^2$ can be conveniently prepared by the transmetalation of metal salts ($M^1Y^1_o$; where the subscript o is both the oxidation number of $M^1$ and is also the number of counter anions $Y^1$ with respect to $M^1$) with aryl lithiums (ArLi), aryl Grignard reagents (ArMgX, where X is a halide) or arylaluminum reagents ($Ar_3Al$) which can be purchased in some cases or prepared using methods known in the relevant art. For example, $Ph_3Al$ can be prepared by the reaction of 1 mole of $AlCl_3$ with 3 moles of PhLi or $PhMgCl$ or $PhMgBr$.

Given that lithium and magnesium salt by-products can interfere with the arylation reaction it is more preferred that metalated aryl compound of formula $Ar_nM^1Y^1_p$, where $M^1$ is Al, are directly prepared by the transmetalation of $Ar_3Al$, that is free of undesired salts such as magnesium halides, and $AlY^1_3$. For example, the arylating reagent represented by the formula $Ph_2AlCl$ can be very conveniently prepared by the mixing of 1 molar equivalent of $AlCl_3$ in a suitable solvent and 2 molar equivalents of $Ph_3Al$ in a suitable solvent at ambient temperature for less than one hour, about one hour or for several hours prior to the arylation reaction. In the embodiment where arylating reagents represented by the formula $Ar_nAlY^1_p$ are directly prepared by the transmetalation of $Ar_3Al$ and $AlY^1_3$, subscripted values n and p are varied by changing the mole ratio of the $Ar_3Al$ and $AlY^1_3$ reagents. $Y^1$ can be selected from the group halide such as chloride and bromide, sulfonate such as methanesulfonate and trifluoromethanesulfonate (also known as triflate or OTf), phenolate including phenolate derivatives such as 2,6-dihalophenolate and 2,3,4,5,6-pentahalophenolates, carboxylates, such as trifluoroacetate, carbanions, such as aryl or alkyl.

Alternatively when $M^1$=Al, aryl sesquihalides of formula $ArAl_{2/3}Y^1$, which represents a mixture of $Ar_2AlY^1$ and $ArAlY^1_2$, can be prepared by oxidative addition of aluminum metal into aryl halides of formula $ArY^1$ (see for example *Ann. Chem.* 1962, 654, 23 and *Nature Chemistry* 2010, 2, 313-318). These aryl sesquihalides can be useful as arylating reagents in this invention, or can be modified by further reaction with aryl organometallic reagents $Ar_n.M^2$, such as Grignard reagents and aryl lithium compounds.

The arylation reaction is then conveniently conducted by adding the compound of formula II or XI to the aluminum mixture, optionally evaporating any low boiling solvents, and then heating the mixture at an elevated temperature. In preferred embodiments the arylating reagent is an arylaluminum compound. In even more preferred embodiments the arylating reagent is an arylchloroaluminum compound represented by the formula $Ar_nAlCl_p$.

Arylating reagents can also be prepared by the reaction of a limited, a stoichiometric amount or an excess amount of $[Ar_nM^1Y^1_p]M^2$ with the compound of formula II or XI where either of both of $R^1$ and $R^2$ are hydrogen to give metal complexes of the metal $M^1$ and 1,6-anhydroglucopyranose. These metal alkoxy complexes can be optionally isolated or used directly in the arylation reaction.

In some embodiments where $M^1$ is aluminum (Al), arylating reagents of formula $[Ar_nAlY^1_p]M^2$ can be conventionally prepared by the transmetalation of $Ar_3Al$ with $AlY^1_3$, where $Y^1$ is a halide (such as chloride and bromide), phenolate, alkoxide, carboxylate or sulfonate.

Additionally, different mole ratios of $Ar_3Al$ and $AlY^1_3$ provide arylating reagents with significantly different reactivities and chemoselectivities. In one example, arylation of the compound of formula II, where $R^1$=TBDPS and $R^2$=H, using an arylating reagent, prepared from 1.0 molar equivalent of $AlCl_3$ (i.e., $Y^1$=Cl) and 3 molar equivalent of $Ph_3Al$, provided the compound of formula IV, where $R^1$=TBDPS and $R^2$=H, in 80% yield by heating at 130° C. (external bath temperature) in $PhOMe/Bu_2O$ as the solvent for about 3 hours. In this example, the arylating reagent also fulfilled the role as base to deprotonate C3-OH. By contrast, the use of a premix of 1.7 molar equivalents of $Ph_3Al$ and 0.3 molar equivalents of $AlCl_3$ in the arylation of the compound of formula IV, where $R^1$=TBDPS and $R^2$=H, at 130° C. (external bath temperature) in $PhOMe/Bu_2O$ as the solvent required 8 hours to reach a yield of 73%. By further contrast, the use of 2.0 molar equivalents of $Ph_3Al$ in the absence of $AlCl_3$ in the arylation of the compound of formula IV, where $R^1$=TBDPS and $R^2$=H, at 130° C. (external bath temperature) in $PhOMe/Bu_2O$ as the solvent required 31 hours to reach a yield of 66%.

Without being bound by theory, it may be that the transmetalation of $AlY^1_3$ with ArMgBr, or the transmetalation of $AlY^1_3$ with ArLi, or the transmetalation of $AlY^1_3$ with $Ar_3Al$ occurs effectively to give $Ar_nAlY^1_p$ either in the premixing stage before heating in the arylation reaction step, or early in the arylation reaction step upon initial heating. By way of example, mixing of $AlCl_3$ and $PhMgBr$ at ambient temperature for an hour provided an arylating reagent that led to comparable arylation yield, reactivity and chemoselectivity as when the reagents were mixed under the same conditions for 16 hours prior to the arylation reaction.

In one embodiment, the arylation reaction is performed by contacting the arylating reagent with a base-deprotonated compound of formula II or XI where $R^1$ is a protecting group and $R^2=M^4$ and where $M^4$ is Na, Li, K, Al or MgX, where X is a halide or another molecule of deprotonated compound of formula II or XI to form a dimer. Although the deprotonation process of the compound of formula II or XI can also be conducted with the arylating reagent $Ar_nAlY^1_p$ this requires an elevated temperature and is less cost effective because the Ar group acts as the base and 1 molar equivalent of Ar is wasted, and this method for deprotonation is therefore less preferred from a raw material cost perspective. The in situ deprotonating process of the compound of formula II or XI, where $R^2=H$, by direct contact with the arylating reagent is rapid and is complete before the arylation reaction has substantially taken place. Deprotonation of the compound of formula II or XI, where $R^1$ is a protecting group and $R^2=H$, prior to the arylation reaction can be a rapidly and conveniently accomplished at ambient temperature or below by contact with 1 molar equivalent of cheap and readily available commercial n-butyllithium (n-BuLi) solution (such as is supplied in hexanes) or diisobutylaluminum (i-Bu$_2$AlH; DIBAL) solution (such as supplied in PhMe). In preferred embodiments where deprotonation of the compound of formula II, where $R^1$ is a protecting group and $R^2=H$ is conducted prior to the arylation reaction, 1 molar equivalent of a solution of n-BuLi or i-Bu$_2$AlH is used. Following deprotonation and mixing of the deprotonated compound of formula II, where $R^1$ is a protecting group and $R^2=Li$ or $R^2=Al(i-Bu)_2$, with the arylating reagent, the low boiling solvents including that from the solution of base are optionally evaporated and then the arylation step is conducted.

Optionally, a Lewis acid $M^3Y^2_r$ can additionally be used as an additive in the arylation methods described herein. The Lewis acids comprise a metal or metalloid $M^3$ and a ligand $Y^2$ such as an anion, or a combination of anions. The subscript r is a number from 1 to 7. $M^3Y^2_r$ includes boron trihalides (such as BF$_3$ or BF$_3$.Et$_2$O, BCl$_3$) and other boron-based Lewis acids (such as borates), aluminum-based Lewis acids including AlCl$_3$, titanium-based Lewis acids including TiCl$_4$ and Ti(Oi-Pr$_2$)$_4$ and mixture of both, tin-based Lewis acids including SnCl$_4$, zinc-based Lewis acids including ZnCl$_2$, magnesium-based Lewis acids including MgCl$_2$, MgBr$_2$ and Mg(OTf)$_2$, lithium-based Lewis acids including LiOTf, LiOClO$_3$, scandium-based Lewis acids including Sc(OTf)$_3$, lanthanide-based Lewis acids represented by Ln(OTf)$_3$, where Ln is La, Ce, Pr, Nd, Pm, Sm, Eu, Gd, Tb, Dy, Ho, Er, Tm, Yb, Lu, and transition metal Lewis acids including ZrCl$_4$, Zr(OTf)$_4$, HfCl$_4$, Hf(OTf)$_4$, and Bi(OTf)$_3$. Non-metallic Lewis acids $M^3Y^2_r$ include but is not limited to TMSOTf, TESOTf and TBSOTf.

The Lewis acid might be intentionally added to the reaction to promote the reaction, or it might exist in the reaction mixture as a result of the synthesis the arylating reagent $[Ar_nM^1Y^1_p]M^2_q$. For example, the synthesis of Ph$_3$Al from 1 mole of AlCl$_3$ and 3 moles of PhMgCl will produce 3 moles of the Lewis acid MgCl$_2$ as a by-product, however, it is not the intention herein to exhaustively specify these extraneous salts in the formula $[Ar_nM^1Y^1_p]M^2_q$ although one skilled in the art will recognize that certain salts might form complexes with $[Ar_nM^1Y^1_p]M^2_q$. Crude Ph$_3$Al prepared from 1 mole of AlCl$_3$ and 3 moles of PhMgCl that was not purified would comprise both Ph$_3$Al and MgCl$_2$. These species might exist in solution as separate molecules or together form complexes, such as [Ph$_3$AlCl]MgCl.

In some embodiments the addition of Lewis acids can have a strong influence on the arylation reaction rate, chemoselectivity and yield. In some cases this influence can be a negative one. For example, when the compound of formula II, where $R^1$=TBDPS and $R^2$=H, was arylated with 2 molar equivalents of Ph$_3$Al in PhOMe/Bu$_2$O solvent mixture at 130° C. (external bath temperature), the addition of 6 molar equivalents of LiCl to the reaction resulted in a greater than halving of the assay yield from 67% in the blank experiment to 22% and increased the level of a side reaction. Under the same reaction conditions, the addition of 1 molar equivalent of MgCl$_2$ reduced the assay yield from 67% in the blank experiment to 51% and the addition of 4 molar equivalents of MgCl$_2$ reduced the assay yield from 67% in the blank experiment to 5%. The addition of MgBr$_2$ or Mg(OTf)$_2$ also had a negative, but less pronounced, impact on the reaction. Furthermore, non-metallic halide salts can have a negative impact on the arylation reaction. For example, a test addition of 1 molar equivalent of tetraphenylphosphonium chloride (Ph$_4$PCl) to the arylation reaction with 2 molar equivalents of Ph$_3$Al in PhOMe/Bu$_2$O solvent mixture at 130° C. (external bath temperature) of the compound of formula II, where $R^1$=TBDPS and $R^2$=H, result in a greater than halving of the assay yield from 67% in the blank experiment to 32%.

Therefore, in some instances it is preferred that the arylation reaction is conducted in the absence of either non-metallic halide salts or extraneous metallic halide salts (excluding those aluminum halide salts that are intentionally used).

By contrast, in other cases, the addition of Lewis acids can have a positive influence on the arylation reaction rate, chemoselectivity and yield. In some embodiments, when tri-arylaluminum (Ar$_3$Al) reagents are used in combination with trisubstituted aluminum(III) salts, AlY$^1_3$ (note that when $M^3=M^1=Al$ and $Y^2=Y^1$, the Lewis acid $M^3Y^2_r$ can be represented by the formula AlY$^1_3$), a significant improvement in reaction rate can be achieved, and moreover a lowering of the molar equivalents of the aryl group, Ar, is required with respect to the compound of formula II. For example, whereas the arylation of the compound of formula II, where $R^1$=TBDPS and $R^2$=H, with 2 molar equivalents of Ph$_3$Al in PhOMe/Bu$_2$O solvent mixture at 130° C. (external bath temperature) provided a 45% assay yield of the compound of formula IV, where $R^1$=TBDPS and $R^2$=H, after 8 hours (although this rose to 71% after about 30 hours), the use of 1.7 molar equivalents of Ph$_3$Al in combination with 0.3 molar equivalents of the Lewis acid AlCl$_3$ provided a 73% assay yield after 8 hours.

Given the above, it will be understood by those skilled in the art that Lewis acid additives can have both a positive or a negative influence on the arylation reaction, but optimal results can be obtained by one of skill in the art. In preferred embodiments, the Lewis acid is an aluminum(III) salt, AlY$^1_3$, where Y$^1$ includes halides, phenolate, sulfonates, carboxylates, alkoxides, carbanions and the like, and is preferably an aluminum trihalide such as AlCl$_3$ or AlBr$_3$.

Those skilled in the art will recognize that the anions Y$^1$ and Y$^2$ might be associated with either M$^1$ or M$^2$ or M$^3$ during the arylation reaction when $[Ar_nM^1Y^1_p]M^2_q$ and $M^3Y^2_r$ are used in conjunction. This is because anion ligands might interchange between metal cations in the solution phase when mixing of $[Ar_nM^1Y^1_p]M^2_q$ and $M^3Y^2_r$ occurs. Similarly, those skilled in the art will recognize that the cations M$^1$ or M$^2$ or M$^3$ might interchange during the arylation reaction when $[Ar_nM^1Y^1_p]M^2_q$ and $M^3Y^2_r$ are used in conjunction. Therefore, although $M^3Y^2_r$ is added to the reaction mixture, it is not the intention herein to state the fate of this species and the fate of $[Ar_nM^1Y^1_p]M^2_q$ on a molecular level in the reaction mixture. Also, it will be recognized by one skilled in the art that when $M^1=M^3=Al$, the arylating reagent $Ar_3Al$ and the Lewis acid $AlY^1_3$ can combine to form a hybrid arylating reagent represented by the formula $Ar_nAlY^1_p$ where the values of subscripts n and p will depend on the mole ratio of $Ar_3Al$ and $AlY^1_3$ that are combined together.

In some embodiments, the compound of formula XI is converted to the compound of formula I by treatment with metalated aryl compounds $[Ar_nM^1Y^1_p]M^2_q$ such as $Ar_3Al$ or $Ar_nAlY^1_p$, where n+p=3 and $Y^1$ is a halide (such as chloride), phenoxide, sulfonate, alkoxide, carboxylate or alkoxide, and where Ar is an aryl group as presented above, in the presence or absence of addition Lewis acids of the formula $M^3Y^2_r$. Although premixing of the triarylaluminum ($Ar_3Al$) reagents with $AlCl_3$ prior to the arylation reaction to provide arylating reagents represented by the formula $Ar_nAlCl_p$, where n+p=3), has proven beneficiation in terms of arylation reaction rate, the addition of the Lewis acids such as $AlCl_3$ and $BF_3$ (as its etherate complex $BF_3.Et_2O$) to the already partially reacted arylation reaction mixture already containing $Ar_3Al$ has also proven useful.

The preparation of the compound of formula XI and its subsequent arylation can be conducted using different operational approaches including the following: i) synthesis of the compound of formula XI without isolation of XI followed by its arylation, ii) synthesis of the compound of formula XI followed by its isolation with optional purification, followed by its arylation, iii) synthesis of the compound of formula XI with or without its isolation followed by contact at ambient temperature (i.e., without heating) with a metalated aryl compound $[Ar_nM^1Y^1_p]M^2_q$ such as $Ar_3Al$ or $Ar_nAlY^1_p$, where n+p=3 and $Y^1$ is a halide, such as chloride, to form a complex between XI and $[Ar_nM^1Y^1_p]M^2_q$ that can optionally be isolated as a solid (such as by precipitation and separation from the solvent phase) and then heated in a solvent to effect the arylation. Without being bound by theory, it is presumed that this complex comprises an Al—O bond between the Al atom of the arylating reagent and the C3-O group of the compound of formula XI that forms upon deprotonation of the C3-OH group by one molar equivalent of aryl anion provided by the arylating reagent. In cases where this complex is insoluble in the solvent, it precipitates and can be isolated by filtration. For example, when a solution of the compound of formula XI, where R=Ph, in PhMe was treated with 1 molar equivalent of $Ph_3Al$ in $Bu_2O$ at ambient temperature, a moisture sensitive white precipitate was formed within 5 minutes. When this white precipitate was heated to about 110° C. it dissolved in the PhMe/$Bu_2O$ solvent mixture and converted to the compound of formula I, where Ar=Ph. An additional operational approach is to follow approaches i) or ii) as described above, but prior to the arylation reaction the compound of formula XI is reacted with an aluminum base $R^a_2R^bAl$, such as i-$Bu_2AlH$. This is a more preferred compared to approach iii) because it is more economical as some of the arylating reagent is not wasted due to deprotonation of C3-OH by the Ar group of the arylation reagent itself.

Thus, in another embodiment, subsequent to the synthesis of the compound of formula XI and prior to the contact with a metalated aryl compound $[Ar_nM^1Y^1_p]M^2_q$ such as $Ar_3Al$ or $Ar_nAlY^1_p$, where n+p=3 and $Y^1$ is a halide, phenoxide, sulfonate, alkoxide, carboxylate or alkoxide, the compound of formula XI is deprotonated with a base. The base used to deprotonate prior to the arylation reaction is preferably a strong base, such as NaH, LiH, KH, $MgH_2$, LHMDS, NaH-MDS, i-$Bu_2AlH$, n-BuLi, s-BuLi, t-BuLi, PhLi, PhMgBr, i-PrMgCl or LDA is used. More preferably the base is a lithium base such as n-BuLi or an aluminum base such as i-$Bu_2AlH$. Preferably the deprotonation of the compound of formula XI with the base is conducted at ambient temperature or lower, such as 0° C., –20° C., –40° C., –60° C., or –78° C. Preferably only 1 molar equivalent of base is used with respect to the amount of compound of formula XI.

Figure 11:
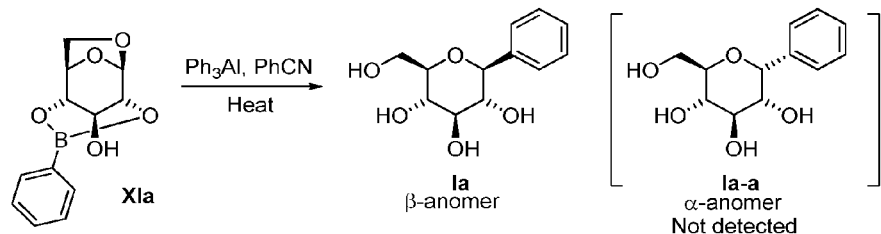
FIG. 11 provides a scheme for the highly stereoselective arylation of XIa to provide β-C-phenylglucoside Ia.
Figure 12:
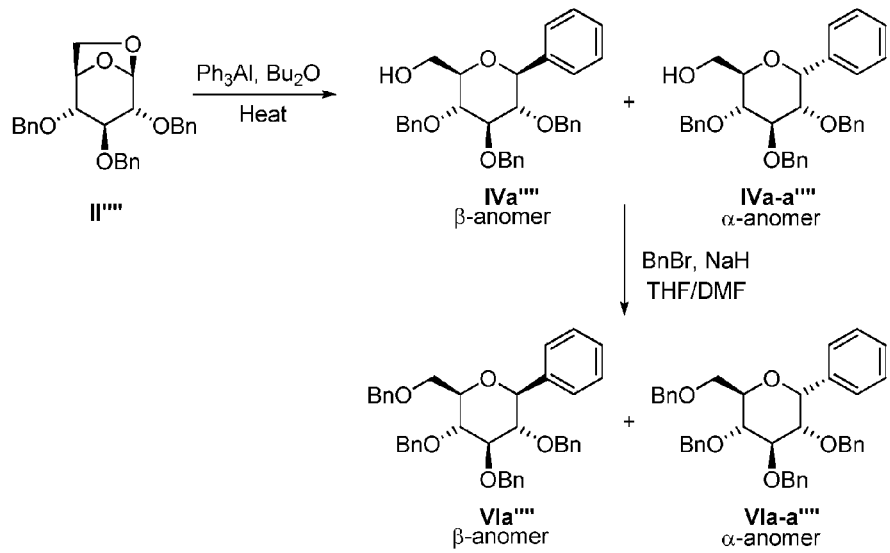
FIG. 12 provides a scheme for the stereoselective arylation of II'''' to provide the β-C-phenylglucoside IVa''''.
Figure 13:
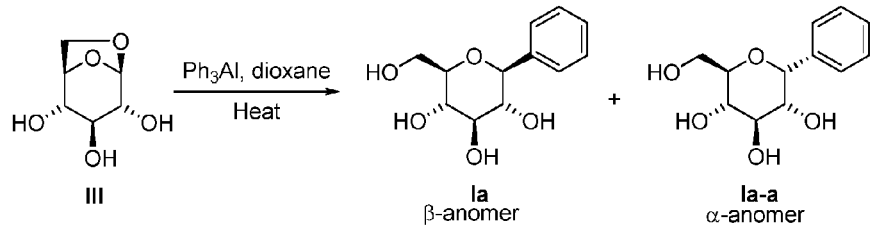
FIG. 13 provides a scheme for the stereoselective arylation of III to provide β-C-phenylglucoside Ia.
Figure 14:
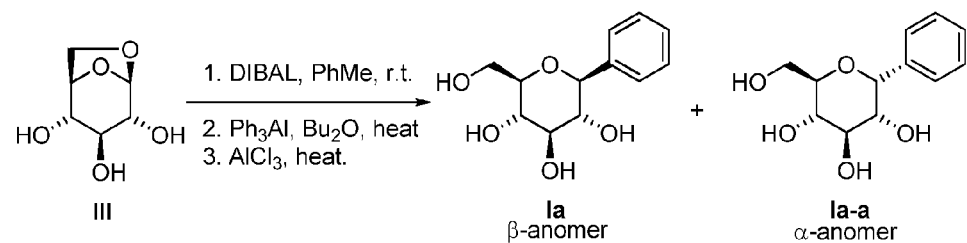
FIG. 14 provides a scheme for the stereoselective arylation of III to provide β-C-phenylglucoside Ia.

The arylation reaction of this invention is stereoselective for the β-anomer. That is, while the desired β-C-arylglucosides are obtained as the major C-arylglucoside stereoisomer product of the arylation reaction, either small amounts of the undesired α-C-arylglucosides are formed as co-products, or no detectable (i.e., within the detection limits of the analytical method) amounts of the undesired α-C-arylglucosides are formed. For example, the arylation of XIa with $Ph_3Al$ in PhCN provides exclusively β-C-phenylglucoside Ia (FIG. 11) as indicated by HPLC analysis. No α-C-phenylglucoside Ia-a could be detected by HPLC analysis, and by mass spectrometry analysis of the HPLC chromatogram, by comparison to a reference sample of the α-anomer Ia-a indicating that this reaction is highly stereoselective. Further, for example, the arylation of a compound of formula II, where $R^1$=TBDPS and $R^2$=H (i.e., II"), with prior deprotonated of C3-OH, using $Ph_{2.5}AlX_{0.5}$ (X is Cl or Br or a mixture) in PhOMe at >100° C. provides only the β-anomer of a compound of formula IV, where $R^1$=TBDPS, $R^2$=H and Ar=Ph (i.e., IVa"). Further, for example, the arylation of the compound of formula II, where $R^1$ and $R^2$ are benzyl, with $Ph_3Al$ in $Bu_2O$ followed by benzylation to provide the known (see *Tetrahedron: Asymmetry* 2003, 14, 3243-3247) tetra-O-benzyl derivatives showed (by HPLC analysis) a 99.6:0.4 mixture of the β-C-phenylglucoside VIa""/α-C-phenylglucoside VIa-a"" where $R^1$, $R^3$ and $R^4$ are benzyl (FIG. 12), indicating that this reaction is highly stereoselective. Further, for example, the arylation of the compound of formula III, that had been treated with $Ph_3Al$ in dioxane provided a 97.6:2.4 mixture of β-C-phenylglucoside Ia/α-C-phenylglucoside Ia-a (FIG. 13). In another example, the arylation of the compound of formula III, that had been pretreated with DIBAL in PhMe, with $Ph_3Al$ in PhMe/$Bu_2O$ provided a 93:7 mixture of β-C-phenylglucoside Ia/α-C-phenylglucoside Ia-a (FIG. 14), indicating that this reaction is stereoselective.

The reaction of the aluminum-based arylating reagents ($[Ar_nAlY^1_p]M^2_q$) described herein with the 1,6-anhydroglucopyranose compounds in this invention is typically chemoselective. That is, when the arylation reaction is conducted under preferred conditions with the preferred carbohydrate protecting groups and arylating reagent it favours arylation over several known side reactions.

A known side reaction in the arylation of 2,4-O-di-protected 1,6-anhydroglucopyranose compounds II, such as where $R^1$=TBDPS and $R^2$=H, is deoxygenation, and this is presumed to provide compounds of the formula XVII. Treatment of compounds of the formula XVII under acidic conditions, such as aqueous acid (e.g., aqueous trifluoroacetic acid), can provide (–)-levoglucosenone and a silanol (such as t-BuPh$_2$SiOH when $R^1$=TBDPS). This deoxygenation reaction can be controlled by the optimization of the reaction conditions, control of the quality of the aluminum reagent(s) used to prepare the arylating reagent and fine tuning of the arylating reagent $[Ar_nAlY^1_p]M^2_q$, such as varying the ratio of Ar to Al and the ratio of $Y^1$ to Al. The inventors also discovered that the amount of deoxygenation side reaction that competed with the desired arylation reaction increased when organometallic reagents and/or aluminum(III) reagents (i.e., $AlY^1_3$ such as $AlCl_3$) that were used to prepare the arylating reagent underwent a change in concentration (potency) and/or degradation during storage. Therefore the organometallic reagents and/or aluminum(III) reagents used in the preparation of the arylating reagents of this invention are preferably of good and defined quality. Quality control of these reagents can ensure predictable yields and reproducibility of the arylation reaction. Generally speaking, deoxygenation is suppressed when the mole ratio of Ar to Al is between 3.0 to 1.5 (i.e., n is between 3.0 to 1.5) or more preferably, between 2.5 to 2.0 (i.e., n is between 2.5 to 2.0) and the mole ratio of $Y^1$, when $Y^1$ is chloride, to Al is equal to or less than 1.0 (i.e., p is <=1.0). Deoxygenation can also be suppressed by conducting the arylation reaction of the compound of formula II at a temperature of about 120° C. or higher.

A known side reaction in the arylation of 2,3,4-O-tri-protected 1,6-anhydroglucopyranose compounds II, such as where $R^1=R^2=TBS$ or Bn, is deoxygenation and double arylation, and this is presumed to provide compounds of the formula XVIII and alcohols or silanols of formula $R^1OH$. Chemoselectivity for arylation of 2,3,4-O-tri-protected 1,6-anhydroglucopyranose compounds of formula II providing higher yields of the 2,3,4-O-tri-protected arylated products of formula IV can be improved by the use of triarylaluminum compounds, $Ar_3Al$, as the arylating reagents rather arylhaloaluminum compounds, such as $Ar_2AlCl$. This side reaction is also minimized by the use of benzyl protecting groups, or derivatives, instead of using silyl protecting groups.

A known side reaction in the arylation of 2,4-O-boronic ester protected 1,6-anhydroglucopyranose compounds XI is exchange of the carbon-based substituent on the boron atom of the boronic ester with the aluminum atom of the arylating reagent. This can result in the formation of small amounts of compounds of formula XIV where the anomeric position is substituted with the carbon-based substituent from the boron atom of the boronic ester rather than the aryl group of the arylating reagent. This side reaction can be suppressed in several ways, including i) by selection of boronic esters for which the boron substituent, R, does not, or is less prone to, transfer such as those possessing suitable electronic and steric characteristics, ii) use of a boronic ester in which the carbon-based substituent from the boron atom is an identical aryl group, Ar, to the aryl group of the arylating reagent (that is, in the compound of formula XI, R=Ar); iii) the use of diboronic esters of formula XIII, for which a carbon-based transferable group is absent in the reaction substrate.

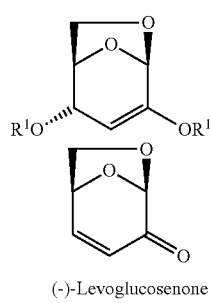

XVII

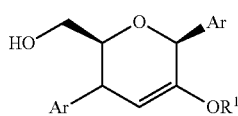

(-)-Levoglucosenone

XVIII

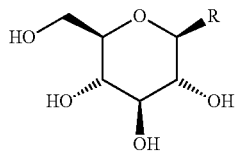

XIV

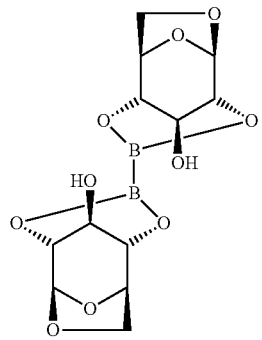

XIII

Other known side reactions include dimerisation of the aryl group, Ar, originating from the arylating reagent, to form biaryl compounds of the formula ArAr. This side reaction is generally minor, but can be suppressed by lowering the mole ratio of Ar to Al in the arylating reagent $[Ar_nAlY^1_p]M^2_q$ to less than 3.0 (i.e., n is <3.0), but is more suppressed when the mole ratio of Ar to Al is less than 2.5 (i.e., n is <2.5). Certain metal contaminants can promote this dimerization (see *J. Am. Chem. Soc.* 2007, 129, 13788-13789 and *Nature Chem.* 2010, 2, 313-318).

The arylation reaction is generally conducted in an inert solvent such as an aprotic solvent or mixture of solvents. The solvent or solvent mixture is generally one that is compatible with the metalated aryl compound $[Ar_nM^1Y^1_p]M^2_q$. Suitable solvents include, but are not limited to hydrocarbons, halogenated hydrocarbons, aromatic hydrocarbons, halogenated aromatic hydrocarbons, heteroaromatic compounds, ethers and nitriles, including for example, dichloromethane (DCM), xylene (any isomer or mixture of isomers), toluene (PhMe), anisole (PhOMe), phenetole (PhOEt), di-n-butyl ether ($Bu_2O$), diphenyl ether ($Ph_2O$), chlorobenzene (PhCl), 1,4-dioxane (dioxane), benzonitrile (PhCN), tetrahydrofuran (THF), 2-methyltetrahydrofuran (2-MeTHF), N,N-dimethylformamide (DMF), and N,N-dimethylacetamide (DMAC). Some ether solvents undergo partial decomposition in the presence of the metalated aryl compound $[Ar_nM^1Y^1_p]M^2_q$ during prolonged heating at high temperatures. For example, PhOMe undergoes conversion to phenol in the presence of metalated aryl compounds of the formula $Ar_nAlCl_p$, and although this leads to the destruction of some of the arylating reagent, it is not a large issue, especially when the arylation reaction itself is rapid. Further, some nitrile solvents such as PhCN can undergo reaction with the arylating reagent, but this is less significant when the arylation reaction is rapid due to high reactivity of the reaction substrate (such as the compound of formula XI) and is also suppressed at lower reaction temperatures, such as below 130° C. Those skilled in the art will recognize that the metalated aryl compounds $[Ar_nM^1Y^1_p]M^2_q$ and their precursors (e.g., Grignard and aryllithium compounds) will be oxygen and moisture sensitive and therefore the synthesis and handling of the reagents, and the arylation reaction itself, should be conducted under dry and oxygen-free conditions. This can be achieved in conventional reactor vessels by the use of solvents that have been dried over molecular sieves, or other methods known in the art, and the use of a dry and inert atmosphere (e.g., nitrogen or argon) during the reagent preparation and arylation reaction. In this invention, Lewis basic solvents such as PhOMe, dioxane and PhCN have been found to be particularly useful. Whereas PhOMe was the preferred solvent for the arylation reaction of the compound of formula II, where $R^1$=TBDPS or TBS and $R^2$=H, dioxane was a preferred solvent for the arylation reaction of the compound of formula III, and PhCN was a preferred solvent for the arylation reaction of the compound of formula XI, where R=Ph. PhOMe was also a particularly useful solvent in the arylation reaction of the compound of formula XI, where R=Ph. Without being bound by theory, it is suspected that the combination of Lewis basicity, sufficient solvating ability and sufficiently high boiling point of the solvent might contribute to the good characteristics of the more useful solvents in this invention.

In some embodiments, a solvent with a boiling point higher than 75° C. is preferred. Preferably the arylation reactions are conducted at an internal temperature of about between 80° C. and 180° C., but the optimum reaction temperature depends on the combination of reaction conditions used, such as the reaction concentration, the chemical structure of the Ar group of the arylating reagent being used, the protecting groups and the configuration of the protecting groups used to protect the hydroxyl groups of the carbohydrate. For example, whereas some arylation reactions using certain Ar groups can reach completion rapidly, such as in less than 4 hours, other arylation reactions using certain other Ar groups require longer, such as 12 h or longer.

It is most preferred that heating of the reaction mixture is terminated as soon as the compound of formula IV has reached its maximum yield, which can be determined by reaction monitoring using HPLC purity analysis and HPLC assay techniques that are known to those skilled in the arts. In some embodiments with certain aryl groups, Ar, partial decomposition of the arylated product can occur when the product mixture is heated further beyond the point in time at which the maximum chemical yield was reached. The inventors discovered that the amount and rate of this decomposition varied significantly between different reaction systems (e.g., solvents, temperatures, and reaction concentration) and when different aryl groups and different hydroxyl protecting groups were used on the carbohydrate. For example, when the arylation products of formula IV, where $R^2$=TBDPS and $R^2$=H and Ar=4-methoxyphenyl, 2-methoxyphenyl or 2-thienyl, were heated at >100° C. in the arylation reaction mixture that they were formed in beyond the time point of maximum chemical yield, they partially decomposed. By way of example, a halving in the chemical yield of the 4-methoxyphenyl and 2-thienyl arylated products of formula IV, where $R^2$=TBDPS and $R^2$=H, occurred over an approximately 12-16 hour period, whereas under the same conditions the 2-furyl, phenyl and many other phenyl derivatised arylated product of formula IV underwent no significant decomposition. Further, whereas arylation of the compound of formula II, where $R^2$=H, typically requires a temperature of about >110° C., arylation of boronic esters XI, where $R^2$=H, can be conducted at lower temperatures such as below 100° C., such as at 80° C.

It has been discovered that mildly Lewis basic solvents, such as PhOMe for example, are more preferable to non-Lewis basic solvents such as PhMe, for example. By way of example, a direct comparison between PhMe and PhOMe shall be made as follows. When the compound of formula II, where $R^2$=TBDPS and $R^2$=H, was first deprotonated with 1 molar equivalent of PhMgBr followed by arylation with 1.5 molar equivalents of an arylation represented by the formula $Ph_{2.5}AlX_{0.5}$, where X is Cl and Br, that was prepared prior to the reaction by mixing 1.5 molar equivalents $AlCl_3$ and 3.75 molar equivalents of PhMgBr, in PhMe solvent at an external bath temperature of 130° C., a maximum chemical yield was 42% as determined by HPLC assay. Under the same conditions, but using PhOMe as solvent, 64% yield was obtained. Without being bound by theory, this is thought this benefit of the ether solvents arise from i) the break-down of aggregates of the arylating reagent and improved solubilization of the arylating reagent, ii) promotion of the arylation reaction through assistance of the turnover of the arylating reagent or of the Lewis acid, or iii) through complexation, with an increase of the electron richness of the arylating reagent and therefore nucleophilicity of the aryl group(s), Ar. Some characteristics of PhOMe, such as its boiling point and its solvating ability to maintain a homogeneous reaction mixture throughout make PhOMe the most preferred solvent of some embodiments, such as the embodiment of the arylation of a compound of formula II where $R^1$ is a silyl protecting group, such as TBS or TBDPS, and $R^2$=H.

It has been discovered that some ether solvents (e.g., THF) with low boiling points (e.g., below 90° C.) can retard the rate of the arylation reaction. For example, when the arylating reagent represented by the formula $Ph_{2.5}AlCl_{0.5}$ was prepared in ether solvents such as THF, by the transmetalation of $AlCl_3$ with PhMgCl, the residual low boiling point ether solvent retarded the rate of arylation reaction. To circumvent this problem the arylating reagents $[Ar_nM^1Y^1_p]M^2_q$ can be prepared in the preferred arylation reaction solvent, in the circumstance that the solvent is applicable to the arylating reagent synthesis. Alternatively, a solvent swap to remove the lower boiling solvent residues from the $[Ar_nM^1Y^1_p]M^2_q$ mixture is optionally conducted to circumvent the aforementioned problem. In fact, the inventors discovered that by conducting a solvent evaporation step to remove the more volatile solvents, followed by dilution with a second, higher boiling solvent prior to initiating the arylation reaction, a dramatic improvement in the arylation reaction rate was observed. Alternatively, this "solvent swap" operation can be performed without prior evaporation of the lower boiling solvent by dilution of the original lower boiling solvent solution of arylating reagent with a higher boiling point solvent, and then distilling off the lower boiling solvent from the mixture to provide a solution of the arylating reagent in higher boiling point solvent. Given that the method of solvent swap operation described herein does not impact the arylation reaction itself, the method used in the manufacturing plant should be determined as a result of which ever method is most time and cost efficient in the manufacturing plant.

In embodiments wherein $R^1$ are silyl protecting groups and $R^2$ is hydrogen, although a range of solvents can be used in the arylation reaction, some solvents such as PhOMe are more preferred. For those instances in which the compound of formula II is deprotonated using a base before the arylation reaction, the subsequent arylation reaction functions effectively in PhMe as solvent. In this instance, a prior solvent swap to remove low boiling point ether solvents is helpful, and the use of between 2 and 4 molar equivalents of the metalated aryl compound represented by the formula $Ar_{2.5}AlCl_{0.5}$, preferably about 2 equivalents to minimize costs. When less than 2 equivalents of the metalated aryl compound $Ar_{2.5}AlCl_{0.5}$ is used (such as 1.5 molar equivalents for example) in PhMe as solvent, however, the arylation reaction efficiency is reduced as indicated by a significant reduction in the chemical yield. In contrast, when the compound of formula II, where $R^1$ is a silyl protecting group and $R^2$=H, is deprotonated with a base before the arylation reaction, and then the arylation reaction is conducted using PhOMe as the arylation solvent, the reaction functions efficiently using 1.5 molar equivalents and even when using 1.2 equivalents of the metalated aryl compound represented by the formula $Ar_{2.5}AlCl_{0.5}$. Thus, using PhOMe as the solvent can allow a significant reduction in the required molar equivalents of the metalated aryl compound $[Ar_nM^1Y^1_p]M^2_q$ with respect to compound II, where $R^2$=H, and therefore making a more cost efficient reaction.

When 2,4-di-O-protected 1,6-anhydroglucopyranose II, where $R^2$=H, is arylated with the metalated aryl compound, preferably with deprotonation being conducted with a base, such as n-BuLi, prior to the arylation reaction, the mole ratio of $M^1$ and the aryl group can affect the efficiency of the arylation reaction. When $M^1$ in the arylating reagent of the formula $[Ar_nM^1Y^1_p]M^2_q$ is not Al, the mole ratio of $M^1$/Ar varies from about 1:1 to 1:6. That is, the subscript value n is 1 to 6. When $M^1$ is Al, as in the preferred embodiments, the mole ratio of $M^1$/Ar varies from about 1:1 to 1:4. That is, the subscript value n is 1 to 4. Although arylation can occur using a range of values of n, the inventors discovered the efficiency, arylation rate and amount of undesired side product(s) is very dependent on the ratio of Ar to $M^1$. Therefore some ranges of ratios of Ar to $M^1$ are more preferred to other ranges.

When $M^1$ is Al and when the compound of formula II, where $R^2$=H, is deprotonated with a base prior to the arylation reaction, preferably n is in the range of about 2.0 to 2.5 (i.e., the ratio of $M^1$ to Ar is preferably about 1:2.0 to 1:2.5). When the compound of formula II, where $R^2$=H, is not deprotonated prior to the arylation reaction the amount of aryl group, Ar, is generally increased to account for loss of some aryl group during exposure to the unprotected C3-O hydroxyl group and it is preferred that n is 3.0-3.5. It has been discovered that when $M^1$ is Al and n is 2.5 (i.e., the mole ratio of Al to Ar is about 1:2.5) and the compound of formula II was deprotonated with a base prior to the arylation reaction, the arylation reaction rate was lower than when n was 2.0 (and the compound of formula II was deprotonated with a base prior to the arylating reagent), where the arylation reaction rate was faster but with a lower yield due to side reactions. It has been discovered that when $M^1$ is Al and n is 3 (i.e., the mole ratio of Al:Ar is about 1:3) and the compound of formula II, where $R^2$=H, is deprotonated prior to the arylation reaction, the arylation reaction rate was significantly reduced.

Generally, the inventors discovered that when the ratio of Ar to Al was higher (such as when n=2 to 3), the arylation reaction rate was lower but the amount of side product(s) was less than when the ratio of Ar to Al was lower (such as when n=1 to <2). In fact, Ar to Al ratios of <2:1, such as 1.5:1 or 1:1, are least preferred because they lead to low yields and impure product mixtures due to side reaction(s). For example, whereas arylation with 2 molar equivalents of the arylating reagent $[Ph_{2.5}AlY^1_p]M^2_q$ (prepared from a mixture of 2.0 molar equivalents $AlCl_3$ and 5.0 molar equivalents of PhMgBr) of the compound of formula II, where $R^1$=TBDPS and $R^2$=H, which was deprotonated with 1 molar equivalents of the base PhMgBr prior to the arylation reaction provided a 60% yield after 19 hours heating in PhOMe as a solvent at 130° C. (external bath temperature), arylation with $[Ph_{3.0}AlY^1_p]M^2_q$ (prepared from a mixture of 2.0 molar equivalents $AlCl_3$ and 6.0 molar equivalents of PhMgBr) using the same methods and conditions provided a lower 50% yield at 30 hours. Moreover, arylation of the compound of formula II, where $R^1$=TBDPS and $R^2$=H, with the arylating reagent $[Ph_{2.0}AlY^1_p]M^2_q$ (prepared from a mixture of 2.0 molar equivalents $AlCl_3$ and 4.0 molar equivalents of PhMgBr) under using the same methods and conditions provided showed a 60% yield at 7 hours, arylation with $[Ph_{1.5}AlY^1_p]M^2_q$ (prepared from a mixture of 2.0 molar equivalents $AlCl_3$ and 3.0 molar equivalents of PhMgBr) showed 54% yield at 4 hours. In yet another example, arylation of the compound of formula II, where $R^1$=TBDPS and $R^2$=H, which was deprotonated prior to the arylation reaction with PhMgBr, with the arylating reagent $[Ph_{1.0}AlY^1_p]M^2_q$ (prepared from a mixture of 2.0 molar equivalents $AlCl_3$ and 2.0 molar equivalents of PhMgBr) provided a maximum yield of 9.8% at 2 hours.

The use of non-transferable ligands, herein also referred to as "dummy ligands", was also evaluated in the arylating reagent of formula $[Ar_nM^1Y^1_p]M^2_q$. Given that the aryl group contributes a significant portion of the cost of the arylating reagent, the partial replacement of aryl groups, Ar, with dummy ligands such as halides, sulfonates and phenoxides can reduce costs. One skilled in the art will understand that different reactivities of arylating reagents may occur upon substituting the aryl groups with different dummy ligands. With cost and reactivity of the arylating reagent in consideration, halides such as chloride are the preferred dummy ligands in this invention. In fact, the inventors discovered that the use of halide dummy ligands actually improved the reactivity of the arylating reagent of formula $Ar_nM^1Y^1_p$, where $Y^1$ is a halide dummy ligand. Arylating reagents of formula $Ar_nM^1Y^1_p$, where $Y^1$ is a halide dummy ligand and $M^1$=Al, of this embodiment can be readily prepared by mixing triarylaluminum complexes ($Ar_3Al$) with aluminum trihalides ($AlY^1_3$, where $Y^1$ is a halide) at ambient temperature in a suitable solvent or solvents mixture for less than 1 hour, for about 1 hour or for several hours, prior to the arylation reaction. In these embodiments the arylating reagent represent by the formula $[Ar_nM^1Y^1_p]M^2_q$ is more concisely represented by the formula $Ar_nAlY^1_p$, where $Y^1$ is a halide.

The arylating reagent represented by the formula $Ar_nAlY^1_p$, where $Y^1$ is a halide are prepared prior to the arylation reaction by the mixing of aluminum trihalides, such as $AlCl_3$, and triarylaluminum, $Ar_3Al$, and are preferably prepared from a mole ratio of $Ar_3Al$ to $AlCl_3$ of about 1:1 to 20:1, or more preferably about 1.5.0:1 to 15:1. Increasing the proportion of $Ar_3Al$ and lowering the proportion of $AlCl_3$ too much, or decreasing the proportion of $Ar_3Al$ and increasing the proportion of $AlCl_3$ too much results in lower reaction yields and when the proportion of $AlCl_3$ is too high, increased impurity formation. $AlBr_3$ can also be used in place of $AlCl_3$.

One skilled in the art will recognize that other arylating reagents represented by the formula $Ar_nAlY^1_p$, where $Y^1$ is not a halide can be used in the arylation of the 1,6-anhydroglucopyranose compounds of this invention. For example, $Y^1$ can be selected from the group sulfonates, such as methanesulfonate or trifluoromethanesulfonate (also known as triflate or OTf), phenolates, such as phenolate, 2,6-dihalophenolates and 2,3,4,5,6-pentahalophenolates, carboxylates such as trifluoroacetates, alkoxides or carbanions, with the proviso that $Y^1$ does substantially react with the arylation substrate to provide side products. Arylating reagents represented by the formula $Ar_nAlY^1_p$, where $Y^1$ is not a halide can be prepared from prior to the arylation reaction by the mixing of trisubstituted aluminum salts, $AlY^1_3$, and triarylaluminum, $Ar_3Al$, compounds. $AlY^1_3$ compound may exists as dimers, $Al_2Y^1_6$, but will be represent herein by the empirical formula $AlY^1_3$ for convenience. $AlY^1_3$, where $Y^1$=OTf (aluminum(III) triflate or aluminum trifluoromethanesulfonate) or $Y^1$=OPh (aluminum phenoxide), can be prepared as described in the art (see *J. Am. Chem. Soc.* 1988, 110, 2560-2565 for $Y^1$=OTf and *Organometallics* 2007, 26, 2561-2569 for $Y^1$=OC$_6$F$_5$) or obtained from commercial sources (for example, AlY$^1{}_3$, where Y$^1$=OTf or OPh are commercially available).

In the following examples, the compound of formula II is not deprotonated prior to the arylation, but instead the arylating reagent itself acts as the base to deprotonate C3-OH. By way of example, whereas the reaction of the compound of formula II, where R$^1$=TBDPS and R$^2$=H, with 2 molar equivalents of the arylating reagent of the formula Ph$_3$Al (for which no dummy ligand Y$^1$ is present) in PhOMe/Bu$_2$O as solvent gave a 66% assay yield of the product of formula IV, where Ar=Ph (i.e., compound IVa"), after heating for 31 hours at 130° C., reaction of the same compound of formula II with 2 molar equivalents an arylating reagent of the formula Ph$_{2.5}$AlCl$_{0.5}$ (i.e., the dummy ligand Y$^1$=Cl), prepared from 0.3 molar equivalents of AlCl$_3$ and 1.7 molar equivalents Ph$_3$Al, gave a 73% assay yield of product of formula IVa" after heating for 8 hours. In yet another example, reaction of the compound of formula II, where R$^1$=TBDPS and R$^2$=H, under the same conditions with 2 molar equivalents of a arylating reagent of formula Ph$_{2.5}$Al(C$_6$F$_5$O)$_{0.5}$ in which the pentafluorophenoxy group is the dummy ligand (i.e., Y$^1$=OC$_6$F$_5$) gave a 73% assay yield of the product of formula IVa" after 12 hours. In still another example under the same conditions, reaction of the compound of formula II, where R$^1$=TBDPS and R$^2$=H, with 2 molar equivalents of an arylating reagent of formula Ph$_{2.5}$Al(OPh)$_{0.5}$ in which the phenoxy group is the dummy ligand (i.e., Y$^1$=OPh) gave a 59% assay yield of the product of formula IVa", after 24 hours. From these examples it can be seen that the aryl group, Ar, can be partially replaced with dummy ligands and good or improved reactivity of the arylating reagent is retained.

Although phenoxy and halide ligands have been demonstrated to be useful, one skilled in the art would realize that other dummy ligands, including pseudohalides, such as sulfonates, carbanions, cyanide, cyanates and the like, might also be useful. Carbanions include alkyl and aryl groups, however, when these dummy ligands are used, the carbanion is preferably one that does not substantially compete with Ar in the arylation reaction. That is, the dummy ligand should not substantially react with the compound of formula II during the arylation reaction to afford compounds of formula XIV wherein R=the carbanion dummy ligand, Y$^1$. In preferred embodiments the dummy ligand is a halide, and in more preferred embodiments the dummy ligand is chloride. In particular, in arylation of the compound of formula II, where R$^1$ is a protecting group and R$^2$=H, with 2 molar equivalents of a compound represented by the formula Ph$_{2.5}$AlY$^1{}_{0.5}$, prepared from 0.33 molar equivalents of AlY$^1{}_3$ and 1.66 molar equivalents Ph$_3$Al, that also acts as the base to deprotonate C3-OH, chloride is the preferred dummy ligand Y$^1$. When the compound of formula II, where R$^1$ is a protecting group and R$^2$=H, is deprotonated prior to contact with the arylating reagent with a base, such as n-BuLi, 2 molar equivalents of an arylating reagent represented by the formula Ph$_2$AlY$^1{}_1$ is preferred, where chloride is the preferred dummy ligand Y$^1$.

In some embodiments, converting the compound of formula II, wherein R$^1$ of C2-O and C4-O together forms a chain and R$^2$ is hydrogen (i.e., X), to the compound of formula I, wherein R$^1$ is H, solvents including but not limited to PhMe, PhOMe, PhOEt, PhCl, PhCN, 1,2-dichlorobenzene, Bu$_2$O, dioxane, MeCN, n-BuCN and t-BuCN are suitable in the arylation reaction. In one embodiment, PhCN is a preferred solvent with less metalated aryl compound [Ar$_n$M$^1$Y$^1{}_p$]M$^2{}_q$, for example only about 1 molar equivalent with respect to the compound of formula XI than is normally required, being required and provides a very rapid and efficient arylation reaction. In this embodiment using PhCN as the solvent the reaction can be conducted at >100° C. but the reaction is preferably conducted at above or about 150° C. In embodiments using other solvents the reaction can be conducted at >80° C., preferably at about 100° C., or at the boiling point of the solvent. In other embodiments, PhOMe, Bu$_2$O, and PhCl are preferred solvents and about 1.5 to 2.6 molar equivalents of the arylating reagent are used, which are preferably prepared by mixing of aluminum trihalides, such as AlCl$_3$, and triarylaluminum, Ar$_3$Al, for less than 1 hour to several hours at ambient temperature prior to contact with the compound of formula XI.

In embodiments were the arylating reagent [Ar$_n$M$^1$Y$^1{}_p$]M$^2{}_q$ is prepared prior to the arylation reaction by the mixing of aluminum trihalides, such as AlCl$_3$, and triarylaluminum, Ar$_3$Al, PhOMe is good solvent for the arylation reaction because it possesses acceptable solvating characteristics and is a preferred solvent from a manufacturing perspective because it cost effective and relatively non-toxic. This solvent can also be used effectively in the presence of other solvents (co-solvents) including, but not limited to, PhMe, PhCl, PhCN, Bu$_2$O, 1,4-dioxane. Preferably the co-solvent has a boiling point at or above the required arylation reaction temperature. Therefore, in preferred embodiments, the arylation of the compound of formula XI in conducted in mixtures of PhOMe and other solvents or is more preferably conducted in PhOMe without additional solvents.

In embodiments were the arylating reagent [Ar$_n$M$^1$Y$^1{}_p$]M$^2{}_q$ is prepared prior to the arylation reaction by the mixing of aluminum trihalides, such as AlCl$_3$, and triarylaluminum, Ar$_3$Al, and the compound of formula XI is not deprotonated prior to contact with the arylating reagent, the aforementioned arylating reagent is preferably prepared from a mole ratio of Ar$_3$Al to AlCl$_3$ of about 3.5:1 to 20:1, more preferably about 5.0:1 to 15:1. Increasing the proportion of Ar$_3$Al and lowering the proportion of AlCl$_3$ too much, or decreasing the proportion of Ar$_3$Al and increasing the proportion of AlCl$_3$ too much results in lower reaction yields and when the proportion of AlCl$_3$ is too high, increased impurity formation. Under these preferred conditions in PhOMe at about 100° C. (internal reaction temperature), the arylation reaction is complete within 1 to 3 hours, although the reaction can be conducted at temperatures such as 80° C. through to 150° C.

In embodiments where the compound of formula XI is not deprotonated prior to contact with the arylating reagent, the arylating reagent is presumed to act as the base to deprotonate the C3-OH. In this scenario, it has been discovered that the optimum ratio of the aluminum trihalides, such as AlCl$_3$, and triarylaluminum, Ar$_3$Al actually depends on the total molar equivalents of arylating reagent [Ar$_n$M$^1$Y$^1{}_p$]M$^2{}_q$ and this optimum ratio can be determined by experimentation.

In yet another embodiment three options are available: i) a molar excess of metalated aryl compound [Ar$_n$M$^1$Y$^1{}_p$]M$^2{}_q$ with respect to a compound of formula XI is used, ii) an additional Lewis acid is used, such as AlCl$_3$ or BF$_3$, or iii) Lewis basic additives are added to the reaction mixture such as benzonitrile or substituted benzonitriles. Since in some embodiments the compound of formula XI is prepared prior to the arylation reaction and used directly, a solvent swap to remove the solvent that the compound of formula XI was prepared in and the solvent that the arylating reagent [Ar$_n$M$^1$Y$^1{}_p$]M$^2{}_q$ was prepared in, or dissolved in if a commercially available reagent, can optionally be conducted prior to initiating the arylation reaction to remove lower boiling solvent residues from reaction mixture since these can retard the arylation reaction.

Other features of the arylation reaction conditions (e.g., temperature, order of reagent addition, concentration of reagents, timing of addition, and the like) will generally be dependent on the nature and expense of the starting reagents. One of skill in the art will appreciate that modifications can be made to the conditions provided in the Examples below.

Subsequent to completion of the arylation reaction a halogen source, such as but not limited to iodine ($I_2$), bromine ($Br_2$), bromoiodide (BrI), N-bromosuccinimide (NBS), N-bromophthalimide, 1,3-dibromo-5,5-dimethylhydantoin (DBDMH), N-iodosuccinimide (NIS) and N-iodophthalimide, can be combined with the arylation reaction product mixture. This converts unreacted arylating reagent and its arylaluminum by-product(s) to an aryl halide compound of formula ArX, where X is the halide originating from the halogen source and Ar is the aryl group originating from the arylating reagent of formula $[Ar_n M^1 Y^1_p]M^2_q$. This halogenation reaction is preferably conducted at ambient temperature to minimize side reactions. Salts, such as but not limited to LiCl, can be added to this halogenation reaction to improve the conversion efficiency of the arylaluminum compound(s) to the aryl halide. Following halogenation of the unreacted arylating reagent and its by-product(s), the aryl halide is separated from the compound of formula IV, I, VI or V. In this embodiment an improvement in atom economy and cost may be achieved because the aryl halide compound of formula ArX can be recycled and reused upon its further conversion into the arylating reagent of formula $[Ar_n M^1 Y^1_p]M^2_q$.

Figure 10:
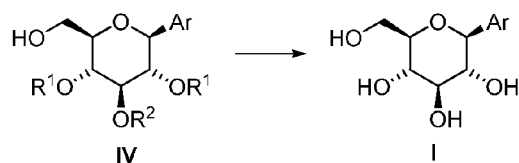
FIG. 10 provides a scheme for the deprotection of C-aryl glucoside compounds.

In some embodiments, the present invention provides a process of deprotection of the C-arylglucoside compound of formula IV to provide a compound of formula I by deprotection of $R^1$, and of $R^2$ when $R^2 \neq H$ (FIG. 10). In one group of embodiments, $R^1$ is a silyl protecting group which can be removed using fluoride reagents such as those known in the art for the deprotection of silyl ethers including aqueous HF, $3HF \cdot Et_3N$, HF.pyridine, TBAF, or HCl in an appropriate solvent. Suitable silyl protecting groups (for $R^1$) include, but are not limited to, TMS, TBS, TBDPS, TIPS and TES. When $R^1$ and $R^2$ are benzyl or substituted benzyl deprotection can be accomplished by hydrogenolysis. In another group of embodiments, each of $R^1$ together forms a chain between C2-O and C4-O, such as in the compound of formula XI and XII. When the protecting group comprises a boronic ester XI or stannylene acetal XII, a specific deprotection step is typically not be required and the protecting group is spontaneously removed either during the reaction or during the work-up, or both (see *J. Org. Chem.* 1990, 55, 5132-5139 for the deprotection of stannylene acetals from diols).

Figure 4:
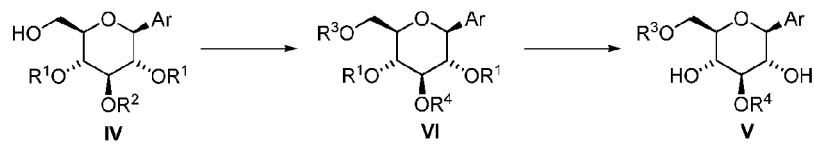
FIG. 4 provides a scheme for the preparation of SGLT2 prodrugs according to the methods of the present invention FIG. 5 provides a stereoselective synthetic process of β-C-arylglucosides without the protection on hydroxyl groups on sugar moiety.
Figure 5:
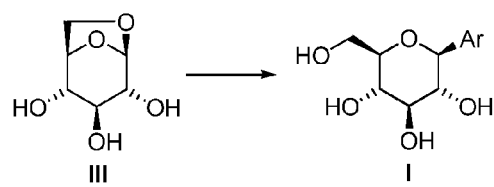
Figure 6:
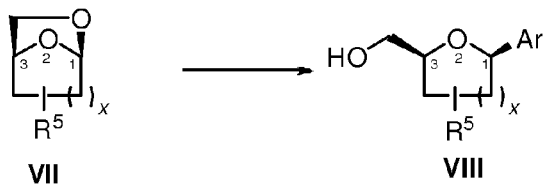
FIG. 6 provides a scheme for the arylation of 1,3-dioxolane compounds.
Figure 7:
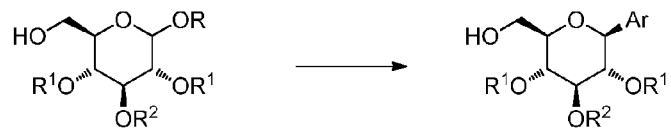
FIG. 7 provides a scheme for the preparation of β-C-arylglucosides from 1-O-glucosides.

In another aspect, the present invention provides a method to produce SGLT2 prodrugs (see FIG. 4). The compound of formula IV is not only useful for the preparation of compounds of formula I, but also for compounds of formula V which might function as prodrugs of compounds of formula I. The compounds of formula VI can be deprotected to remove $R^1$ to provide the potential prodrugs. In this case, $R^1$ comprises an oxygen protecting group that can be removed from the compound of formula VI without removal of $R^3$ and without removal of $R^4$ if $R^4 \neq H$. In one embodiment, prodrugs of SGLT2 inhibitors and related compounds of medicinal use of formula V can be obtained by applying the arylation methodology described herein to compounds of the formula II to provide compounds of formula IV followed by selective derivitisation, such as alkylcarboxylation, arylcarboxylation and acylation, of the C6-O position of the compound of formula IV, followed by deprotection of the protecting groups of the compound of formula VI. For example, when the compound of formula IVa, where $R^1$=TBDPS, Ar=Ph and $R^2$=H, produced by the arylation of the compound of formula II, where $R^1$=TBDPS and $R^2$=H, was treated with ethyl chloroformate in the presence of triethylamine and a catalytic amount of 4-(dimethylamino)pyridine (DMAP), the ethylcarboxylation was selective for the C6-O hydroxyl group to provide the compound of formula VI, where $R^1$=TBDPS, $R^2$=H and $R^3$=$CO_2$Et in high yield (96%). The compound of formula V was then generated in high yield (92%) by deprotection of TBDPS groups of the compound IV using TBAF.

The functional groups that might be useful in prodrugs include, for example, esters and carbonates, acyloxymethyl esters, acyloxymethyl ethers, phosphates, phosphonates, sulfates, sulfonates, tetrahydrofuranyl ethers, tetrahydropyranyl ethers, carbamates, and dicarbonate anhydrides. That is, $R^3$ of the compound of formula VI and V is —COR, —$CO_2$R, —$CO_2CH_2OCOR$, —$CH_2OCOR$, —P(O)(OR)$_2$, —P(O)(OH)O$^-$, —$SO_2OR$, —$SO_3^-$, —$PO_3^{2-}$, —CONHR, —CON(R)$_2$, —$CO_2COR$, —$CO_2CO_2R$, wherein R is a branched or unbranched $C_1$-$C_{20}$ alkyl or a $C_3$-$C_{20}$ cycloalkyl, and such that NHR and N(R)$_2$ portions comprise amino acid radicals. This aspect of the invention arises from the unique arylation reaction of compound of the formula II which provides a 2,4-di-O-protected C-glucoside or 2,3,4-tri-O-protected C-glucoside as the product in which the primary C6-O position, and secondary C3-O position when the 2,4-di-O-protected product is produced, are not protected. Accordingly, selective derivatisation can be carried out on the primary C6-O position (without derivatisation of the C3-O position where $R^2$=H due to the greater steric hindrance of the C3-O position). This selective derivatisation can be efficiently and selectively accomplished while the C2-O and C4-O positions are still protected with $R^1$. This is more difficult using other synthetic methodology as the C6-O position is typically protected with the same protecting groups as are found at the others positions. Because in some embodiments silyl protecting groups are preferred for $R^1$, removal of the C2-O and C4-O protecting groups can take place following prodrug formation at C6-O. The preparation process of this aspect is shown in FIG. 4. Furthermore, optionally both C6-O and C3-O can be derivatised to form prodrugs, where $R^4$=$R^3$ or where $R^3 \neq R^4$ and $R^4$=H.

In comparison with known methods of preparing β-C-arylglucosides and their derivatives, the embodiments of this invention described herein have the following advantages:

1) The synthetic approach used in all embodiments is very short with regard to the number of synthetic steps as compared to the commonly used gluconolactone approach. This synthetic step brevity has been achieved through a redox economic synthetic strategy (i.e., by not changing the oxidation state at C1).

2) In embodiments where a boronic ester is used as the protecting group, or where no protecting group is used at all, the overall process of the synthesis of β-C-arylglucoside from then parent sugar glucose is very reaction-step and process-operation (such as work-up steps) efficient as compared to the relevant art on β-C-arylglucoside synthesis.

3) This arylation approach provides the desired β-anomer of the C-arylglucosides in a stereoselective manner (i.e., relative to the desired β-anomer, a smaller amount of the undesired α-anomer is detected in arylation product mixtures) or in a highly stereoselective manner (i.e., none of the undesired α-anomer is detected in crude product mixtures). This contrasts with the some of the other synthetic approaches (such as the gluconolactone approach, for example) to C-arylglucosides that provides mixtures of α- and β-C-arylglucosides.

4) In some embodiments the arylation reaction provides a 2,4-di-O-protected C-arylglucoside in which the primary C6-O and secondary C3-O positions are not blocked or provides a 2,3,4-tri-O-protected C-arylglucoside in which the

43

C6-O hydroxyl is not blocked. This presents an opportunity to convert these compounds to C-arylglucoside prodrugs, such as those possessing C6-O esters and carbonates. This is more difficult to achieve using other methods in the arts.

5) In preferred embodiments, the arylating reagents comprise aluminum (i.e., $M^1$=Al) which is a highly abundant metal in nature, is cheap and is a non-toxic metal. Moreover, the aluminum hydroxides formed during aqueous work-up are of low toxicity making them environmentally friendly.

6) By varying the aryl group component of the arylating reagent, different, C-arylglucosides can be accessed. The arylation methodology has been demonstrated with a range of different aryl groups, including some that are constituents of the known SGLT2 inhibitors dapagliflozin and canagliflozin.

7) The arylating reagent is fine tunable and can be readily prepared from commercially available or easily accessible starting materials. Some improvements in atom economy and/or cost economy can be achieved by the use of dummy ligands, such as halides.

EXAMPLES

The symbols, conventions and abbreviations used in the above specification and in the following examples are consistent with those used in the contemporary scientific literature, for example, *Journal of the American Chemical Society* and *The ACS Style Guide: effective communication of scientific information,* 3rd ed.; Coghill, A. M. and Garson, L. R. ed.; Washington, D.C., Oxford University Press, New York Oxford, 2006. Besides during aqueous work-ups, all of the below experiments were conducted under strictly dry conditions in an oxygen-free environment, meaning that dried solvents (typically dried over molecular sieves), oven-dried glassware (dried at about 105° C.) and syringes were used under a dry nitrogen atmosphere. Commercially available or in-house prepared solutions of organometallic reagents and $AlCl_3$ were titrated for determination of their concentration prior to use.

Bu$_2$O—di-n-butyl ether
Bu—butyl
t-Bu—tert-butyl
n-BuLi—n-butyllithium
t-BuLi—t-butyllithium
Me—methyl
Et—ethyl
Pr—propyl
Ph—phenyl ($C_6H_5$)
Et$_2$O—diethyl ether
DIBAL—diisobutylaluminum hydride
DCM—dichloromethane
PhCN—benzonitrile
g—gram(s)
mg—milligram(s)
L—liter(s)
mL—milliliter(s)
TBS—tert-butyldimethylsilyl
TBSCl—tert-butyldimethylsilyl chloride
M—molarity
N—normality
MHz—megahertz
mol—mole(s)
mmol—millimole(s)
min—minute(s)
h—hour(s)
TLC—thin layer chromatography
TBDPS—tert-butyldiphenylsilyl
TBDPSCl—tert-butyldiphenylsilyl chloride

44

TES—triethylsilyl
TBAF—tetrabutylammonium fluoride
$R_f$—retention factor
MeOH—methanol
PrOH—isopropanol
PhOMe—anisole
PhMe—toluene
PhCl—chlorobenzene
Pd/C—palladium on carbon
brine—saturated aqueous sodium chloride solution
AcOH—acetic acid
TFA—trifluoroacetic acid
THF—tetrahydrofuran
NMP—N-methylpyrrolidinone
DMSO—dimethylsulfoxide
EtOAc—ethyl acetate
DCM—dichloromethane
DCE—dichloroethane
DMF—N,N-dimethylformamide
atm—atmosphere
HPLC—High performance liquid chromatography The following examples are provided to further illustrate, but not to limit this invention.

Example 1

Synthesis of 1,6-anhydro-2,4-di-O-tert-butyldiphenylsilyl-β-D-glucopyranose (II″)

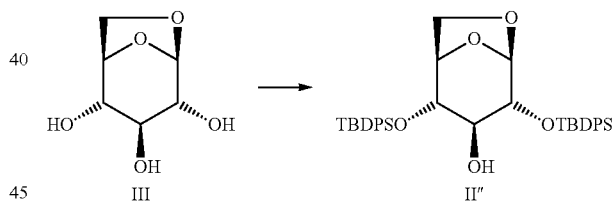

To a suspension solution of 1,6-anhydro-β-D-glucopyranose (1.83 g, 11.3 mmol) and imidazole (3.07 g, 45.2 mmol) in THF (10 mL) at 0° C. was added dropwise a solution of TBDPSCl (11.6 mL, 45.2 mmol) in THF (10 mL). After the 1,6-anhydro-β-D-glucopyranose was consumed, water (10 mL) was added and the mixture was extracted twice with EtOAc (20 mL each), washed with brine (10 mL), dried (Na$_2$SO$_4$) and concentrated. Column chromatography (eluting with 1:20 EtOAc/n-heptane) afforded 2,4-di-O-tert-butyldiphenylsilyl-1,6-anhydro-β-D-glucopyranose (5.89 g, 81%).

$^1$H NMR (400 MHz, CDCl$_3$) δ 7.82-7.70 (m, 8H), 7.49-7.36 (m, 12H), 5.17 (s, 1H), 4.22 (d, J=4.8 Hz, 1H), 3.88-3.85 (m, 1H), 3.583-3.579 (m, 1H), 3.492-3.486 (m, 1H), 3.47-3.45 (m, 1H), 3.30 (dd, J=7.4, 5.4 Hz, 1H), 1.71 (d, J=6.0 Hz, 1H), 1.142 (s, 9H), 1.139 (s, 9H); $^{13}$C NMR (100 MHz, CDCl$_3$) δ 135.89 (CH×2), 135.87 (CH×2), 135.85 (CH×2), 135.83 (CH×2), 133.8 (C), 133.5 (C), 133.3 (C), 133.2 (C), 129.94 (CH), 129.92 (CH), 129.90 (CH), 129.88 (CH), 127.84 (CH$_2$×2), 127.82 (CH$_2$×2), 127.77 (CH$_2$×4), 102.4

(CH), 76.9 (CH), 75.3 (CH), 73.9 (CH), 73.5 (CH), 65.4 (CH$_2$), 27.0 (CH$_3$×6), 19.3 (C×2).

Example 2

2,4-di-O-tert-butyldiphenylsilyl-1-C-phenyl-β-D-glucopyranoside (IVa″)

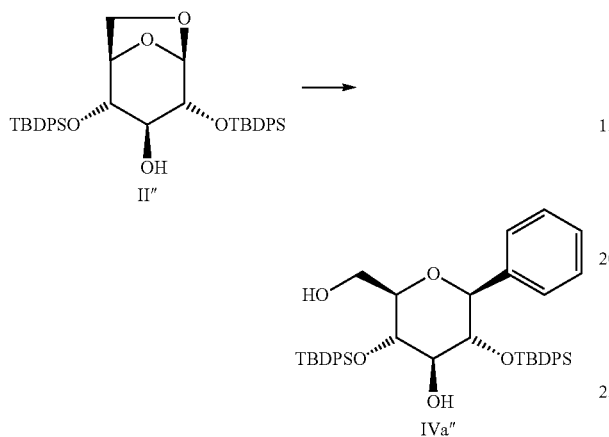

AlCl$_3$ (4.0 mL, 2.0 mmol, 0.5 M solution in THF) and phenylmagnesium bromide (1.9 mL, 5.0 mmol, 2.6 M solution in Et$_2$O) were combined to give a black solution. After being stirred at ambient temperature for 1 hour, the solvent was evaporated under vacuum (50 torr), followed by addition of PhMe (6.0 mL). To a solution of 1,6-anhydro-2,4-di-O-tert-butyldiphenylsilyl-β-D-glucopyranose (0.64 g, 1.0 mmol) in PhMe (3.0 mL) at ambient temperature was added phenylmagnesium bromide (0.4 mL, 1.0 mmol, 2.6 M solution in Et$_2$O) and after stirring for about 5 min the mixture was then partially concentrated under reduced pressure (50 torr) to remove the Et$_2$O. The remaining PhMe solution of 1,6-anhydro-2,4-di-O-tert-butyldiphenylsilyl-β-D-glucopyranose was added to the previously prepared aluminum mixture, followed by dilution with PhMe (1.0 mL) The mixture was heated under gentle reflux for 27 hours. After cooling to ambient temperature, THF (20 mL) followed by 10% aqueous NaOH (2 mL), followed by diatomaceous earth (2 g) followed by Na$_2$SO$_4$ (5 g) were added to the product mixture and the resulting suspension was filtered. The filtrate was concentrated to give an orange oil that was purified by silica gel column chromatography (eluting with 1:6 EtOAc/n-heptane) to give the product 2,4-di-O-tert-butyldiphenylsilyl-1-C-phenyl-β-D-glucopyranoside (0.46 g, 64%) as a colorless to light yellow oil.

$^1$H NMR (400 MHz, CDCl$_3$) δ 7.67 (dd, J=8.2, 1.4 Hz, 2H), 7.57 (dd, J=8.0, 1.6 Hz, 2H), 7.46-7.33 (m, 12H), 7.31-7.24 (m, 7H), 7.17-7.14 (m, 2H), 4.28 (d, J=9.6 Hz, 1H), 3.89 (ddd, J=11.4, 8.2, 2.8 Hz, 1H), 3.85-3.79 (m, 1H), 3.61 (ddd, J=9.3, 6.3, 2.7 Hz, 1H), 3.53-3.48 (m, 2H), 3.41 (dd, J=9.4, 8.6 Hz, 1H), 1.77 (dd, J=8.0, 5.2 Hz, 1H, OH), 1.23 (d, J=4.8 Hz, 1H, OH), 1.01 (s, 9H), 0.62 (s, 9H); $^{13}$C NMR (100 MHz, CDCl$_3$) δ 138.6 (C), 136.6 (CH×2), 136.2 (CH×2), 135.5 (C), 135.3 (CH×2), 135.0 (CH×2), 134.9 (C), 132.9 (C), 132.0 (C), 129.8 (CH), 129.7 (CH), 129.4 (CH), 129.3 (CH), 128.7 (CH×2), 128.5 (CH), 128.4 (CH×2), 127.6 (CH×6), 127.3 (CH×2), 82.9 (CH), 80.6 (CH), 79.4 (CH), 76.5 (CH), 72.9 (CH), 62.8 (CH$_2$), 27.3 (CH$_3$×3), 26.7 (CH$_3$×3), 19.7 (C), 19.2 (C); ESI QT of calculated for [C$_{44}$H$_{52}$NaO$_5$Si$_2$$^+$]= 739.32455, found 739.32450.

Example 3

Synthesis of 1-C-phenyl-β-D-glucopyranoside (Ia)

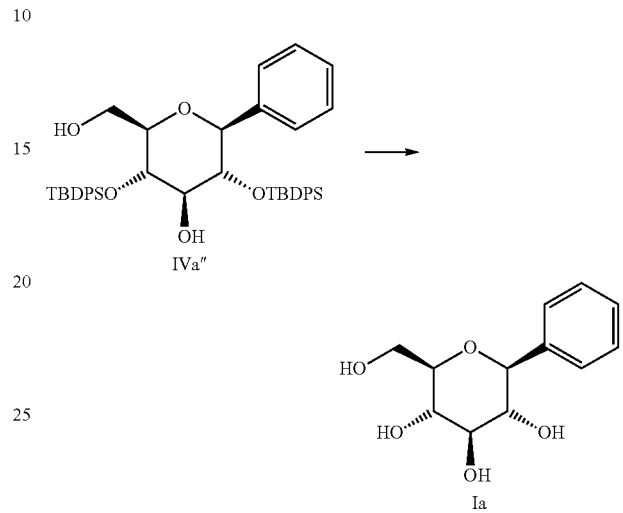

To a solution of 2,4-di-O-tert-butyldiphenylsilyl-1-C-phenyl-β-D-glucopyranoside (1 g, 1.4 mmol) and THF (5 mL) at ambient temperature was added TBAF (14 mL, 14 mmol, 1.0 M in THF). After the starting material was consumed, the reaction was added to a mixture of Dowex® 50WX8-400 ion exchange resin (8 g), CaCO$_3$ (3 g) and MeOH (10 mL). After stirring at ambient temperature for 1 hour, the reaction mixture was filtered and washed with MeOH (20 mL). The filtrate was concentrated and the resulting residue was purified by column chromatography (eluting with 1:10 MeOH/DCM) affording 1-C-phenyl-β-D-glucoside (0.24 g, 72%).

$^1$H NMR (400 MHz, CD$_3$OD) δ 7.46-7.43 (m, 2H), 7.37-7.28 (m, 3H), 4.16 (d, J=9.2 Hz, 1H), 3.92-3.89 (m, 1H), 3.75-3.70 (m, 1H), 3.53-3.38 (m, 4H); $^{13}$C NMR (100 MHz, CD$_3$OD) δ 139.5 (C), 127.7 (CH×2), 127.62 (CH×2), 127.55 (CH), 82.3 (CH), 80.8 (CH), 78.4 (CH), 75.0 (CH), 70.6 (CH), 61.8 (CH$_2$); LCMS (ESI) m/z 258 (100, [M+NH$_4$]$^+$), 263 (69, [M+Na]$^+$), 503 (25, [2M+Na]$^+$).

Example 4

Synthesis of 2,4-di-O-tert-butyldiphenylsilyl-1-C-phenyl-β-D-glucopyranoside (IVa″)

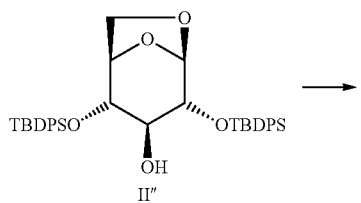

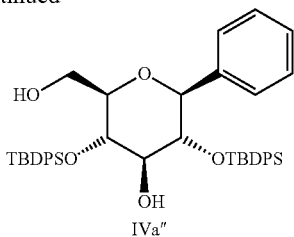

A mixture of AlCl$_3$ (2.4 mL, 1.2 mmol, 0.5 M solution in THF) and phenylmagnesium bromide (1.2 mL, 3.0 mmol, 2.6 M solution in Et$_2$O) were stirred (a black solution) at ambient temperature for 1 hour. To a solution of 1,6-anhydro-2,4-di-O-tert-butyldiphenylsilyl-β-D-glucopyranose (0.63 g, 1.0 mmol) in PhOMe (3.0 mL) at ambient temperature was added phenylmagnesium bromide (0.38 mL, 1.0 mmol, 2.6 M solution in Et$_2$O) and after stirring for about 5 min the resultant solution was then added into the previously prepared aluminum mixture via syringe, followed by additional PhOMe (2.0 mL) that was used to rinse the flask. The mixture was concentrated under reduced pressure (50 torr) at 60-70° C. (external bath temperature) to remove the low-boiling point ethereal solvents (but the PhOMe was not removed). The remaining mixture was heated at 130° C. (external bath temperature) for 22 hours at which time HPLC assay analysis indicated a 68% yield of 2,4-di-O-tert-butyldiphenylsilyl-1-C-phenyl-β-D-glucopyranoside.

Example 5

Synthesis of 2,4-di-O-tert-butyldiphenylsilyl-1-C-phenyl-β-D-glucopyranoside (IVa″)

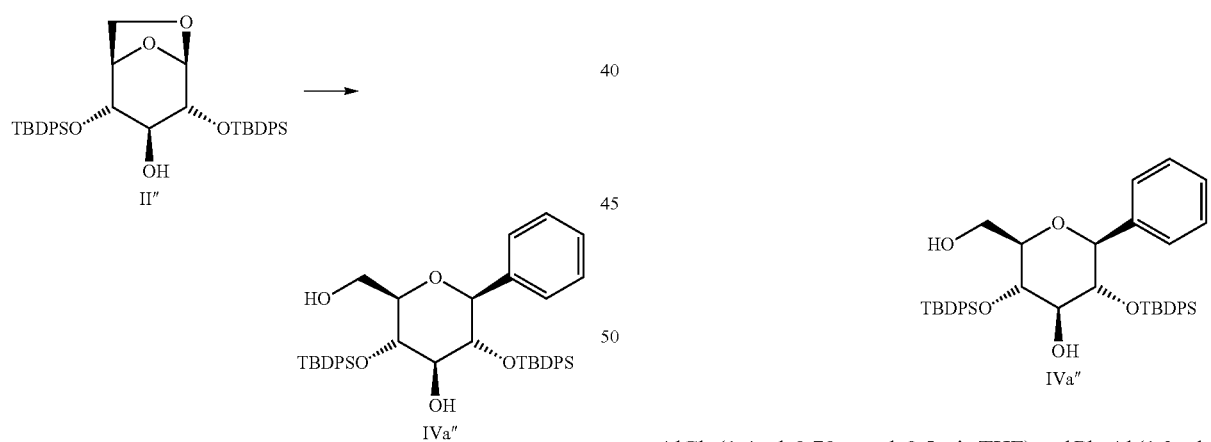

AlCl$_3$ (0.60 ml, 0.30 mmol, 0.5 M in THF) and Ph$_3$Al (1.7 ml, 1.7 mmol, 1.0 M in Bu$_2$O) were mixed at ambient temperature to give a black-colored solution. To this mixture was added a solution of 1,6-anhydro-2,4-di-O-tert-butyldiphenyl-silyl-β-D-glucopyranose (0.64 g, 1.0 mmol) in PhOMe (4.0 mL) at ambient temperature. The mixture was concentrated under reduced pressure (50 torr) at 60° C. (external bath temperature) to remove the low-boiling ethereal solvent. The remaining mixture (comprising PhOMe/Bu$_2$O as solvent) was heated at 130° C. (external bath temperature) for 6 hours at which time HPLC assay analysis indicated a 71% yield of 2,4-di-O-tert-butyldiphenylsilyl-1-C-phenyl-β-D-glucopyranoside. After cooling to ambient temperature, an aliquot (0.5 mL) of the reaction product mixture was added into a solution of iodine (0.25 g, 0.98 mmol) in THF (5.0 mL). The black-colored mixture was stirred at ambient temperature for 15 min at which time HPLC assay analysis indicated a 43% recovery of iodobenzene and a 52% recovery of benzene. Another aliquot (0.5 mL) of the reaction product mixture was added into a solution of iodine (0.25 g, 0.98 mmol) and LiCl (5.0 mL, 0.5 M in THF). The black-colored mixture was stirred at ambient temperature for 2 hours at which time HPLC assay analysis indicated a 59% recovery of iodobenzene and a 33% recovery of benzene.

Example 6

Synthesis of 2,4-di-O-tert-butyldiphenylsilyl-1-C-phenyl-β-D-glucopyranoside (IVa″)

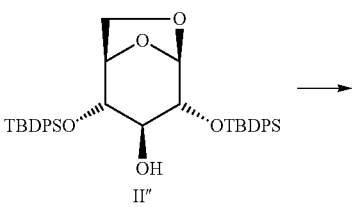

AlCl$_3$ (1.4 ml, 0.70 mmol, 0.5 M in THF) and Ph$_3$Al (1.3 ml, 1.3 mmol, 1.0 M in Bu$_2$O) were mixed at ambient temperature to give a light brown-colored solution. To a solution of 1,6-anhydro-2,4-di-O-tert-butyldiphenylsilyl-β-D-glucopyranose (0.64 g, 1.0 mmol) in PhOMe (4.0 mL) was added n-BuLi (0.42 mL, 1.0 mmol, 2.4 M in hexane) at ambient temperature and after stirring for about 5 min the resulting mixture was then added to the above prepared aluminum mixture. The mixture was concentrated under reduced pressure (50 torr) at 60° C. (external bath temperature) to remove the low-boiling ethereal solvent. The remaining mixture (comprising PhOMe/Bu$_2$O as solvent) was heated at 130° C. (external bath temperature) for 3 hours at which time HPLC assay indicated a 76% yield of 2,4-di-O-tert-butyldiphenyl-silyl-1-C-phenyl-β-D-glucopyranoside.

Example 7

Synthesis of 2,4-di-O-tert-butyldiphenylsilyl-1-C-phenyl-β-D-glucopyranoside (IVa")

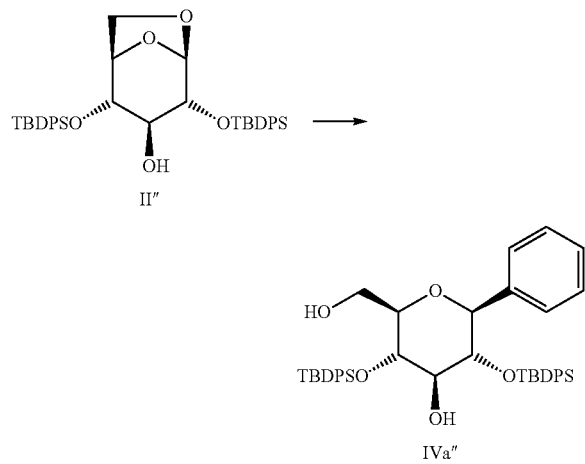

To a 0.5 M THF solution of AlCl₃ (12 mL, 6 mmol) at 0° C. was added dropwise a 2 M Bu₂O solution of PhLi (6 mL, 12 mmol). The mixture was warmed to room temperature, and then after one hour the mixture was heated to 60° C. A PhMe (15 mL) solution of 1,6-anhydro-2,4-di-O-tert-butyldiphenylsilyl-β-D-glucopyranose (2.54 g, 4 mmol) was added dropwise and the mixture was then heated under reflux. After the 1,6-anhydro-2,4-di-O-tert-butyldiphenylsilyl-β-D-glucopyranose had been consumed, the product mixture was cooled to 0° C. and was poured onto an ice-water mixture (50 mL). The mixture was extracted with EtOAc (20 mL), washed with 1 N HCl (10 mL) and brine (10 mL), dried (Na₂SO₄) and concentrated. Column chromatography (eluting with 1:10 EtOAc/n-heptane) of the resulting residue afforded 2,4-di-O-tert-butyldiphenylsilyl-1-C-phenyl-β-D-glucopyranoside (1.17 g, 41%).

Example 8

Synthesis of 2,4-di-O-tert-butyldiphenylsilyl-1-C-(2,4,6-trimethylphenyl)-1-β-D-glucopyranoside (IVb")

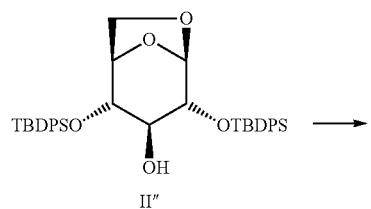

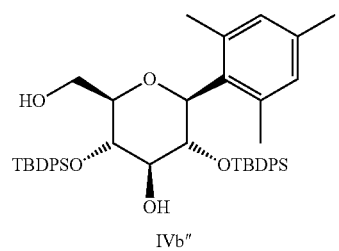

PhOMe (6 mL), AlCl₃ (0.5 M in THF, 4.0 mL, 2.0 mmol) and 2,4,6-trimethylphenylmagnesium bromide (0.8 M in THF, 6.25 mL, 5.0 mmol) were mixed at ambient temperature to give a yellow solution which was stirred at ambient temperature for 1 hour. To a solution of 1,6-anhydro-2,4-di-O-tert-butyldiphenylsilyl-β-D-glucopyranose (0.64 g, 1.0 mmol) in PhOMe (3.0 mL) at ambient temperature was added phenylmagnesium bromide (0.38 mL, 1.0 mmol, 2.6 M solution in Et₂O). After stirring for about 5 min the solution was then added into the above prepared aluminum mixture via syringe, followed by additional PhOMe (1.0 mL) to rinse the flask. The mixture was concentrated under reduced pressure (50 torr) at 60° C. (external bath temperature) to remove low-boiling point ethereal solvents. The remaining mixture was heated at 150° C. (external bath temperature) for 16 hours at which time HPLC assay analysis indicated a 67% yield of 2,4-di-O-tert-butyldiphenylsilyl-1-C-(2,4,6-trimethylphenyl)-β-D-glucopyranoside. After cooling to ambient temperature the product mixture was treated with 10% aqueous NaOH (1 mL), THF (10 mL) and diatomaceous earth at ambient temperature, and then the mixture was filtered and the filter cake was washed with THF. The combined filtrates were concentrated and the crude product was purified by column chromatography (eluting with 1:10 EtOAc/n-heptane) affording 2,4-di-O-tert-butyldiphenylsilyl-1-C-(2,4,6-trimethylphenyl)-1-β-D-glucopyranoside (494 mg, 65%).

$^1$H NMR (400 MHz, CDCl₃) δ 7.56-7.54 (m, 2H), 7.47-7.45 (m, 2H), 7.34-7.22 (m, 12H), 7.21-7.13 (m, 4H), 6.74 (d, J=0.8 Hz, 1H), 6.66 (d, J=0.8 Hz, 1H), 4.74-4.69 (m, 1H), 3.80 (ddd, J=11.2, 8.4, 2.6 Hz, 1H), 3.68-3.65 (m, 2H), 3.48 (ddd, J=9.2, 6.4, 2.6 Hz, 1H), 3.41-3.36 (m, 1H), 3.30-3.25 (m, 1H), 2.37 (s, 3H), 2.17 (s, 3H), 1.77 (s, 3H), 1.71 (dd, J=8.0, 5.2 Hz, 1H, OH), 0.91 (s, 9H), 0.53 (s, 9H); $^{13}$C NMR (100 MHz, CDCl₃) δ 137.8 (C), 137.4 (C), 137.3 (C), 136.5 (CH×2), 136.1 (CH×2), 135.6 (C), 135.2 (CH×2), 135.0 (C), 134.9 (CH×2), 133.0 (C), 131.8 (C), 131.3 (C), 130.9 (CH), 129.63 (CH), 129.60 (CH), 129.3 (CH), 129.14 (CH), 129.09 (CH), 127.54 (CH×2), 127.48 (CH×4), 127.3 (CH×2), 80.7 (CH), 80.0 (CH), 78.2 (CH), 74.3 (CH), 73.0 (CH), 63.1 (CH₂), 27.2 (CH₃×3), 26.4 (CH₃×3), 21.8 (CH₃), 20.8 (CH₃), 20.1 (CH₃), 19.6 (C), 19.0 (C); LCMS (ESI) m/z 776 (100,

[M+NH$_4$]$^+$), 781 (3, [M+Na]$^+$); ESI QT of calculated for [C$_{47}$H$_{58}$NaO$_5$Si$_2$$^+$]=781.3715, found 781.3712.

Example 9

Synthesis of 2,4-di-O-tert-butyldiphenylsilyl-1-C-(4-methylphenyl)-1-β-D-glucopyranoside (IVc″)

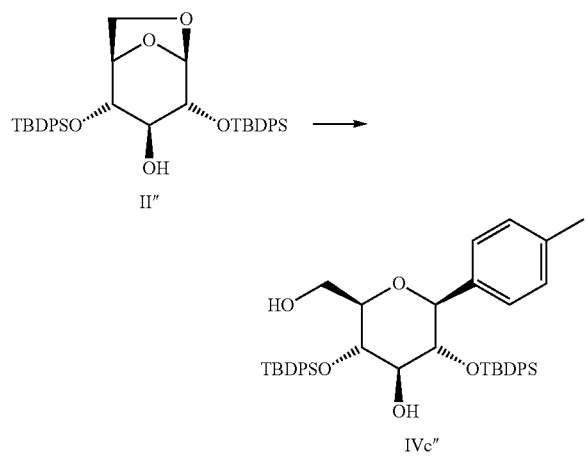

PhOMe (6 mL), AlCl$_3$ (0.5 M in THF, 4.0 mL, 2.0 mmol) and 4-methylphenylmagnesium bromide (5.0 mL, 5.0 mmol, 1.0 M in THF) were mixed at ambient temperature to give a black solution, which was then stirred at ambient temperature for 1 hour. To a solution of 1,6-anhydro-2,4-di-O-tert-butyl-diphenylsilyl-β-D-glucopyranose (0.64 g, 1.0 mmol) in PhOMe (3.0 mL) at ambient temperature was added phenylmagnesium bromide (0.38 mL, 1.0 mmol, 2.6 M solution in Et$_2$O) and after stirring for about 5 min the mixture was added to the above prepared aluminum mixture via syringe, followed by additional PhOMe (1.0 mL) to rinse the flask. The mixture was concentrated under reduced pressure (50 torr) at 60° C. (external bath temperature) to remove low-boiling point ethereal solvents. The remaining mixture was heated at 130° C. (external bath temperature) for 26 hours at which time HPLC assay analysis showed a 59% yield of 2,4-di-O-tert-butyldiphenylsilyl-1-C-(4-methylphenyl)-β-D-glucopyranoside. After cooling to ambient temperature, the reaction was treated with 10% aqueous NaOH (1 mL), THF (10 mL) and diatomaceous earth at ambient temperature. The mixture was filtered and the filter cake was washed with THF. The combined filtrates were concentrated and the crude product was purified by column chromatography (eluting with 1:10 EtOAc/n-heptane) affording 2,4-di-O-tert-butyldiphenylsilyl-1-C-(4-methylphenyl)-1-β-D-glucopyranoside (405 mg, 55%).

$^1$H NMR (400 MHz, CDCl$_3$) δ 7.66 (d, J=6.8 Hz, 2H), 7.57 (d, J=6.8 Hz, 2H), 7.45-7.32 (m, 12H), 7.30-7.24 (m, 4H), 7.07 (d, J=7.6 Hz, 2H), 7.03 (d, J=7.6 Hz, 2H), 4.24 (d, J=9.6, 1H), 3.90-3.85 (m, 1H), 3.83-3.77 (m, 1H), 3.62-3.58 (m, 1H), 3.52-3.46 (m, 2H), 3.40 (dd, J=8.8, 8.8 Hz, 1H), 2.34 (s, 3H), 1.77 (dd, J=6.6, 6.6 Hz, 1H, OH), 1.22 (d, J=4.8 Hz, 1H, OH), 1.01 (s, 9H), 0.63 (s, 9H); $^{13}$C NMR (100 MHz, CDCl$_3$) δ 138.2 (C), 136.5 (CH×2), 136.1 (CH×2), 135.5 (C), 135.4 (C), 135.2 (CH×2), 135.0 (CH×2), 134.9 (C), 132.9 (C), 132.1 (C), 129.7 (CH), 129.5 (CH), 129.3 (CH), 129.2 (CH), 128.9 (CH×2), 128.5 (CH×2), 127.53 (CH×4), 127.51 (CH×2), 127.2 (CH×2), 82.6 (CH), 80.4 (CH), 79.4 (CH), 76.3 (CH), 72.9 (CH), 62.8 (CH$_2$), 27.2 (CH$_3$×3), 26.6 (CH$_3$×3), 21.2 (CH$_3$), 19.6 (C), 19.1 (C); LCMS (ESI) m/z 748 (100, [M+NH$_4$]$^+$), 753 (2, [M+Na]$^+$; ESI QT of calculated for [C$_{45}$H$_{54}$NaO$_5$Si$_2$$^+$]=753.3402, found 753.3423.

Example 10

Synthesis of 2,4-di-O-tert-butyldiphenylsilyl-1-C-(4-methoxylphenyl)-1-β-D-glucopyranoside (IVd″)

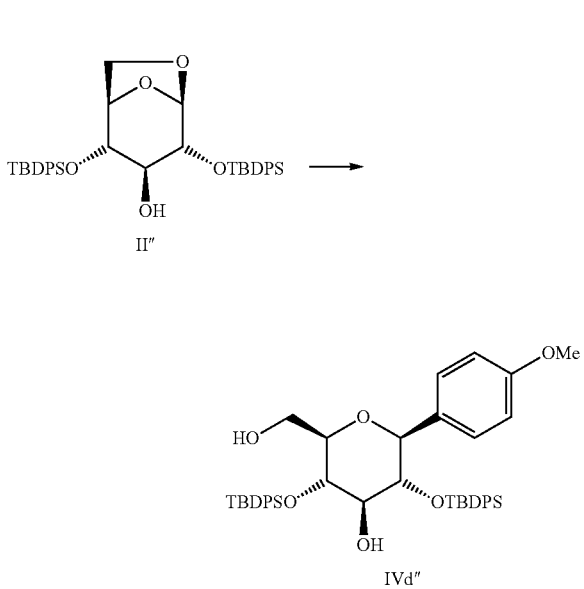

PhOMe (6 mL), AlCl$_3$ (0.5 M in THF, 5.0 mL, 2.5 mmol) and 4-methoxylphenylmagnesium bromide (10.0 mL, 5.0 mmol, 0.5 M in THF) were mixed at ambient temperature to give a black solution, which was stirred at ambient temperature for 1 hour. To a solution of 1,6-anhydro-2,4-di-O-tert-butyldiphenylsilyl-β-D-glucopyranose (0.64 g, 1.0 mmol) in PhOMe (3.0 mL) at ambient temperature was added phenylmagnesium bromide (0.38 mL, 1.0 mmol, 2.6 M solution in Et$_2$O). After stirring for about 5 min the solution was then added to the above prepared aluminum mixture via syringe, followed by additional PhOMe (1.0 mL) to rinse the flask. The mixture was concentrated under reduced pressure (50 torr) at 60° C. (external bath temperature) to remove low-boiling point ethereal solvents. The remaining mixture was heated at 130° C. (external bath temperature) for 8 hours at which time HPLC assay analysis indicated a 54% yield of 2,4-di-O-tert-butyldiphenylsilyl-1-C-(4-methoxyphenyl)-β-D-glucopyranoside. $^1$H NMR (400 MHz, CDCl$_3$) δ 7.67 (d, J=7.2 Hz, 2H), 7.58 (d, J=7.2 Hz, 2H), 7.46-7.34 (m, 13H), 7.30-7.25 (m, 3H), 7.05 (d, J=8.4 Hz, 2H), 6.80 (d, J=8.0 Hz, 2H), 4.24 (d, J=9.6 Hz, 1H), 3.91-3.86 (m, 1H), 3.84-3.78 (m, 1H), 3.81 (s, 3H), 3.62-3.58 (m, 1H), 3.53-3.47 (m, 2H), 3.41 (dd, J=9.9, 9.9 Hz, 1H), 1.77 (dd, J=6.6, 6.6 Hz, 1H, OH), 1.02 (s, 9H), 0.66 (s, 9H); $^{13}$C NMR (100 MHz, CDCl$_3$) δ 159.8 (C), 136.5 (CH×2), 136.2 (CH×2), 135.4 (C), 135.2 (CH×2), 135.0 (CH×2), 134.9 (CH), 132.9 (C), 132.0 (C), 130.8 (C), 129.8 (CH×2), 129.7 (CH), 129.6 (CH), 129.4 (CH), 129.2 (CH), 127.54 (CH×4), 127.53 (CH×2), 127.2 (CH×2), 113.7 (CH×2), 82.3 (CH), 80.4 (CH), 79.4 (CH), 76.3 (CH), 72.9 (CH), 62.8 (CH$_2$), 55.4 (CH$_3$), 27.2 (CH$_3$×3), 26.6 (CH₃×3), 19.6 (C), 19.1 (C); ESI QT of calculated for [C₄₅H₅₄NaO₆Si₂⁺]=769.3351, found 769.3330.

Example 11

Synthesis of 2,4-di-O-tert-butyldiphenylsilyl-1-C-(4-chlorophenyl)-1-β-D-glucopyranoside (IVe″)

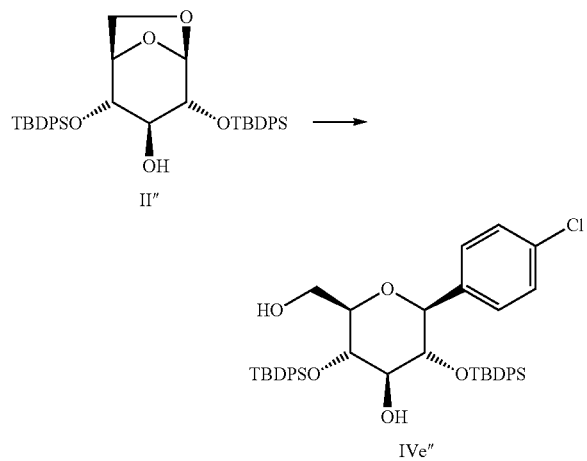

PhOMe (6 mL), AlCl₃ (0.5 M in THF, 4.0 mL, 2.0 mmol) and 4-chlorophenylmagnesium bromide (0.8 M in THF, 6.25 mL, 5.0 mmol) were mixed at ambient temperature to give a black solution, which was stirred at ambient temperature for 1 hour. To a solution of 1,6-anhydro-2,4-di-O-tert-butyldiphenylsilyl-β-D-glucopyranose (0.64 g, 1.0 mmol) in PhOMe (3.0 mL) at ambient temperature was added phenylmagnesium bromide (0.38 mL, 1.0 mmol, 2.6 M solution in Et₂O). After stirring for about 5 min the solution was then added to the above prepared aluminum mixture via syringe, followed by additional PhOMe (1.0 mL) to rinse the flask. The mixture was concentrated under reduced pressure (50 torr) at 60° C. (external bath temperature) to remove low-boiling point ethereal solvents. The remaining mixture was heated at 150° C. (external bath temperature) for 22 hours at which time HPLC assay analysis showed a 47% yield of 2,4-di-O-tert-butyldiphenylsilyl-1-C-(4-chlorophenyl)-β-D-glucopyranoside. After cooling to ambient temperature, the product mixture was treated with 10% aqueous NaOH (1 mL), THF (10 mL) and diatomaceous earth at ambient temperature. The mixture was filtered and the filter cake was washed with THF. The combined filtrates were concentrated and the crude product was purified by column chromatography (eluting with 1:15 EtOAc/n-heptane) providing 2,4-di-O-tert-butyldiphenylsilyl-1-C-(4-chlorophenyl)-1-β-D-glucopyranoside (328 mg, 44%).

¹H NMR (400 MHz, CDCl₃) δ 7.67 (dd, J=8.0, 1.2 Hz, 2H), 7.57 (dd, J=8.0, 1.6 Hz, 2H), 7.44-7.33 (m, 13H), 7.31-7.26 (m, 3H), 7.22-7.20 (m, 2H), 7.05 (dd, J=6.4, 2.0 Hz, 2H), 4.25 (d, J=9.6 Hz, 1H), 3.90-3.79 (m, 2H), 3.60 (ddd, J=9.2, 6.4, 2.6 Hz, 1H), 3.53-3.38 (m, 3H), 1.70 (dd, J=8.0, 5.6 Hz, 1H, OH), 1.01 (s, 9H), 0.67 (s, 9H); ¹³C NMR (100 MHz, CDCl₃) δ 137.0 (C), 136.4 (CH₂×2), 136.1 (CH₂×2), 135.2 (CH₂×2), 135.1 (C), 134.9 (CH₂, ×2), 134.8 (C), 134.2 (C), 132.7 (C), 131.9 (C), 130.0 (CH×2), 129.73 (CH), 129.67 (CH), 129.4 (CH), 129.3 (CH), 128.4 (CH×2), 127.6 (CH×6), 127.3 (CH× 2), 82.1 (CH), 80.5 (CH), 79.3 (CH), 76.4 (CH), 72.7 (CH), 62.7 (CH₂), 27.2 (CH₃×3), 26.6 (CH₃×3), 19.6 (C), 19.1 (C);

LCMS (ESI) m/z 768 (100, [M+NH₄]⁺), 773 (5, [M+Na]⁺); ESI QT of calculated for [C₄₄H₅₁ClNaO₅Si₂⁺]=773.2856, found 773.2852.

Example 12

Synthesis of 2,4-di-O-tert-butyldiphenylsilyl-1-C-(4-fluorophenyl)-1-β-D-glucopyranoside (IVf″)

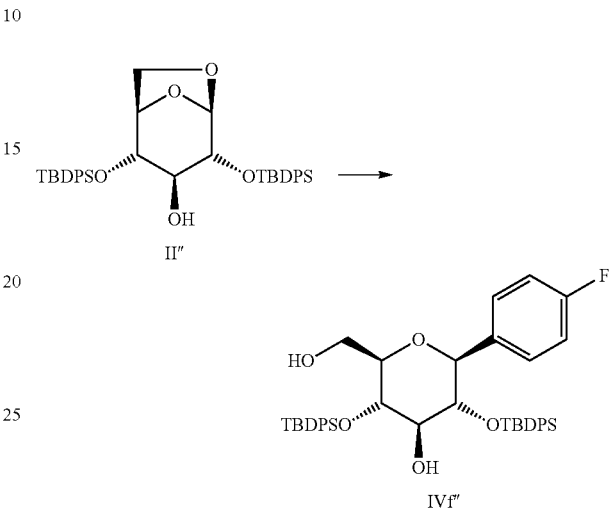

PhOMe (6 mL), AlCl₃ (0.5 M in THF, 4.0 mL, 2.0 mmol) and 4-fluorophenylmagnesium bromide (1.9 M in THF, 2.6 mL, 5.0 mmol) were mixed at ambient temperature to give a black solution, which was stirred at ambient temperature for 1 hour. To a solution of 1,6-anhydro-2,4-di-O-tert-butyldiphenylsilyl-β-D-glucopyranose (0.64 g, 1.0 mmol) in PhOMe (3.0 mL) at ambient temperature was added phenylmagnesium bromide (0.38 mL, 1.0 mmol, 2.6 M solution in Et₂O) and the mixture was stir for about 5 min. The solution was then added into the above prepared aluminum mixture via syringe, followed by additional PhOMe (1.0 mL) to rinse the flask. The mixture was concentrated under reduced pressure (50 torr) at 60° C. (external bath temperature) to remove low-boiling point ethereal solvents. The remaining mixture was heated at 150° C. (external bath temperature) for 6 hours at which time HPLC assay analysis indicated a 56% yield of 2,4-di-O-tert-butyldiphenylsilyl-1-C-(4-fluorophenyl)-β-D-glucopyranoside. After cooling to ambient temperature, the product mixture was treated with 10% aqueous NaOH (1 mL), THF (10 mL) and diatomaceous earth at ambient temperature, then the mixture was filtered and the filter cake was washed with THF. The combined filtrates were concentrated and the crude product was purified by column chromatography (eluting with 1:20 EtOAc/n-heptane) affording 2,4-di-O-tert-butyldiphenylsilyl-1-C-(4-fluorophenyl)-1-β-D-glucopyranoside (395 mg, 54%).

¹H NMR (400 MHz, CDCl₃) δ 7.67 (d, J=7.2 Hz, 2H), 7.57 (d, J=7.2 Hz, 2H), 7.44-7.33 (m, 12H), 7.31-7.25 (m, 4H), 7.09 (dd, J=6.6, 6.6 Hz, 2H), 6.93 (dd, J=8.6, 8.6 Hz, 2H), 4.26 (d, J=10.0 Hz, 1H), 3.91-3.79 (m, 2H), 3.62-3.58 (m, 1H), 3.54-3.38 (m, 3H), 1.70 (dd, J=6.6, 6.6 Hz, 1H, OH), 1.01 (s, 9H), 0.66 (s, 9H); ¹³C NMR (100 MHz, CDCl₃) δ 162.8 (d, J=245 Hz, C), 136.4 (CH×2), 136.2 (CH×2), 135.21 (CH×2), 135.20 (C), 134.9 (CH×2), 134.8 (C), 134.4 (d, J=3.1 Hz, C), 132.8 (C), 131.9 (C), 130.3 (d, J=8.1 Hz, CH×2), 129.73 (CH), 129.68 (CH), 129.4 (CH), 129.3 (CH), 127.58 (CH×2), 127.57 (CH×4), 127.3 (CH×2), 115.1 (d,

J=21.2 Hz, CH×2), 82.1 (CH), 80.5 (CH), 79.3 (CH), 76.4 (CH), 72.8 (CH), 62.8 (CH$_2$), 27.2 (CH$_3$×3), 26.6 (CH$_3$×3), 19.6 (C), 19.1 (C); ESI QT of calculated for [C$_{44}$H$_{51}$FNaO$_5$Si$_2^+$]=757.3151, found 757.3131.

Example 13

Synthesis of 2,4-di-O-tert-butyldiphenylsilyl-1-C-(2-furyl)-1-β-D-glucopyranoside (IVg″)

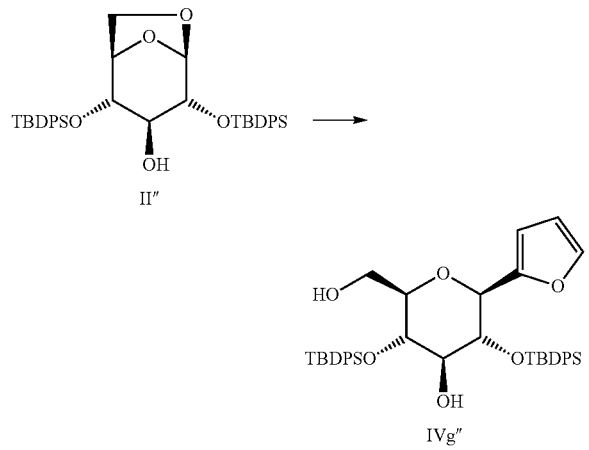

To a chilled (−76° C.) solution of furan (2.5 mL, 34.3 mmol) in THF (21.5 mL) was adding n-BuLi (21.5 mL, 34.3 mmol, 1.6 M in hexane). The mixture was stirred for 1 hour and was then warmed to ambient temperature. The concentration was determined to be 0.5 M by titration. PhOMe (6 mL), AlCl$_3$ (0.5 M in THF, 4.0 mL, 2.0 mmol) and the above prepared 2-furyllithium (10 mL, 5 mmol, 0.5 M in THF) were mixed at ambient temperature to give a black solution, which was stirred at ambient temperature for 1 hour. To a solution of 1,6-anhydro-2,4-di-O-tert-butyldiphenylsilyl-β-D-glucopyranose (0.64 g, 1.0 mmol) in PhOMe (3.0 mL) at ambient temperature was added phenylmagnesium bromide (0.38 mL, 1.0 mmol, 2.6 M solution in Et$_2$O). After stirring for about 5 min the solution was then added into the above prepared aluminum mixture via syringe, followed by additional PhOMe (1.0 mL) to rinse the flask. The mixture was concentrated under reduced pressure (50 torr) at 60° C. (external bath temperature) to remove low-boiling point ethereal solvents. The remaining mixture was heated at 130° C. (external bath temperature) for 16 hours at which time HPLC assay analysis indicated a 78% yield of 2,4-di-O-tert-butyldiphenylsilyl-1-C-(2-furanyl)-β-D-glucopyranoside. After cooling to ambient temperature, the reaction was treated with 10% aqueous NaOH (1 mL), THF (10 mL) and diatomaceous earth at ambient temperature, then the mixture was filtered and the filter cake was washed with THF. The combined filtrates were concentrated and the crude product was purified by column chromatography (eluting with 1:15 EtOAc/n-heptane) affording 2,4-di-O-tert-butyldiphenylsilyl-1-C-(2-furyl)-1-β-D-glucopyranoside (482 mg, 68%).

$^1$H NMR (400 MHz, CDCl$_3$) δ 7.68-7.67 (m, 2H), 7.58-7.56 (m, 2H), 7.50-7.48 (m, 2H), 7.45-7.28 (m, 14H), 7.26 (dd, J=1.6, 0.4 Hz, 1H) 6.27 (dd, J=3.4, 1.8 Hz, 1H), 6.13 (dd, J=3.2, 0.4 Hz, 1H), 4.39 (d, J=9.2 Hz, 1H), 3.90 (ddd, J=11.6, 8.4, 2.4 Hz, 1H), 3.80-3.70 (m, 2H), 3.58 (ddd, J=9.2, 6.6, 2.4 Hz, 1H), 3.53-3.47 (m, 1H), 3.39 (dd, J=9.4, 8.2 Hz, 1H), 1.76 (dd, J=8.0, 5.2 Hz, 1H, OH), 1.30 (d, J=4.4 Hz, 1H, OH), 1.01 (s, 9H), 0.76 (s, 9H); $^{13}$C NMR (100 MHz, CDCl$_3$) δ 151.3 (C), 142.2 (CH), 136.3 (CH×2), 136.2 (CH×2), 135.24 (C), 135.20 (CH×2), 135.1 (CH×2), 134.8 (C), 132.6 (C), 132.1 (C), 129.7 (CH), 129.6 (CH), 129.4 (CH), 129.3 (CH), 127.59 (CH×2), 127.58 (CH×2), 127.53 (CH×2), 127.3 (CH×2), 110.4 (CH), 110.1 (CH), 80.3 (CH), 79.4 (CH), 75.3 (CH), 74.2 (CH), 72.6 (CH), 62.7 (CH$_2$), 27.2 (CH$_3$×3), 26.7 (CH$_3$×3), 19.6 (C), 19.1 (C); ESI QT of calculated for [C$_{42}$H$_{50}$NaO$_6$Si$_2^+$]=729.3038, found 729.3027.

Example 14

Synthesis of 2,4-di-O-tert-butyldiphenylsilyl-1-C-(2-thienyl)-1-β-D-glucopyranoside (IVh″)

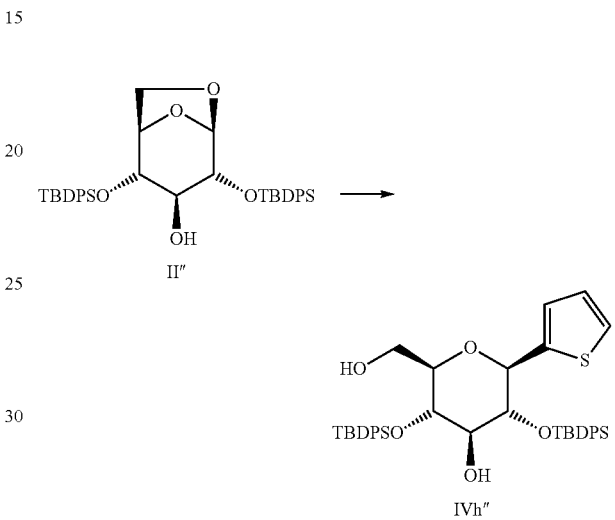

PhOMe (6 mL), AlCl$_3$ (0.5 M in THF, 4.0 mL, 2.0 mmol) and 2-thienylmagnesium bromide (1.0 M in THF, 5.0 mL, 5.0 mmol) were mixed at ambient temperature to give a black solution, which was stirred at ambient temperature for 1 hour. To a solution of 1,6-anhydro-2,4-di-O-tert-butyldiphenylsilyl-β-D-glucopyranose (0.64 g, 1.0 mmol) in PhOMe (3.0 mL) was added phenylmagnesium bromide (0.38 mL, 1.0 mmol, 2.6 M solution in Et$_2$O) at ambient temperature and was stirred for about 5 min. This solution was then added into the above prepared aluminum mixture via syringe, followed by additional PhOMe (1.0 mL) to rinse the flask. The mixture was concentrated under reduced pressure (50 torr) at 60° C. (external bath temperature) to remove low-boiling point ethereal solvents. The remaining mixture was heated at 130° C. (external bath temperature) for 2 hours at which time HPLC assay analysis indicated a 57% yield of 2,4-di-O-tert-butyldiphenylsilyl-1-C-(2-thienyl)-β-D-glucopyranoside. After cooling to ambient temperature, the reaction was treated with 10% aqueous NaOH (1 mL), THF (10 mL) and diatomaceous earth at ambient temperature, then the mixture was filtered and the filter cake was washed with THF. The combined filtrates were concentrated and the crude product was purified by column chromatography (eluting with 1:10 EtOAc/n-heptane) affording 2,4-di-O-tert-butyldiphenylsilyl-1-C-(2-thienyl)-1-β-D-glucopyranoside.

$^1$H NMR (400 MHz, CDCl$_3$) δ 7.70 (dd, J=8.0, 1.2 Hz, 2H), 7.59 (dd, J=8.0, 1.2 Hz, 2H), 7.51-7.30 (m, 16H), 7.26-7.24 (m, 1H), 6.96-6.94 (m, 2H), 4.62 (d, J=9.6 Hz, 1H), 3.93 (dd, J=11.6, 2.0 Hz, 1H), 3.82 (ddd, J=10.2, 6.6, 1.8 Hz, 1H), 3.64 (ddd, J=9.3, 6.3, 2.7 Hz, 1H), 3.57-3.51 (m, 2H), 3.45 (dd, J=9.0, 9.0 Hz, 1H), 1.05 (s, 9H), 0.75 (s, 9H); $^{13}$C NMR (100 MHz, CDCl$_3$) δ 141.5 (C), 136.5 (CH×2), 136.2 (CH×2), 135.5 (C), 135.2 (CH×2), 135.0 (CH×2), 134.8 (C), 132.8 (C), 132.0 (C), 129.8 (CH), 129.7 (CH), 129.4 (CH), 129.3 (CH), 127.63 (CH$_2$×2), 127.61 (CH$_2$×4), 127.34 (C), 127.33 (CH×2), 126.5 (CH), 125.7 (CH), 80.6 (CH), 79.4 (CH), 77.9 (CH), 77.2 (CH), 72.6 (CH), 62.7 (CH$_2$), 27.2 (CH$_3$×3), 26.6 (CH$_3$×3), 19.6 (C), 19.2 (C); LCMS (ESI) m/z 740 (100, [M+NH$_4$]$^+$), 745 (5, [M+Na]$^+$); ESI QT of calculated for [C$_{42}$H$_{50}$NaO$_5$SSi$_2$$^+$]=745.2810, found 745.2808.

Example 15

Synthesis of 2,4-di-O-tert-butyldiphenylsilyl-1-C-phenyl-β-D-glucopyranoside (IVa")

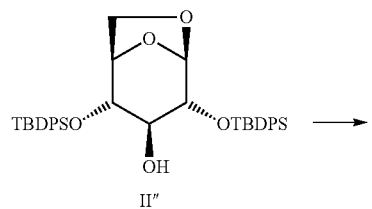

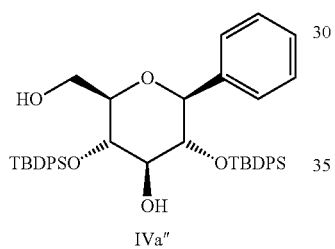

Pentafluorophenol (0.18 g, 1.0 mmol), Ph$_3$Al (2.0 ml, 2.0 mmol, 1.0 M in Bu$_2$O) and PhOMe (1.0 mL) were mixed at ambient temperature to give a light yellow clear solution. To this mixture was then added a solution of 1,6-anhydro-2,4-di-O-tert-butyldiphenylsilyl-β-D-glucopyranose (0.64 g, 1.0 mmol) in PhOMe (4.0 mL). The mixture was heated at 130° C. (external bath temperature) for 12 hours at which time HPLC assay analysis indicated a 73% yield of 2,4-di-O-tert-butyldiphenylsilyl-1-C-phenyl-β-D-glucopyranoside.

Example 16

Synthesis of 2,4-di-O-tert-butyldiphenylsilyl-1-C-phenyl-β-D-glucopyranoside (IVa")

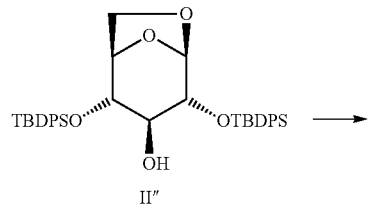

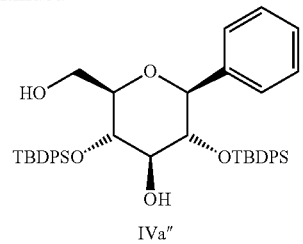

AlCl$_3$ (2.4 ml, 1.2 mmol, 0.5 M in THF), phenylmagnesium bromide (0.73 mL, 1.9 mmol, 2.6 M in Et$_2$O) and t-BuLi (0.50 mL, 0.95 mmol, 1.9 M in pentane) were combined at −40° C. to give a black solution, which was then allowed to warm to ambient temperature. After being stirred at ambient temperature for 1 hour, the solvent was evaporated under vacuum (50 torr), followed by addition of PhMe (5.0 mL). To a solution of 1,6-anhydro-2,4-di-O-tert-butyldiphenylsilyl-β-D-glucopyranose (364 mg, 0.57 mmol) in PhMe (3.0 mL) was added phenylmagnesium bromide (0.22 mL, 0.57 mmol, 2.6 M in Et$_2$O) and the mixture was then partially concentrated under reduced pressure (50 torr) to remove the Et$_2$O solvent. The remaining PhMe solution of 1,6-anhydro-2,4-di-O-tert-butyldiphenylsilyl-β-D-glucopyranose was added to the previously prepared aluminum mixture, followed by dilution with PhMe (1.0 mL). The reaction mixture was heated to gentle reflux for 30 hours at which time HPLC assay analysis indicated a 20% yield of 2,4-di-O-tert-butyldiphenylsilyl-1-C-phenyl-β-D-glucopyranoside.

Example 17

Synthesis of 1,6-anhydro-2,3,4-tri-O-tert-butyldimethylsilyl-β-D-glucopyranose (II"") and 1,6-anhydro-2,4-di-O-tert-butyldimethylsilyl-β-D-glucopyranose (II')

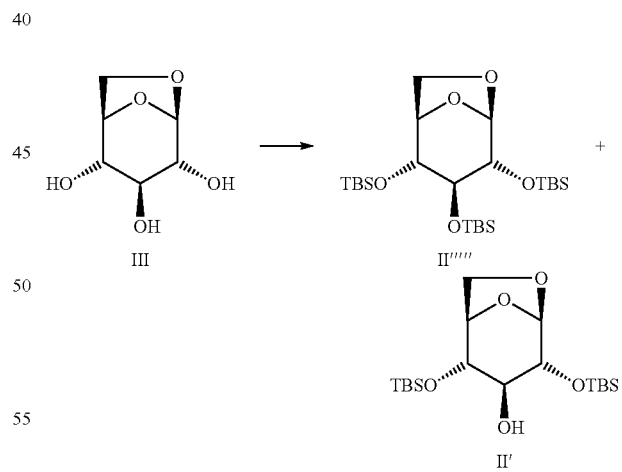

To a suspension solution of 1,6-anhydro-β-D-glucopyranose (5.0 g, 30.8 mmol) and imidazole (14.7 g, 216 mmol) in THF (40 mL) at 0° C. was added dropwise a solution of TBSCl (23.2 g, 154 mmol) in THF (10 mL), and the mixture was stirred at ambient temperature overnight. After 1,6-anhydro-β-D-glucopyranose had been consumed, water (50 mL) was added and the mixture was extracted twice with EtOAc (100 mL each) and concentrated. Column chromatography (eluting with 1:10 DCM/n-heptane) afforded 1,6-anhydro-2, 3,4-tri-O-tert-butyldimethylsilyl-β-D-glucopyranose (6.4 g, 41%) as a white solid. 1,6-anhydro-2,4-di-O-tert-butyldimethylsilyl-β-D-glucopyranose (4.3 g, 36%) was isolated separately as a white powder.

1,6-anhydro-2,3,4-tri-O-tert-butyldimethylsilyl-β-D-glucopyranose (II''')

<sup>1</sup>H NMR (400 MHz, CDCl<sub>3</sub>) δ 5.28-5.27 (m, 1H), 4.37-4.35 (m, 1H), 4.10 (dd, J=6.8, 0.8 Hz, 1H), 3.67 (dd, J=6.4, 6.4 Hz, 1H), 3.62-3.60 (m, 1H), 3.50 (d, J=1.2 Hz, 1H), 3.45 (d, J=1.2 Hz, 1H), 0.94 (s, 9H), 0.93 (s, 9H), 0.92 (s, 9H), 0.12 (s, 3H), 0.113 (s, 6H), 0.105 (s, 3H), 0.100 (s, 3H), 0.096 (s, 3H).

1,6-anhydro-2,4-di-O-tert-butyldimethylsilyl-β-D-glucopyranose (II')

$^{1}$H NMR (400 MHz, CDCl$_3$) δ 5.29 (s, 1H), 4.39 (d, J=4.8 Hz, 1H), 3.86 (d, J=7.2 Hz, 1H), 3.68 (dd, J=7.2, 5.2 Hz, 1H), 3.55-3.52 (m, 2H), 3.64-3.45 (m, 1H), 2.09 (d, J=5.2 Hz, 1H, OH), 0.943 (s, 9H), 0.938 (s, 9H), 0.140 (s, 3H), 0.130 (s, 6H), 0.126 (s, 3H).

Example 18

Synthesis of 2,4-di-O-tert-butyldimethylsilyl-1-C-phenyl-β-D-glucopyranoside (IVa')

1:20 EtOAc/n-heptane) affording 1-C-phenyl-2,4-di-O-tert-butyldimethylsilyl-β-D-glucopyranoside (0.39 g, 64%) as a white powder.

$^{1}$H NMR (400 MHz, CDCl$_3$) δ 7.36-7.34 (m, 5H), 4.17 (d, J=8.8 Hz, 1H), 3.93-3.87 (m, 1H), 3.73-3.52 (m, 4H), 3.48-3.44 (m, 1H), 2.11 (d, J=2.8 Hz, 1H), 1.96 (dd, J=6.8, 6.4 Hz, 1H), 0.94 (s, 9H), 0.72 (s, 9H), 0.21 (s, 3H), 0.18 (s, 3H), −0.03 (s, 3H), −0.67 (s, 3H); $^{13}$C NMR (100 MHz, CDCl$_3$) δ 139.2 (C), 128.4 (CH), 128.30 (CH×2), 128.26 (CH×2), 82.9 (CH), 80.3 (CH), 79.8 (CH), 76.8 (CH), 71.6 (CH), 62.5 (CH$_2$), 26.0 (CH$_3$×3), 25.8 (CH$_3$×3), 18.3 (C), 18.0 (C), −3.7 (CH$_3$), −4.2 (CH$_3$), −4.8 (CH$_3$), −5.8 (CH$_3$); LCMS (ESI) m/z 469 (100, [M+H]$^+$), 470 (27, [M+H+1]$^+$), 486 (65, [M+NH$_4$]$^+$).

Example 19

Synthesis of 2,4-di-O-tert-butyldimethylsilyl-1-C-phenyl-β-D-glucopyranoside (IVa')

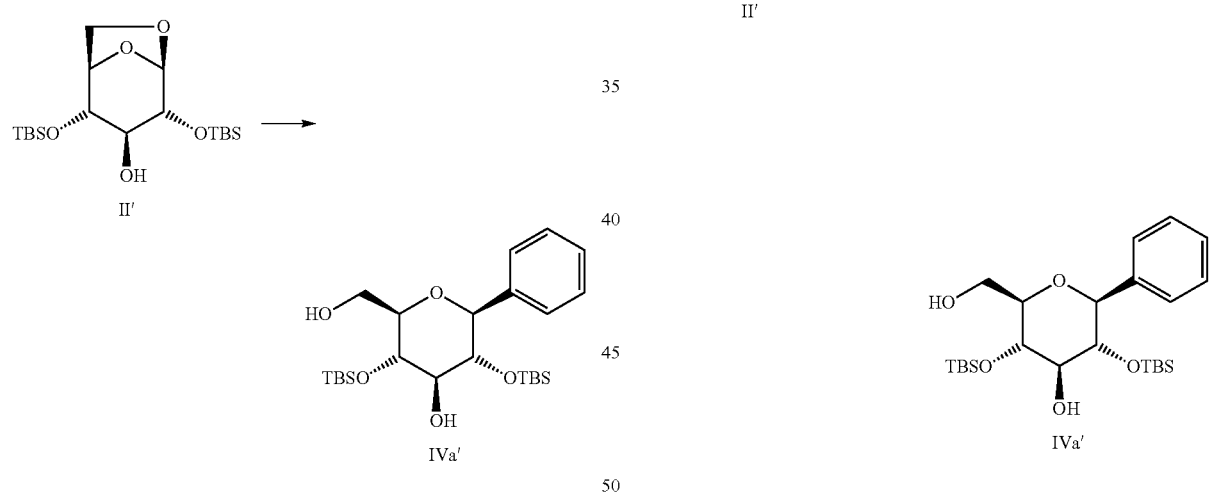

AlCl$_3$ (0.60 ml, 0.30 mmol, 0.5 M in THF) and Ph$_3$Al (1.7 ml, 1.7 mmol, 1.0 M in Bu$_2$O) were mixed at ambient temperature to give a black-colored solution. To this mixture was added a solution of 1,6-anhydro-2,4-di-O-tert-butyldimethylsilyl-β-D-glucopyranose (0.51 g, 1.31 mmol) in PhOMe (3.5 mL) at ambient temperature. The mixture was concentrated under reduced pressure (50 torr) at 60° C. (external bath temperature) to remove the low-boiling ethereal solvent. The remaining mixture (comprising PhOMe/Bu$_2$O as solvent) was heated at 130° C. (external bath temperature) for 4 hours. After cooling to ambient temperature, THF (10 mL), then diatomaceous earth (1 g), then 15% aqueous NaOH (1 mL) and then Na$_2$SO$_4$ (2 g) were added to the product mixture sequentially and the resulting suspension was filtered and the filtrate was concentrated to give a yellow oil, which was purified by silica gel column chromatography (eluting with AlCl$_3$ (0.60 ml, 0.30 mmol, 0.5 M in THF) and Ph$_3$Al (1.7 ml, 1.7 mmol, 1.0 M in Bu$_2$O) were mixed at ambient temperature to give a black-colored solution. To this mixture was added a solution of 1,6-anhydro-2,4-di-O-tert-butyldimethylsilyl-β-D-glucopyranose (0.39 g, 1.00 mmol) in PhOMe (3.5 mL) at ambient temperature. The mixture was concentrated under reduced pressure (50 torr) at 60° C. (external bath temperature) to remove the low-boiling ethereal solvent. The remaining mixture (comprising PhOMe/Bu$_2$O as solvent) was heated at 130° C. (external bath temperature) for 3 hours. After cooling to ambient temperature, THF (10 mL), then diatomaceous earth (0.8 g), then 15% aqueous NaOH (1 mL) and then Na$_2$SO$_4$ (1.9 g) were added sequentially to the product mixture and the resulting suspension was filtered and the filtrate was concentrated to give a yellow oil, which was purified by silica gel column chromatography (eluting with 1:20 EtOAc/n-heptane) affording the product 1-C-phenyl-2,4-di-O-tert-butyldimethylsilyl-β-D-glucopyranoside (0.32 g, 68%) as a white powder.

Example 20

Synthesis of 1-C-phenyl-2,4-di-O-triethylsilyl-β-D-glucopyranoside (IVa''')

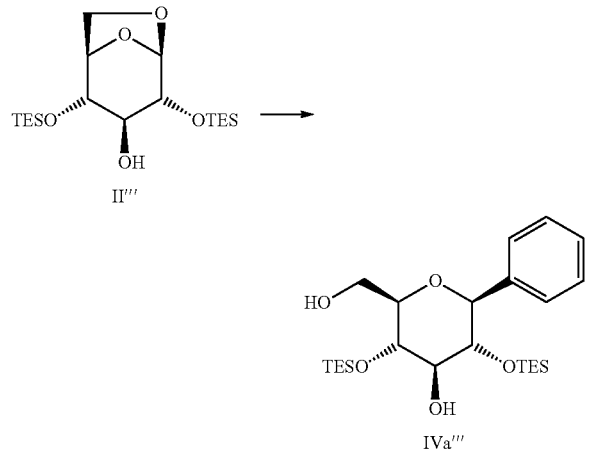

AlCl$_3$ (3.6 mmol, 0.5 M solution in THF) and phenylmagnesium bromide (9.0 mmol, 2.6 M solution in Et$_2$O) were combined to give a black solution. After being stirred at ambient temperature for 1 hour, the solvent was evaporated under vacuum (50 torr) and then PhMe (8.0 mL) was added to the residue. To a solution of 1,6-anhydro-2,4-di-O-triethylsilyl-β-D-glucopyranose (0.72 g, 1.8 mmol; prepared as reported in *Helv. Chim. Acta.* 1998, 81, 2157-2189) in PhMe (4.0 mL) was added phenylmagnesium bromide (1.8 mmol, 2.6 M solution in Et$_2$O) and after stirring for about 5 min the mixture was then partially concentrated under reduced pressure (50 torr) to remove the Et$_2$O. The remaining PhMe solution of 1,6-anhydro-2,4-di-O-triethylsilyl-β-D-glucopyranose was added to the previously prepared aluminum mixture, followed by dilution with PhMe (1.0 mL) The mixture was heated under reflux for 6.5 hours at which time HPLC analysis showed that the reaction was complete and also indicated that a small amount of the unprotected product, 1-C-phenyl-β-D-glucopyranoside, had formed. After cooling to ambient temperature, THF (30 mL), then 10% aqueous NaOH (3 mL), then diatomaceous earth (3 g) and then Na$_2$SO$_4$ (7.5 g) were sequentially added to the product mixture and the resulting suspension was filtered and the filtrate was concentrated to give an orange oil. The oil was purified by silica gel column chromatography (eluting with 1:4 EtOAc/n-heptane) to give the product 1-C-phenyl-2,4-di-O-triethylsilyl-β-D-glucopyranoside (0.44 g, 51%) as a colorless to light yellow oil.

$^1$H NMR (400 MHz, CDCl$_3$) δ 7.37-7.34 (m, 5H), 4.16 (d, J=8.8 Hz, 1H), 3.93-3.88 (m, 1H), 3.75-3.69 (m, 1H), 3.66-3.62 (m, 1H), 3.58-3.51 (m, 2H), 3.49-3.43 (m, 1H), 2.17 (d, J=3.2 Hz, 1H, OH), 2.02 (br, 1H, OH), 1.02 (t, J=7.8 Hz, 9H), 0.77-0.69 (m, 6H), 0.76 (t, J=7.8 Hz, 9H), 0.31 (dq, J=14.8, 7.8 Hz, 3H), 0.20 (dq, J=15.2, 8.0 Hz, 3H); $^{13}$C NMR (100 MHz, CDCl$_3$) δ 139.1 (C), 128.4 (CH), 128.2 (CH×2), 127.9 (CH×2), 82.7 (CH), 80.3 (CH), 79.8 (CH), 77.1 (CH), 71.8 (CH), 62.6 (CH$_2$), 6.9 (CH$_3$×3), 6.7 (CH$_3$×3), 5.2 (CH$_2$×3), 4.8 (CH$_2$×2)

Example 21

Synthesis of 2,4-di-O-tert-butyldiphenylsilyl-1-C-phenyl-β-D-glucopyranoside (IVa'')

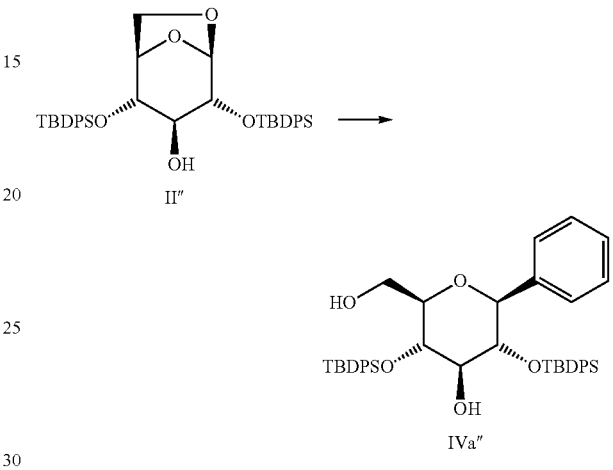

To a mixture of phenylmagnesium bromide (2.6 M in Et$_2$O, 1.9 mL, 5.0 mmol) in PhOMe (6 mL) was added GaCl$_3$ (0.5 M in pentane, 4.0 mL, 2.0 mmol) providing a white slurry that was then stirred for 1 hour. To a solution of 1,6-anhydro-2,4-di-O-tert-butyldiphenylsilyl-β-D-glucopyranose (0.64 g, 1.0 mmol) in PhOMe (3 mL) at ambient temperature was added phenylmagnesium bromide (2.6 M in Et$_2$O, 0.38 mL, 1.0 mmol), and the mixture was stirred for about 5 min. This solution was then added into the previously prepared gallium mixture and the combined mixture was concentrated under vacuum (50 torr) at 60° C. to remove the Et$_2$O and pentane. The remaining solution was heated at 130° C. (external bath temperature) for 24 hours at which time HPLC assay analysis indicated a 2% yield of 2,4-di-O-tert-butyldiphenylsilyl-1-C-phenyl-β-D-glucopyranoside.

Example 22

Synthesis of 2,4-di-O-tert-butyldiphenylsilyl-1-C-(3-((5-(4-fluorophenyl)thiophen-2-yl)methyl)-4-methylphenyl)-β-D-glucopyranoside(2,4-di-O-TBDPS-canagliflozin; (IVi''))

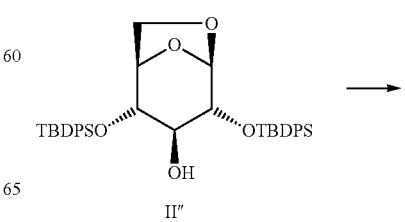

-continued

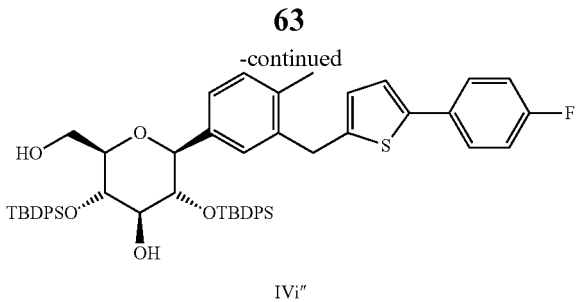

IVi″

2-(5-Bromo-2-methylbenzyl)-5-(4-fluorophenyl)thiophene (1.5 g, 4.15 mmol) and magnesium powder (0.33 g, 13.7 mmol) were placed in a suitable reactor, followed by THF (9 mL) and 1,2-dibromoethane (95 μL). The mixture was heated to reflux. After the reaction was initiated, a solution of 2-(5-bromo-2-methylbenzyl)-5-(4-fluorophenyl)thiophene (2.5 g, 6.92 mmol) in THF (15 mL) was added dropwise. The mixture was stirred for another 2 hours under reflux, and was then cooled to ambient temperature and titrated to determine the concentration. The thus prepared 3-[[5-(4-fluorophenyl)-2-thienyl]methyl]-4-methylphenyl magnesium bromide (0.29 M in THF, 17 mL, 5.0 mmol) and AlCl₃ (0.5 M in THF, 4.0 mL, 2.0 mmol) were mixed at ambient temperature to give a black solution, which was stirred at ambient temperature for 1 hour. To a solution of 1,6-anhydro-2,4-di-O-tert-butyldiphenylsilyl-β-D-glucopyranose (0.64 g, 1.0 mmol) in PhOMe (3.0 mL) at ambient temperature was added n-BuLi (0.4 mL, 1.0 mmol, 2.5 M solution in Bu₂O). After stirring for about 5 min the solution was then added into the above prepared aluminum mixture via syringe, followed by additional PhOMe (1.0 mL) to rinse the flask. The mixture was concentrated under reduced pressure (50 torr) at 60° C. (external bath temperature) to remove low-boiling point ethereal solvents, and PhOMe (6 mL) was then added. The remaining mixture was heated at 150° C. (external bath temperature) for 5 hours at which time HPLC assay analysis indicated a 68% yield of 2,4-di-O-tert-butyldiphenylsilyl-1-C-(3-((5-(4-fluorophenyl)thiophen-2-yl)methyl)-4-methylphenyl)-β-D-glucopyranoside. After cooling to ambient temperature, the reaction was treated with 10% aqueous NaOH (1 mL), THF (10 mL) and diatomaceous earth at ambient temperature, then the mixture was filtered and the filter cake was washed with THF. The combined filtrates were concentrated and the crude product was purified by silica gel column chromatography (eluting with 1:20 MTBE/n-heptane) to give the product 2,4-di-O-tert-butyldiphenylsilyl-1-C-(3-((5-(4-fluorophenyl)thiophen-2-yl)methyl)-4-methylphenyl)-β-D-glucopyranoside (0.51 g, 56%) as a white powder.

¹H NMR (400 MHz, CDCl₃) δ 7.65 (d, J=7.2 Hz, 2H), 7.55 (d, J=7.2 Hz, 2H), 7.48 (dd, J=7.6, 5.6 Hz, 2H), 7.44-7.20 (m, 16H), 7.11-6.95 (m, 6H), 6.57 (d, J=3.2 Hz, 1H), 4.25 (d, J=9.6 Hz, 1H), 4.06 (s, 2H), 3.90-3.86 (m, 1H), 3.81-3.76 (m, 1H), 3.61-3.57 (m, 1H), 3.54-3.49 (m, 2H), 3.40 (dd, J=8.8, 8.8 Hz, 1H), 2.31 (s, 3H), 1.81 (dd, J=6.6, 6.6 Hz, 1H, OH), 1.19 (d, J=4.4 Hz, 1H, OH), 1.00 (s, 9H), 0.64 (s, 9H); ¹³C NMR (100 MHz, CDCl₃) δ 162.1 (d, J=246 Hz, C), 143.1 (C), 141.4 (C), 137.9 (C), 136.8 (C), 136.5 (C), 136.4 (CH×2), 136.1 (CH×2), 135.25 (C), 135.20 (CH×2), 135.0 (CH×2), 134.8 (C), 132.8 (C), 132.3 (C), 130.9 (d, J=3.5 Hz, C), 130.5 (CH), 130.0 (CH), 129.7 (CH), 129.5 (CH), 129.4 (CH), 129.2 (CH), 127.6 (CH×4), 127.5 (CH×2), 127.2 (CH×2), 127.1 (d, J=8.2 Hz, CH×2), 127.06 (CH), 126.0 (CH), 122.7 (CH), 115.7 (d, J=21.8 Hz, CH×2), 82.7 (CH), 80.5 (CH), 79.4 (CH), 76.3 (CH), 72.9 (CH), 62.8 (CH₂), 34.1 (CH₂), 27.2 (CH₃×3), 26.7 (CH₃×3), 19.6, (C), 19.3 (CH₃), 19.2 (C); LCMS (ESI) m/z 938 (100, [M+NH₄]⁺), 943 (10, [M+Na]⁺).

Example 23

Synthesis of canagliflozin(1-C-(3-((5-(4-fluorophenyl)thiophen-2-yl)methyl)-4-methylphenyl)-β-D-glucopyranoside; (Ii))

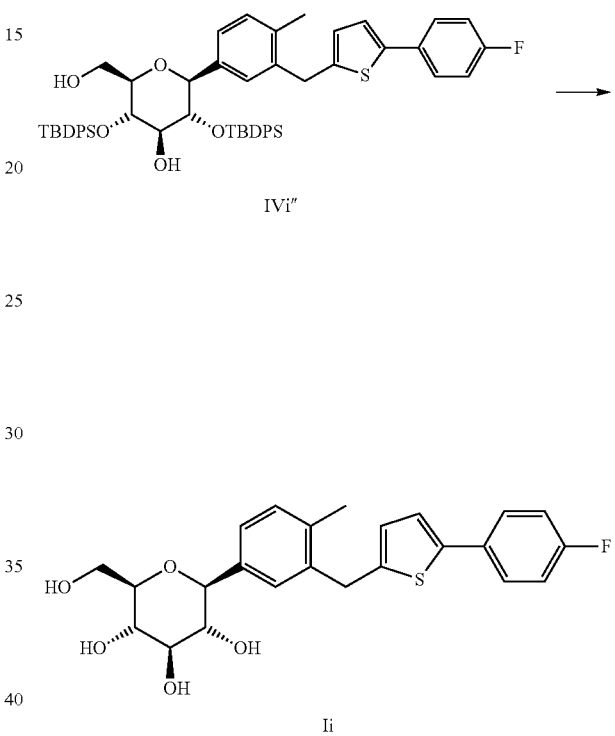

A mixture of the 2,4-di-O-tert-butyldiphenylsilyl-1-C-(3-((5-(4-fluorophenyl)thiophen-2-yl)methyl)-4-methylphenyl)-β-D-glucopyranoside (408 mg, 0.44 mmol) and TBAF (3.5 mL, 3.5 mmol, 1.0 M in THF) was stirred at ambient temperature for 4 hours. CaCO₃ (0.73 g), Dowex® 50WX8-400 ion exchange resin (2.2 g) and MeOH (5 mL) were added to the product mixture and the suspension was stirred at ambient temperature for 1 hour and then the mixture was filtered through a pad of diatomaceous earth. The filter cake was rinsed with MeOH and the combined filtrates was evaporated under vacuum and the resulting residue was purified by column chromatography (eluting with 1:20 MeOH/DCM) affording canagliflozin (143 mg, 73%). ¹H NMR (400 MHz, DMSO-d₆) δ 7.63-7.57 (m, 2H), 7.28 (d, J=3.6 Hz, 1H), 7.23-7.18 (m, 3H), 7.17-7.12 (m, 2H), 6.80 (d, J=3.6 Hz, 1H), 4.93 (br, 2H, OH), 4.73 (br, 1H, OH), 4.44 (br, 1H, OH), 4.16 (d, J=16 Hz, 1H), 4.10 (d, J=16 Hz, 1H), 3.97 (d, J=9.2 Hz, 1H), 3.71 (d, J=11.6 Hz, 1H), 3.47-3.43 (m, 1H), 3.30-3.15 (m, 4H), 2.27 (s, 3H); ¹³C NMR (100 MHz, DMSO-d₆) δ 161.8 (d, J=243 Hz, C), 144.1 (C), 140.7 (C), 138.7 (C), 137.8 (C), 135.4 (C), 131.0 (d, J=3.1 Hz, C), 130.1 (CH), 129.5 (CH), 127.4 (d, J=8.1 Hz, CH×2), 126.8 (CH), 126.7 (CH), 123.9 (CH), 116.4 (d, J=21.6 Hz, CH×2), 81.8 (CH), 81.7

(CH), 79.0 (CH), 75.2 (CH), 70.9 (CH), 61.9 (CH$_2$), 33.9 (CH$_2$), 19.3 (CH$_3$); LCMS (ESI) m/z 462 (100, [M+NH$_4$]$^+$), 467 (3, [M+Na]$^+$).

Example 24

Synthesis of 2,4-di-O-tert-butyldiphenylsilyl-1-C-(4-chloro-3-(4-ethoxybenzyl)phenyl)-β-D-glucopyranoside(2,4-di-O-TBDPS-dapagliflozin; (IVj''))

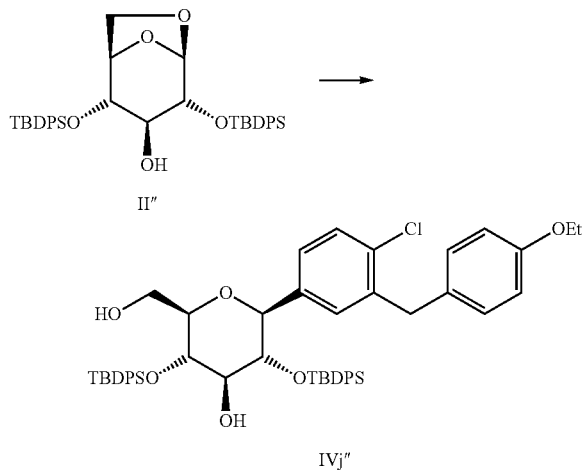

1-(5-Bromo-2-chlorobenzyl)-4-ethoxybenzene (1.5 g, 4.6 mmol) and magnesium powder (0.54 g, 22.2 mmol) were placed in a suitable reactor, followed by THF (12 mL) and 1,2-dibromoethane (0.16 mL). The mixture was heated to reflux. After the reaction had initiated, a solution of 1-(5-bromo-2-chlorobenzyl)-4-ethoxybenzene (4.5 g, 13.8 mmol) in THF (28 mL) was added dropwise. The mixture was allowed to stir for another hour under reflux, and was then cooled to ambient temperature, and then titrated to determine the concentration. The above prepared 4-chloro-3-[(4-ethoxyphenyl)methyl]phenyl magnesium bromide (31 mL, 10 mmol, 0.32 M in THF) and AlCl$_3$ (0.5 M in THF, 8.0 mL, 4.0 mmol) were mixed at ambient temperature to give a black solution, which was stirred at ambient temperature for 1 hour. To a solution of 1,6-anhydro-2,4-di-O-tert-butyldiphenylsilyl-β-D-glucopyranose (0.64 g, 1.0 mmol) in PhOMe (3.0 mL) at ambient temperature was added phenylmagnesium bromide (0.38 mL, 1.0 mmol, 2.6 M solution in Et$_2$O). After stirring for about 5 min the solution was then added into the above prepared aluminum mixture via syringe, followed by additional PhOMe (1.0 mL) to rinse the flask. The mixture was concentrated under reduced pressure (50 torr) at 60° C. (external bath temperature) to remove low-boiling point ethereal solvents and then PhOMe (6 mL) was added. The reaction mixture was heated at 130° C. (external bath temperature) for 8 hours at which time HPLC assay analysis indicated a 51% yield of 2,4-di-O-tert-butyldiphenylsilyl-1-C-(4-chloro-3-(4-ethoxybenzyl)phenyl)-β-D-glucopyranoside. After cooling to ambient temperature, the reaction was treated with 10% aqueous NaOH (1 mL), THF (10 mL) and diatomaceous earth at ambient temperature, then the mixture was filtered and the filter cake was washed with THF. The combined filtrates were concentrated and the crude product was purified by silica gel column chromatography (eluting with 1:30 EtOAc/n-heptane) affording the product 2,4-di-O-tert-butyldiphenylsilyl-1-C-(4-chloro-3-(4-ethoxybenzyl)phenyl)-β-D-glucopyranoside (0.30 g, 34%) as a white powder.

$^1$H NMR (400 MHz, CDCl$_3$) δ 7.56-7.54 (m, 2H), 7.43-7.31 (m, 13H), 7.29-7.22 (m, 6H), 7.07-7.04 (m, 2H), 7.00 (d, J=2.0 Hz, 1H), 6.87 (dd, J=8.4, 2.0 Hz, 1H), 6.83-6.81 (m, 2H), 4.18 (d, J=9.6 Hz, 1H), 4.02 (q, J=6.9 Hz, 2H), 3.96 (d, J=10.8 Hz, 2H), 3.86 (ddd, J=11.3, 7.7, 1.1 Hz, 1H), 3.76 (ddd, J=8.4, 8.4, 4.8 Hz, 1H), 3.56 (ddd, J=9.0, 6.4, 2.4 Hz, 1H), 3.50 (dd, J=11.4, 5.4 Hz, 1H), 3.44 (dd, J=9.4, 8.6 Hz, 1H), 3.38 (dd, J=8.8, 8.8 Hz, 1H), 1.70 (dd, J=7.8, 5.4 Hz, 1H, OH), 1.42 (t, J=6.8 Hz, 3H), 1.21 (d, J=5.2 Hz, 1H, OH), 1.00 (s, 9H), 0.64 (s, 9H); $^{13}$C NMR (100 MHz, CDCl$_3$) δ 157.4 (C), 138.8 (C), 137.4 (C), 136.3 (CH×2), 136.1 (CH×2), 135.2 (CH×2), 135.0 (C), 134.9 (CH×2), 134.8 (C), 134.2 (C), 132.8 (C), 132.0 (C), 131.6 (CH), 131.1 (C), 129.9 (CH×2), 129.7 (CH), 129.6 (CH), 129.5 (CH), 129.4 (CH), 129.2 (CH), 127.58 (CH×2), 127.57 (CH×2), 127.54 (CH×2), 127.31 (CH), 127.28 (CH×2), 114.4 (CH×2), 82.2 (CH), 80.5 (CH), 79.3 (CH), 76.3 (CH), 72.7 (CH), 63.4 (CH$_2$), 62.7 (CH$_2$), 38.2 (CH$_2$), 27.2 (CH$_3$×3), 26.6 (CH$_3$×3), 19.6 (C), 19.2 (C), 14.9 (CH$_3$).

Example 25

Synthesis of dapagliflozin((2S,3R,4R,5S,6R)-2-[4-chloro-3-(4-ethoxybenzyl)phenyl]-6-(hydroxymethyl)tetrahydro-2H-pyran-3,4,5-triol; (Ij))

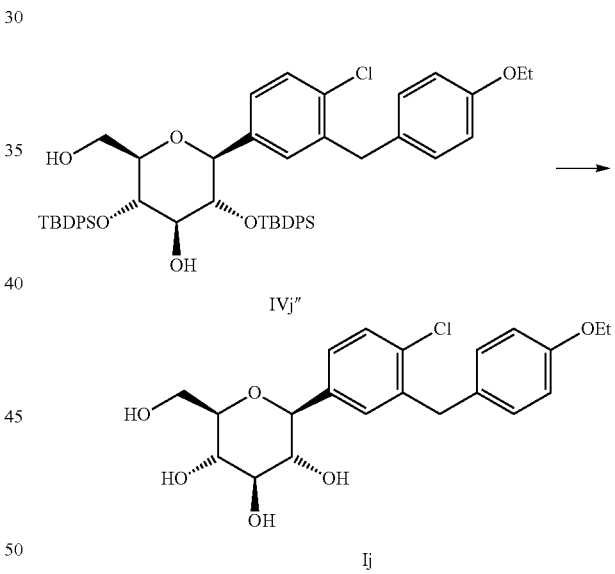

A solution of the 2,4-di-O-tert-butyldiphenylsilyl-1-C-(4-chloro-3-(4-ethoxybenzyl)phenyl)-β-D-glucopyranoside (60 mg, 0.068 mmol) in THF (3.0 mL) and TBAF (3.0 mL, 3.0 mmol, 1.0 M in THF) was stirred at ambient temperature for 15 hours. CaCO$_3$ (0.62 g), Dowex® 50WX8-400 ion exchange resin (1.86 g) and MeOH (5 mL) were added to the product mixture and the suspension was stirred at ambient temperature for 1 hour and then the mixture was filtrated through a pad of diatomaceous earth. The filter cake was rinsed with MeOH and the combined filtrates was evaporated under vacuum and the resulting residue was purified by column chromatography (eluting with 1:10 MeOH/DCM) affording dapagliflozin (30 mg).

$^1$H NMR (400 MHz, CD$_3$OD) δ 7.37-7.34 (m, 2H), 7.29 (dd, J=8.2, 2.2 Hz, 1H), 7.12-7.10 (m, 2H), 6.82-6.80 (m,

2H), 4.10 (d, J=9.6 Hz, 2H), 4.04 (d, J=9.2 Hz, 2H), 4.00 (q, J=7.1 Hz, 2H), 3.91-3.87 (m, 1H), 3.73-3.67 (m, 1H), 3.47-3.40 (m, 3H), 3.31-3.23 (m, 2H), 1.37 (t, J=7.0 Hz, 3H); $^{13}$C NMR (100 MHz, CD$_3$OD) δ 157.4 (C), 138.6 (C), 138.5 (C), 133.1 (C), 131.5 (C), 130.5 (CH), 129.4 (CH×2), 128.7 (CH), 126.8 (CH), 114.0 (CH×2), 80.5 (CH), 80.8 (CH), 78.3 (CH), 75.0 (CH), 70.4 (CH), 63.0 (CH$_2$), 61.7 (CH$_2$), 37.8 (CH$_2$), 13.8 (CH$_3$); LCMS (ESI) m/z 426 (100, [M+NH$_4$]$^+$), 428 (36, [M+NH$_4$+2]$^+$), 447 (33, [M+K]$^+$).

Example 26

Synthesis of 1,6-anhydro-β-D-glucopyranose 2,4-O-phenylboronate (XIa)

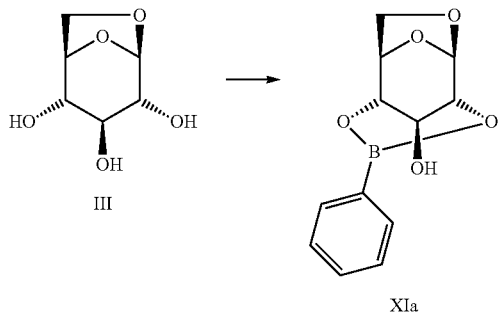

A mixture of 1,6-anhydro-β-D-glucopyranose (5 g, 30.8 mmol) and phenylboronic acid (3.76 g, 30.8 mmol) in PhMe (150 mL) was heated under reflux in a Dean-Stark apparatus for 15 hours. The mixture was cooled to ambient temperature and the white precipitate was filtered and washed with PhMe (10 mL) to give the 1,6-anhydro-β-D-glucopyranose 2,4-O-phenylboronate (4.90 g, 64%).

$^1$H NMR (400 MHz, CDCl$_3$) δ 7.83-7.87 (m, 2H), 7.46-7.51 (m, 1H), 7.37-7.42 (m, 2H), 5.65 (t, J=2.4 Hz, 1H), 4.63-4.67 (m, 1H), 4.58 (d, J=8.0 Hz, 1H), 4.19-4.22 (m, 1H), 4.12-4.16 (m, 1H), 4.08-4.10 (m, 1H), 3.94 (dd, J=7.6 Hz, 4.8 Hz, 1H), 3.44 (d, J=8.8 Hz, 1H); $^{13}$C NMR (100 MHz, CDCl$_3$) δ 134.3, 131.2, 127.7, 101.7, 76.5, 70.3, 70.2, 69.0, 66.2.

Example 27

Synthesis of 1-C-phenyl-β-D-glucopyranoside((2R,3S,4R,5R,6S)-2-(hydroxymethyl)-6-phenyltetrahydro-2H-pyran-3,4,5-triol; (1S)-1-C-phenyl Glucoside; (Ia))

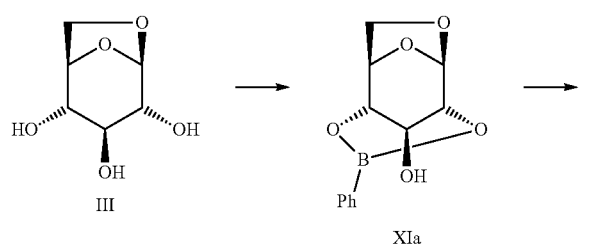

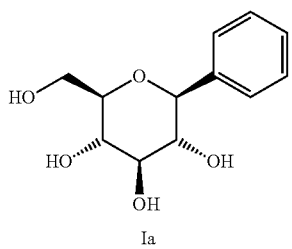

A solution of 1,6-anhydro-β-D-glucopyranose (0.50 g, 3.1 mmol) and phenylboronic acid (0.38 g, 3.1 mmol) in PhMe (40 mL) was heated under reflux for 15 hours with continual removal of water from the reaction system using Dean-Stark apparatus. The product mixture was cooled to ambient temperature and the solvent was removed to give a white precipitate (1,6-anhydro-β-D-glucopyranose 2,4-O-phenylboronate). To the white precipitate was added PhCN (5 mL) and Ph$_3$Al (3.1 mL, 3.1 mmol, 1.0 M in Bu$_2$O) and then the mixture was heated at 160° C. (external bath temperature) under vacuum (50 torr) such that the Bu$_2$O could be removed by distillation. The remaining solution was heated to 180° C. (external bath temperature) until no more 1,6-anhydro-β-D-glucopyranose was detected by TLC (about 2 hours). The product mixture was cooled to ambient temperature and MeOH (5 mL) was added. The mixture was stirred for 10 min and concentrated. The residue was purified by column chromatography (eluting with 1:10 MeOH/DCM) affording 1-C-phenyl-β-D-glucopyranoside (0.41 g, 55% based on 1,6-anhydro-β-D-glucopyranose).

HPLC analysis and assay method for detection of β- and α-anomers of 1-C-phenyl-D-glucopyranoside:

| HPLC column: | Waters XBridge C8 4.6 mm (ID) × 150 mm (L), 3.5 μm of particle size (storage 100% acetonitrile) |
|---|---|
| Flow rate: | 0.5 mL/min (Pmax < 6000 psi) |
| Injection volume: | 2 μL |
| Detection: | UV, 210 nm (PDA 190-400 nm) |
| Column temp.: | 40° C. |
| Sample run time: | 40 min |
| Needle wash: | H$_2$O/acetonitrile = 1:4 |
| Elution: | mobile phase C: acetonitrile mobile phase D: H$_2$O |
| Method: | |

| Time (min) | Flow (mL/min) | % C (acetonitrile) | % D (H$_2$O) |
|---|---|---|---|
| 0.01 | 0.5 | 15 | 85 |
| 10.00 | 0.5 | 30 | 70 |
| 15.00 | 0.5 | 70 | 30 |
| 25.00 | 0.5 | 100 | 0 |
| 30.00 | 0.5 | 100 | 0 |
| 31.00 | 0.5 | 15 | 85 |
| 40.00 | 0.5 | 15 | 85 |

Sample preparation:
Take 0.1 mL of reaction mixture by syringe and inject into 1 mL 5% TFA/acetonitrile solution to prepare the crude sample. And dilute the crude sample to 10% with methanol to prepare the assay sample.
Internal standard: durene (0.5 molar equivalents w.r.t. the starting material)
UV Response ratio used for assay method: 0.46 (1-C-phenyl-β-D-glucopyranoside/durene under UV 210 nm)
The β-anomer eluted at 5.0 minutes and the α-anomer eluted at 5.6 minutes

Example 28

Synthesis of 1-C-phenyl-β-D-glucopyranoside((2R, 3S,4R,5R,6S)-2-(hydroxymethyl)-6-phenyltetrahydro-2H-pyran-3,4,5-triol; (1S)-1-C-phenyl Glucoside; (Ia))

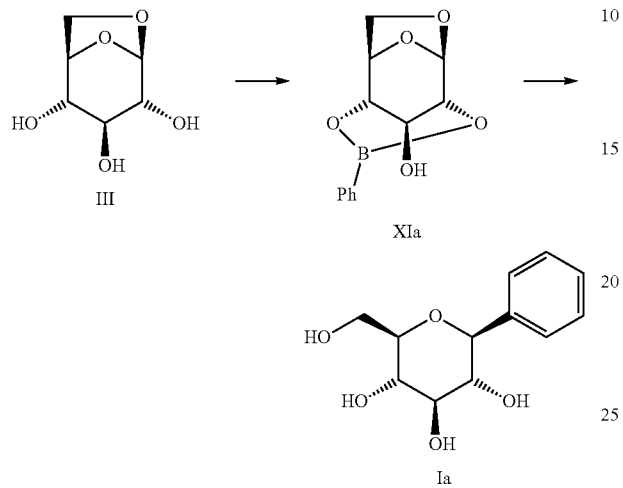

A solution of 1,6-anhydro-β-D-glucopyranose (0.75 g, 4.6 mmol) and phenylboronic acid (0.79 g, 6.5 mmol) in PhMe (40 mL) was heated under reflux for 15 hours with continual removal of water from the reaction system using Dean-Stark apparatus. The reaction was cooled to ambient temperature and Ph₃Al (4.6 mL, 4.6 mmol, 1.0 M in Bu₂O) and AlCl₃ (4.6 mL, 2.3 mmol, 0.5 M in THF) were added. The reaction mixture was heated under reflux for 20 hours. The product mixture was cooled to ambient temperature, MeOH (10 mL) was added and stirred for 10 min, and the mixture was concentrated under reduced pressure followed by column chromatography (eluting with 1:10 MeOH/DCM) affording 1-C-phenyl-β-D-glucopyranoside (0.38 g, 34% based on 1,6-anhydro-β-D-glucopyranose).

Example 29

Synthesis of 1-C-phenyl-β-D-glucopyranoside((2R, 3S,4R,5R,6S)-2-(hydroxymethyl)-6-phenyltetrahydro-2H-pyran-3,4,5-triol; (1S)-1-C-phenyl Glucoside; (Ia))

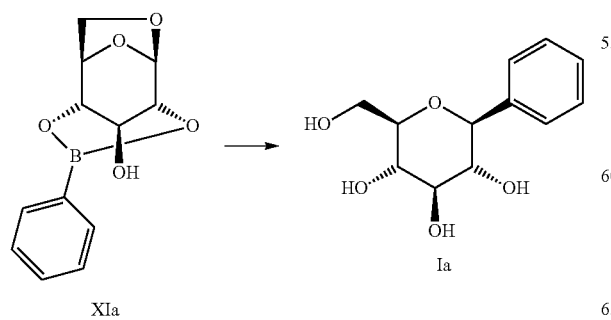

To a solution of 1,6-anhydro-β-D-glucopyranose 2,4-O-phenylboronate (248 mg, 1.0 mmol) in PhOMe (5 mL) at ambient temperature was added Ph₃Al (3.0 mL, 3.0 mmol, 1.0 M in Bu₂O). The mixture was heated at 165° C. (external bath temperature) for 6 hours at which time HPLC assay analysis indicated a 65% yield of 1-C-phenyl-β-D-glucopyranoside had been afforded.

Example 30

Synthesis of 1,6-anhydro-β-D-glucopyranose 2,4-O-(4'-fluorophenyl)boronate (XIf)

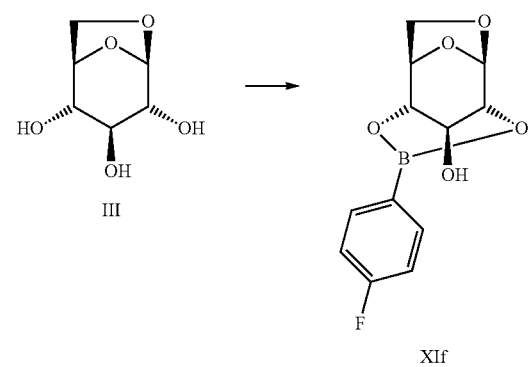

A solution of 1,6-anhydro-β-D-glucopyranose (2.5 g, 15.4 mmol) and 4-fluorophenylboronic acid (2.15 g, 15.4 mmol) in PhMe (70 mL) was heated to reflux under Dean-Stark apparatus for 15 hours. The reaction was cooled and the white precipitate was filtrated. The white precipitate was washed with PhMe (10 mL) to give 1,6-anhydro-β-D-glucopyranose 2,4-O-(4'-fluorophenyl)boronate (2.86 g, 70%).

¹H NMR (400 MHz, CDCl₃) δ 7.81-7.86 (m, 2H), 7.04-7.10 (m, 2H), 5.64 (t, J=2.4 Hz, 1H), 4.62-4.64 (m, 1H), 4.58 (d, J=8.0 Hz, 1H), 4.18-4.22 (m, 1H), 4.10-4.15 (m, 1H), 4.07-4.09 (m, 1H), 3.94 (dd, J=8.0 Hz, 4.8 Hz, 1H), 3.42 (d, J=8.4 Hz, 1H); ¹³C NMR (100 MHz, CDCl₃) δ 165.1 (d, J=248 Hz), 136.5 (d, J=8.2 Hz), 114.7 (d, J=20.0 Hz), 101.6, 76.5, 70.3, 70.1, 69.0, 66.2.

Example 31

Synthesis of 1-C-phenyl-β-D-glucopyranoside((2R, 3S,4R,5R,6S)-2-(hydroxymethyl)-6-phenyltetrahydro-2H-pyran-3,4,5-triol; (1S)-1-C-phenyl Glucoside; (Ia))

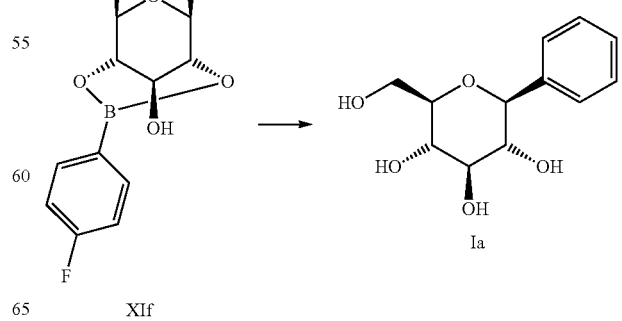

To a solution of 1,6-anhydro-β-D-glucopyranose 2,4-O-(4'-fluorophenyl)boronate (266 mg, 1.0 mmol) in PhOMe (5 mL) at ambient temperature was added Ph₃Al (3.0 mL, 3.0 mmol, 1.0 M in Bu₂O). The mixture was heated at 165° C. (external bath temperature) for 6 hours at which time HPLC assay indicated that a 60% yield of 1-C-phenyl-β-D-glucopyranoside had been achieved.

Example 32

Synthesis of 1,6-anhydro-β-D-glucopyranose 2,4-O-(4'-methoxylphenyl)boronate (XId)

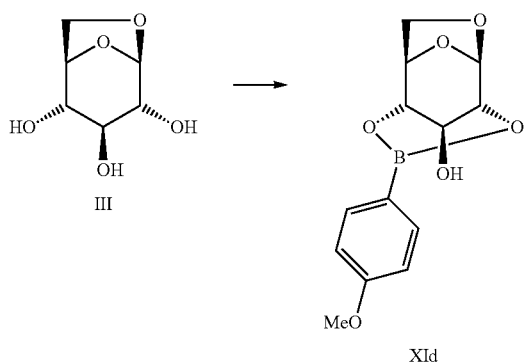

A solution of 1,6-anhydro-β-D-glucopyranose (2.5 g, 15.4 mmol) and 4-methoxylphenylboronic acid (2.35 g, 15.4 mmol) in PhMe (70 mL) was heated under reflux in a Dean-Stark apparatus for 15 hours. The reaction was cooled to ambient temperature give a white precipitate, which was filtered and washed with PhMe (10 mL) yielding 1,6-anhydro-β-D-glucopyranose 2,4-O-(4'-methoxylphenyl)boronate (4.28 g, 99%).

$^1$H NMR (400 MHz, CDCl₃) δ 7.79 (d, J=8.8 Hz, 2H), 6.92 (d, J=8.8 Hz, 2H), 5.63 (t, J=2.4 Hz, 1H), 4.62-4.64 (m, 1H), 4.57 (d, J=7.6 Hz, 1H), 4.17-4.19 (m, 1H), 4.10-4.14 (m, 1H), 4.05-4.08 (m, 1H), 3.93 (dd, J=7.6 Hz, 4.8 Hz, 1H), 3.85 (s, 3H), 3.45 (d, J=8.8 Hz, 1H); $^{13}$C NMR (100 MHz, CDCl₃) δ 162.1, 136.0, 113.3, 101.7, 76.6, 70.3, 70.2, 68.9, 66.2, 55.1.

Example 33

Synthesis of 1-C-phenyl-β-D-glucopyranoside((2R, 3S,4R,5R,6S)-2-(hydroxymethyl)-6-phenyltetrahydro-2H-pyran-3,4,5-triol; (1S)-1-C-phenyl Glucoside; (Ia))

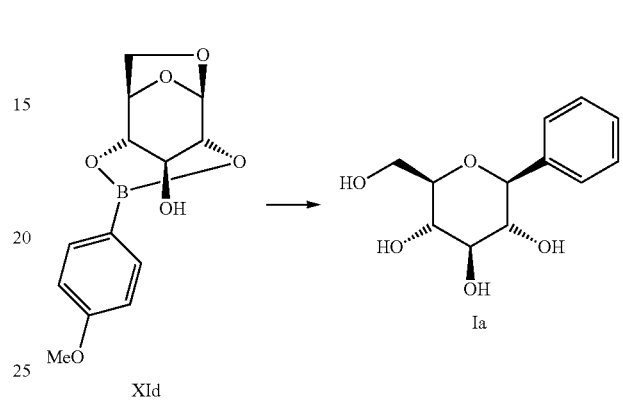

To a solution of 1,6-anhydro-β-D-glucopyranose 2,4-O-(4'-methoxylphenyl)boronate (278 mg, 1.0 mmol) in PhOMe (5 mL) was added Ph₃Al (3.0 mL, 3.0 mmol, 1.0 M in Bu₂O). The mixture was heated at 165° C. (external bath temperature) for 6 hours at which time HPLC assay analysis showed that a 57% yield of 1-C-phenyl-β-D-glucopyranoside had been achieved.

Example 34

Synthesis of 1-C-phenyl-β-D-glucopyranoside((2R, 3S,4R,5R,6S)-2-(hydroxymethyl)-6-phenyltetrahydro-2H-pyran-3,4,5-triol; (1S)-1-C-phenyl Glucoside; (Ia))

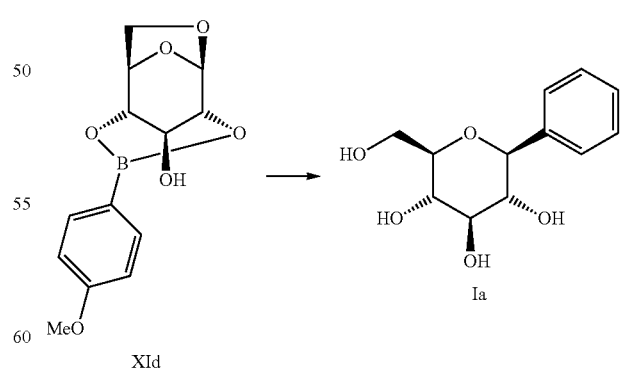

To a solution of 1,6-anhydro-β-D-glucopyranose 2,4-O-(4'-methoxylphenyl)boronate (278 mg, 1.0 mmol) in PhCN (5 mL) was added Ph₃Al (1.0 mL, 1.0 mmol, 1.0 M in Bu₂O). The mixture was then stirred at about 165° C. (external bath temperature) for 22 hours. HPLC assay analysis indicated a 43% yield of 1-C-phenyl-β-D-glucopyranoside was provided.

Example 35

Synthesis of 1,6-anhydro-β-D-glucopyranose 2,4-O-(2',3',4',5',6'-pentafluorophenyl)boronate (XIk)

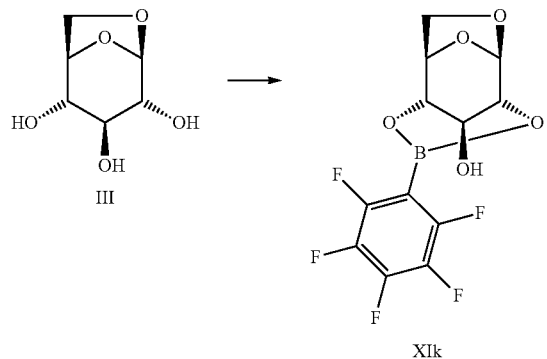

A solution of 1,6-anhydro-β-D-glucopyranose (2.5 g, 15.4 mmol) and pentafluorophenylboronic acid (3.26 g, 15.4 mmol) in PhMe (70 mL) was heated under reflux in Dean-Stark apparatus for 2 hours. The solvent (PhMe) was evaporated under reduced pressure to give 1,6-anhydro-β-D-glucopyranose 2,4-O-(2',3',4',5',6'-pentafluorophenyl)boronate as a yellow solid, which was directly used in the next step without further purification.

$^1$H NMR (400 MHz, CDCl$_3$) δ 5.65 (t, J=2.4 Hz, 1H), 4.64-4.68 (m, 1H), 4.61 (d, J=8.0 Hz, 1H), 4.25-4.28 (m, 1H), 4.18-4.23 (m, 1H), 4.12-4.15 (m, 1H), 3.99 (dd, J=8.0 Hz, 4.8 Hz, 1H), 3.40 (d, J=8.4 Hz, 1H). $^{13}$C NMR (100 MHz, CDCl$_3$) δ 147.7-150.4 (m), 141.3-143.9 (m), 135.9-138.6 (m), 101.2, 76.3, 71.2, 69.7, 69.6, 66.5.

Example 36

Synthesis of 1-C-phenyl-β-D-glucopyranoside((2R,3S,4R,5R,6S)-2-(hydroxymethyl)-6-phenyltetrahydro-2H-pyran-3,4,5-triol; (1S)-1-C-phenyl Glucoside; (Ia))

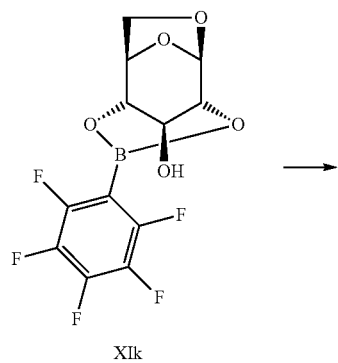

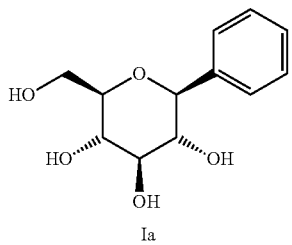

To a solution of crude 1,6-anhydro-β-D-glucopyranose 2,4-O-(2',3',4',5',6'-*pentafluorophenyl*)*boronate* (338 mg, 1.0 mmol) in PhOMe (5 mL) was added Ph$_3$Al (3.0 mL, 3.0 mmol, 1.0 M in Bu$_2$O). The mixture was heated at 165° C. (external bath temperature) for 6 hours at which time HPLC assay showed a 51% yield of 1-C-phenyl-β-D-glucopyranoside.

Example 37

Synthesis of 1,6-anhydro-β-D-glucopyranose 2,4-O-(2',4',6'-*trimethylphenyl*)boronate (XIb)

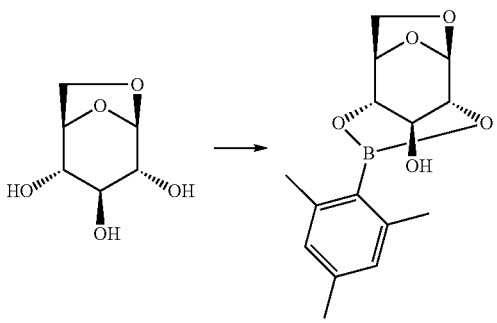

A solution of 1,6-anhydro-β-D-glucopyranose (162 mg, 1.0 mmol) and 2,4,6-trimethylphenyl)boronic acid (164 mg, 1.0 mmol) in PhOMe (5 mL) was heated under reflux in Dean-Stark apparatus for 12 hours to give crude 1,6-anhydro-β-D- glucopyranose 2,4-O-(2',4',6'-*trimethylphenyl*)*boronate*, which was directly used in the next step without further *purification*.

Example 38

Synthesis of 1-C-phenyl-β-D-glucopyranoside((2R, 3S,4R,5R,6S)-2-(hydroxymethyl)-6-phenyltetrahydro-2H-pyran-3,4,5-triol; (1S)-1-C-phenyl Glucoside; (Ia))

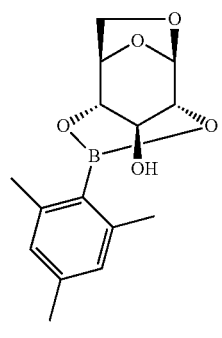

XIb

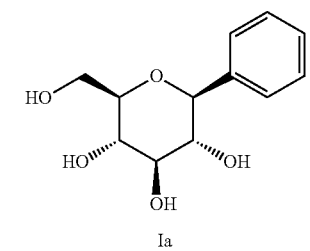

Ia

To the crude PhOMe solution of 1,6-anhydro-β-D-glucopyranose 2,4-O-(2',4',6'-trimethylphenyl)boronate (≤1.0 mmol) prepared above was added Ph₃Al (3.0 mL, 3.0 mmol, 1.0 M in Bu₂O). The mixture was heated at 165° C. (external bath temperature) for 3.5 hours at which time HPLC assay showed a 39% yield of 1-C-phenyl-β-D-glucopyranoside.

Example 39

Synthesis of 1-C-phenyl-β-D-glucopyranoside((2R, 3S,4R,5R,6S)-2-(hydroxymethyl)-6-phenyltetrahydro-2H-pyran-3,4,5-triol; (Ia))

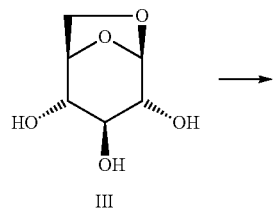

III

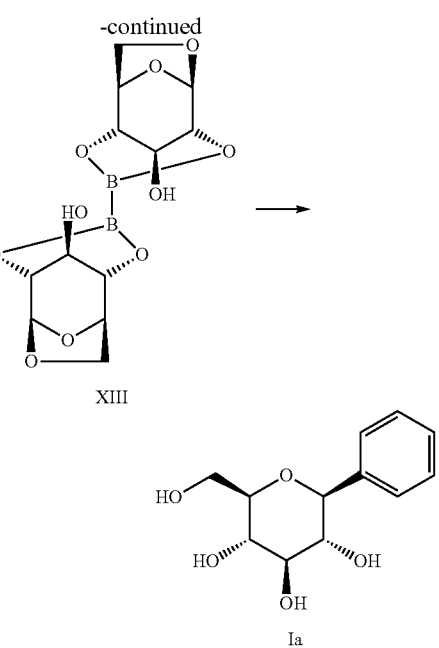

XIII

Ia

A mixture of 1,6-anhydro-β-D-glucopyranose (324 mg, 2 mmol) and tetrahydroxydiboron (90 mg, 1 mmol) in dioxane (40 mL) was heated under reflux in a Dean-Stark apparatus with molecular sieves installed in the side arm for 15 hours. ¹H NMR analysis of a sample of the product mixture indicated that it was composed of a mixture of products. To the product mixture was added Ph₃Al (6.0 mL, 1 M in Bu₂O) and the mixture was then heated at 135° C. (external bath temperature). At about 24 hours HPLC assay analysis indicated that a 53% yield of 1-C-phenyl-β-D-glucopyranoside had been achieved and HPLC purity analysis indicated a 97.8:2.2 ratio of the β-anomer/α-anomer.

Example 40

Synthesis of 2,4-O-dibutylstannylene-1,6-anhydro-β-D-glucopyranose (XIIa)

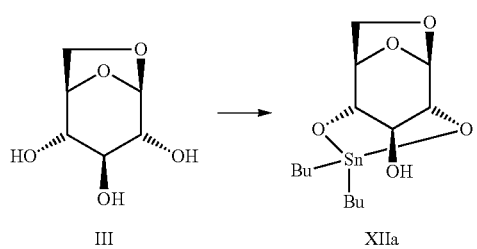

III                    XIIa

A solution of 1,6-anhydro-β-D-glucopyranose (1.0 g, 6.2 mmol) and dibutyltin oxide (1.5 g, 6.2 mmol) in PhMe (40 mL) was heated under reflux for 15 hours with continual removal of water from the reaction system in Dean-Stark apparatus. The product mixture was evaporated under reduced pressure until the solvent (PhMe) has been removed. The residue was cooled to ambient temperature affording 2,4-O-dibutylstannylene-1,6-anhydro-β-D-glucopyranose (2.42 g, 99%).

¹H NMR (400 MHz, CDCl₃) δ 5.47 (t, J=2.0 Hz, 1H), 4.49-4.53 (m, 1H), 4.27 (d, J=7.6 Hz, 1H), 3.76-3.80 (m, 2H), 3.69-3.73 (m, 1H), 3.65-3.68 (m, 1H), 3.78 (d, J=7.2 Hz, 1H), 1.66-1.75 (m, 4H), 1.27-1.45 (m, 8H), 0.92-0.97 (m, 6H).

Example 41

Synthesis of 1-C-phenyl-β-D-glucopyranoside((2R, 3S,4R,5R,6S)-2-(hydroxymethyl)-6-phenyltetrahydro-2H-pyran-3,4,5-triol; (1S)-1-C-phenyl Glucoside; (Ia))

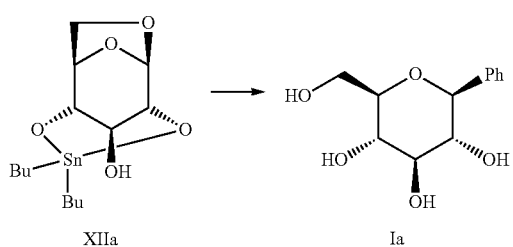

To a solution of 2,4-O-dibutylstannylene-1,6-anhydro-β-D-glucopyranose (0.39 g, 1.0 mmol) in 1,2-dichlorobenzene (8 mL) was added Ph$_3$Al (3.0 mL, 3.0 mmol, 1.0 M in Bu$_2$O) and then the mixture was heated at 165° C. (external bath temperature) for 1.5 hours at which time HPLC assay showed a 29% yield of 1-C-phenyl-β-D-glucopyranoside.

Example 42

Synthesis of 1-C-phenyl-β-D-glucopyranoside((2R, 3S,4R,5R,6S)-2-(hydroxymethyl)-6-phenyltetrahydro-2H-pyran-3,4,5-triol; (1S)-1-C-phenyl Glucoside; (Ia))

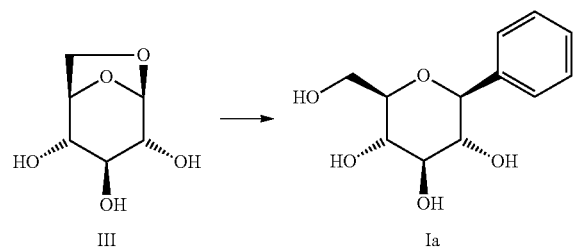

To a suspension of 1,6-anhydro-β-D-glucopyranose (162 mg, 1.0 mmol) in dioxane (5 mL) was added Ph$_3$Al (6.0 mL, 6.0 mmol, 1.0 M in Bu$_2$O) at ambient temperature. The mixture was then heated to 135° C. (external bath temperature) for 150 hours. The mixture was cooled to ambient temperature and diluted with THF (5 mL), and then water (0.5 mL), 15% aqueous NaOH (0.25 mL) and diatomaceous earth were added sequentially. The mixture was stirred for 1 hour and MgSO$_4$ (1 g) was added and then was filtered. To the filtered solid was added MeOH (5 mL) and 15% aqueous NaOH (0.12 mL). The suspension was stirred for 1 hour and then filtered again. The filtrates were combined and concentrated. The residue was purified by column chromatography (eluting with 1:10 MeOH/DCM) affording 1-C-phenyl-β-D-glucopyranoside (170 mg, 71%).

Example 43

Synthesis of 1-C-phenyl-β-D-glucopyranoside((2R, 3S,4R,5R,6S)-2-(hydroxymethyl)-6-phenyltetrahydro-2H-pyran-3,4,5-triol; (1S)-1-C-phenyl Glucoside; (Ia))

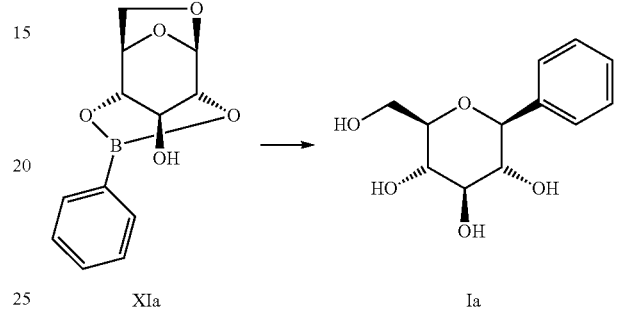

To a suspension of AlCl$_3$ (53 mg, 0.4 mmol) in DCM (1.5 mL) was added Ph$_3$Al (2.0 mL, 2.0 mmol, 1.0 M in Bu$_2$O) at ambient temperature. After stirring for 3 hours, a solution of 1,6-anhydro-β-D-glucopyranose 2,4-O-phenylboronate (248 mg, 1.0 mmol) in PhCl (4.2 mL) was added and the combined mixture was evaporated to remove the low-boiling components at 60-70° C. under reduced pressure (50 torr). The residue was then heated at 150° C. for 3.5 hours. 5% TFA/acetonitrile solution (3 mL) and added and following separation and solvent evaporation the resulted crude mixture was purified by column chromatography (eluting with 1:9 MeOH/DCM) affording the desired 1-C-phenyl-β-D-glucopyranoside (162 mg, 67%) as a yellow oil.

Example 44

Synthesis of 1-C-phenyl-β-D-glucopyranoside((2R, 3S,4R,5R,6S)-2-(hydroxymethyl)-6-phenyltetrahydro-2H-pyran-3,4,5-triol; (1S)-1-C-phenyl Glucoside; (Ia))

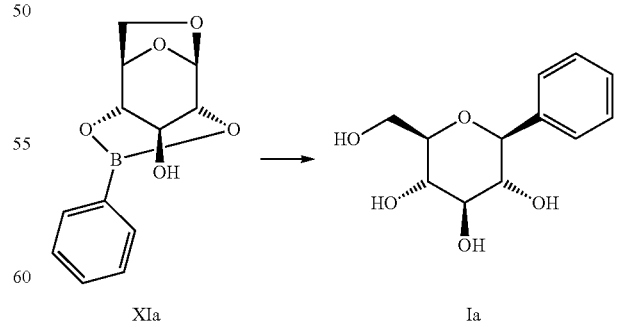

To a solution of AlCl$_3$ (0.8 mL, 0.4 mmol, 0.5 M in THF) in PhOMe (8.0 mL) was added with Ph$_3$Al (2.0 mL, 2.0 mmol, 1.0 M in Bu$_2$O) at ambient temperature. After stirring at ambient temperature for 3 hours, 1,6-anhydro-β-D-glucopyranose 2,4-O-phenylboronate (248 mg, 1.0 mmol) was added and the mixture was heated at 100-110° C. (internal temperature). A sample was taken at 1.5 hours at which time HPLC analysis indicated that the reaction was complete. After cooling the mixture to ambient temperature, the product mixture was treated with MeOH (5.0 mL) with stirring for about 10 mins, and HPLC assay analysis indicated a 66% yield of 1-C-phenyl-β-D-glucopyranoside.

Example 45

Synthesis of 1-C-phenyl-β-D-glucopyranoside((2R, 3S,4R,5R,6S)-2-(hydroxymethyl)-6-phenyltetrahydro-2H-pyran-3,4,5-triol; (1S)-1-C-phenyl Glucoside; (Ia))

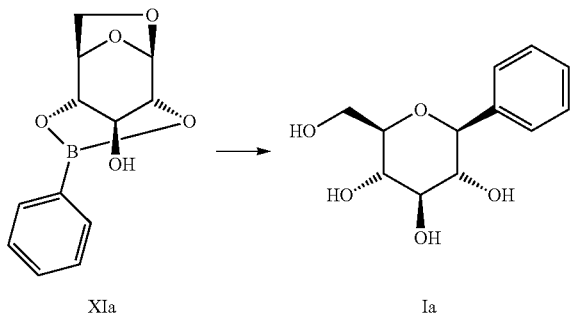

XIa → Ia

To a solution of AlCl₃ (0.4 mL, 0.8 mmol, 0.5 M in THF) in PhOMe (7.6 mL) was added with Ph₃Al (2.2 mL, 2.2 mmol, 1.0 M in Bu₂O) at ambient temperature. After stirring at ambient temperature for 3 hours, 1,6-anhydro-β-D-glucopyranose 2,4-O-phenylboronate (248 mg, 1.0 mmol) was added and the mixture was heated at 100-110° C. (internal temperature). A sample was taken after 2.5 hours at which time HPLC analysis indicated that the reaction was complete. After cooling the mixture to ambient temperature, the product mixture was treated with MeOH (5.0 mL) with stirring for about 10 mins. HPLC assay analysis indicated a 71% yield of 1-C-phenyl-β-D-glucopyranoside.

Example 46

Synthesis of 1-C-phenyl-β-D-glucopyranoside((2R, 3S,4R,5R,6S)-2-(hydroxymethyl)-6-phenyltetrahydro-2H-pyran-3,4,5-triol; (1S)-1-C-phenyl Glucoside; (Ia))

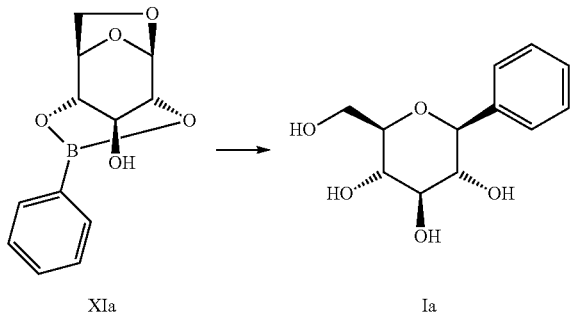

XIa → Ia

AlCl₃ (1.3 mL, 0.67 mmol, 0.5 M in THF), Ph₃Al (1.3 mL, 1.3 mmol, 1.0 M in Bu₂O) and PhOMe (2.5 mL) were mixed at ambient temperature and were then stirred for 3.0 hours. To a solution of 1,6-anhydro-β-D-glucopyranose 2,4-O-phenylboronate (248 mg, 1.0 mmol) in PhOMe (2.5 mL) at −20° C. in another flask was added dropwise with stirring n-BuLi (0.63 mL, 1.0 mmol, 1.6 M in hexane). After stirring for 20 min, the aluminum mixture was added into the prepared solution at −20° C. and was allowed to slowly warm to ambient temperature. The mixture was then heated at 100-110° C. (internal temperature) for 3 hours at which time HPLC assay analysis indicated a 33% yield of 1-C-phenyl-β-D-glucopyranoside.

Example 47

Synthesis of 1-C-phenyl-β-D-glucopyranoside((2R, 3S,4R,5R,6S)-2-(hydroxymethyl)-6-phenyltetrahydro-2H-pyran-3,4,5-triol; (1S)-1-C-phenyl Glucoside; (Ia))

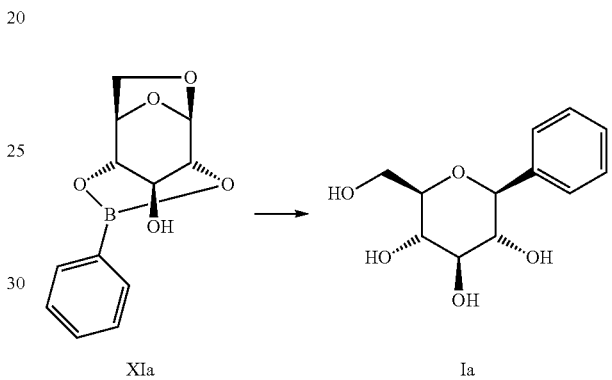

XIa → Ia

AlCl₃ (1.0 mL, 0.5 mmol, 0.5 M in THF) and Ph₃Al (1.0 mL, 1.0 mmol, 1.0 M in Bu₂O) solutions were mixed and stirred for 3.0 hours at ambient temperature. In another flask, to a solution of 1,6-anhydro-β-D-glucopyranose 2,4-O-phenylboronate (186 mg, 0.75 mmol) in PhOMe (8.0 mL) at 0° C. was added dropwise with stirring DIBAL (750 µL, 0.75 mmol, 1.0 M in toluene). After stirring for 40 min, the resulting solution was added to the above prepared arylaluminum mixture at 0° C. and was allowed to slowly warm to ambient temperature. The mixture was then heated at 110° C. (internal temperature) for 2.5 hours at which time HPLC assay analysis indicated a 51% yield of 1-C-phenyl-β-D-glucopyranoside had been achieved.

Example 48

Synthesis of 1-C-phenyl-β-D-glucopyranoside((2R, 3S,4R,5R,6S)-2-(hydroxymethyl)-6-phenyltetrahydro-2H-pyran-3,4,5-triol; (1S)-1-C-phenyl Glucoside; (Ia))

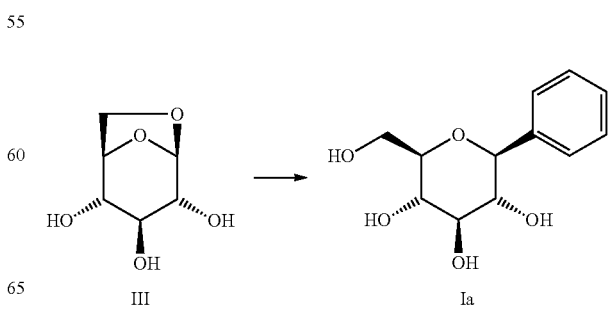

III → Ia

To 1,6-anhydro-β-D-glucopyranose (324 mg, 2.0 mmol) in PhMe (30 mL) was added DIBAL (2.0 mL, 2.0 mmol, 1.0 M in PhMe) and the mixture was stirred at ambient temperature for 3.5 days. To the mixture was then added Ph₃Al (2.0 mL, 2.0 mmol, 1.0 M in Bu₂O) and the mixture was then stirred at 105° C. (external bath temperature) for 18 hours. The mixture was cooled to ambient temperature and then AlCl₃ (4.0 mL, 2.0 mmol, 0.5 M in THF) was added and the mixture was then heated under reflux for 24 hours. The mixture was cooled to ambient temperature and MeOH (10 mL) was added and stirred for 1 hour. The resulting mixture was concentrated under reduced pressure and the residue was purified by column chromatography (eluting with 1:10 MeOH/DCM) providing 1-C-phenyl-β-D-glucopyranoside (117 mg, 24%).

Example 49

Synthesis of 1-C-phenyl-β-D-glucopyranoside((2R, 3S,4R,5R,6S)-2-(hydroxymethyl)-6-phenyltetrahydro-2H-pyran-3,4,5-triol; (1S)-1-C-phenyl Glucoside; (Ia))

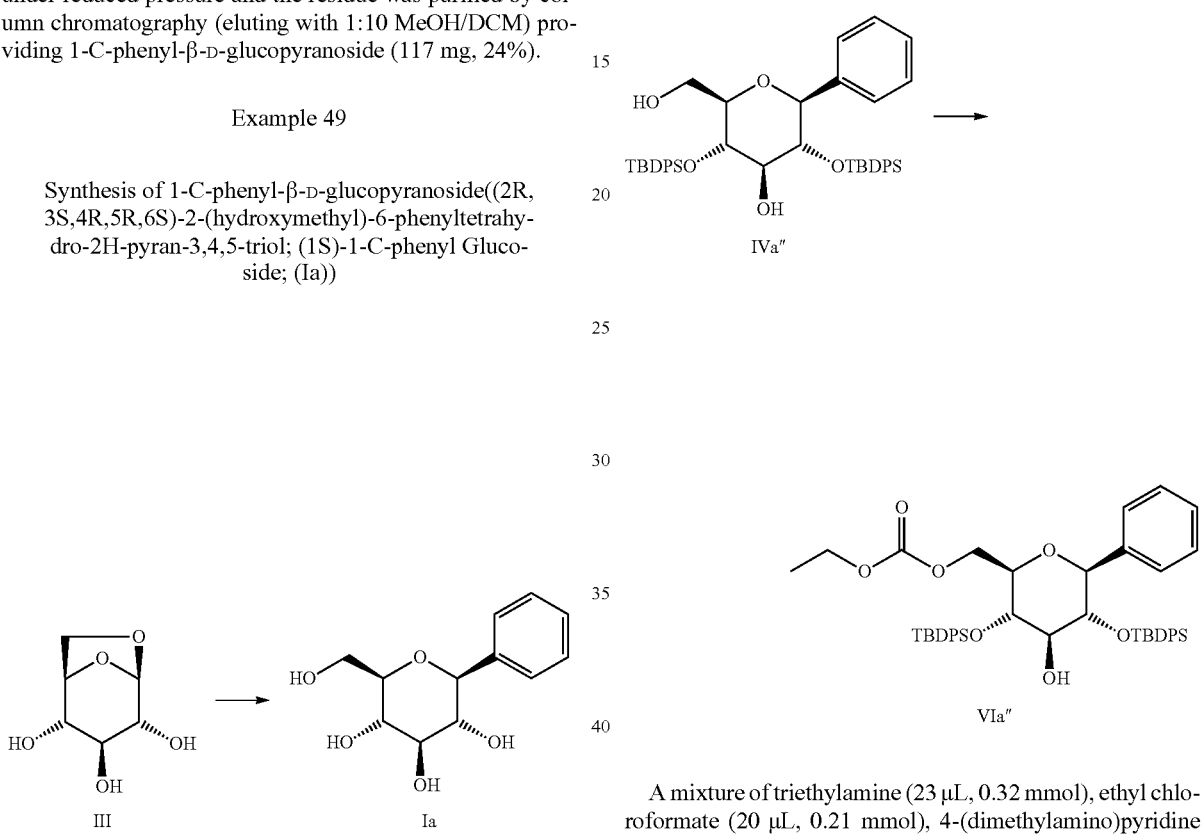

A mixture of Me₃Al (1 mL, 2.0 mmol, 2.0 M in PhMe) and 1,6-anhydro-β-D-glucopyranose (324 mg, 2 mmol) in PhMe (30 mL) was stirred at ambient temperature for 3.5 days. To the resulting mixture was added Ph₃Al (2 mL, 2.0 mmol, 1.0 M in Bu₂O) and the mixture was then stirred at 105° C. (external bath temperature) for about 18 hours. The mixture was cooled to ambient temperature and then AlCl₃ (4.0 mL, 2.0 mmol, 0.5 M in THF) was added and the mixture was then heated under reflux for 24 hours. The mixture was cooled to ambient temperature and MeOH (10 mL) was added and stirred for 1 min. The resulting mixture was concentrated under reduced pressure and the residue was purified by column chromatography (eluting with 1:10 MeOH/DCM) providing 1-C-phenyl-β-D-glucopyranoside (88 mg, 18%).

Example 50

Synthesis of 2,4-di-O-(tert-butyldiphenyl)silyl-6-O-(ethoxycarbonyl)-1-C-phenyl-β-D-glucopyranoside (VIa")

A mixture of triethylamine (23 μL, 0.32 mmol), ethyl chloroformate (20 μL, 0.21 mmol), 4-(dimethylamino)pyridine (2.1 mg, 0.017 mmol) and 2,4-di-O-tert-butyldiphenylsilyl-1-C-phenyl-β-D-glucopyranoside (50 mg, 0.070 mmol) in DCM (0.6 mL) was stirred at ambient temperature for 2 hours. After the reaction was complete, DCM (10 mL) was added, followed by aqueous HCl (10 mL, 0.5 M). After phase separation, the organic solution was concentrated under reduced pressure and the residue was purified by column chromatography (eluting with 1:19 EtOAc/n-heptane) affording 2,4-di-O-tert-butyldiphenylsilyl-6-O-(ethoxycarbonyl)-1-C-phenyl-β-D-glucopyranoside (53 mg, 96%).

$^1$H NMR (400 MHz, CDCl₃) δ 7.66-7.64 (m, 2H), 7.56-7.54 (m, 2H), 7.44-7.16 (m, 21H), 4.40 (dd, J=11.6, 1.6 Hz, 1H), 4.25 (d, J=9.2 Hz, 1H), 4.21-4.16 (m, 1H), 4.11 (q, J=7.3 Hz, 2H), 3.82-3.73 (m, 2H), 3.52-3.44 (m, 2H), 1.25 (t, J=7.0 Hz, 3H), 1.18 (d, J=4.8 Hz, 1H, OH), 1.00 (s, 9H), 0.61 (s, 9H); $^{13}$C NMR (100 MHz, CDCl₃) δ 154.8 (C), 138.4 (C), 136.4 (CH×2), 136.2 (CH×2), 135.4 (C), 135.2 (C), 135.1 (CH×2), 134.9 (CH×2), 132.5 (C), 131.9 (C), 129.7 (CH), 129.6 (CH), 129.3 (CH), 129.1 (CH), 128.7 (CH×2), 128.4 (CH), 128.2 (CH×2), 127.55 (CH×2), 127.54 (CH×2), 127.52 (CH×2), 127.3 (CH×2), 83.1 (CH), 79.4 (CH), 78.3 (CH), 76.4 (CH), 72.3 (CH), 67.2 (CH₂), 63.9 (CH₂), 27.2 (CH₃×3), 26.6 (CH$_3$×3), 19.5 (C), 19.1 (C), 14.2 (CH$_3$); LCMS (ESI) m/z 806 (100, [M+NH$_4$]$^+$), 807 (85, [M+NH$_4$+1]$^+$), 808 (62, [M+NH$_4$+2]$^+$).

Example 51

Synthesis of 6-O-(ethoxycarbonyl)-1-C-phenyl-β-D-glucopyranoside (Va)

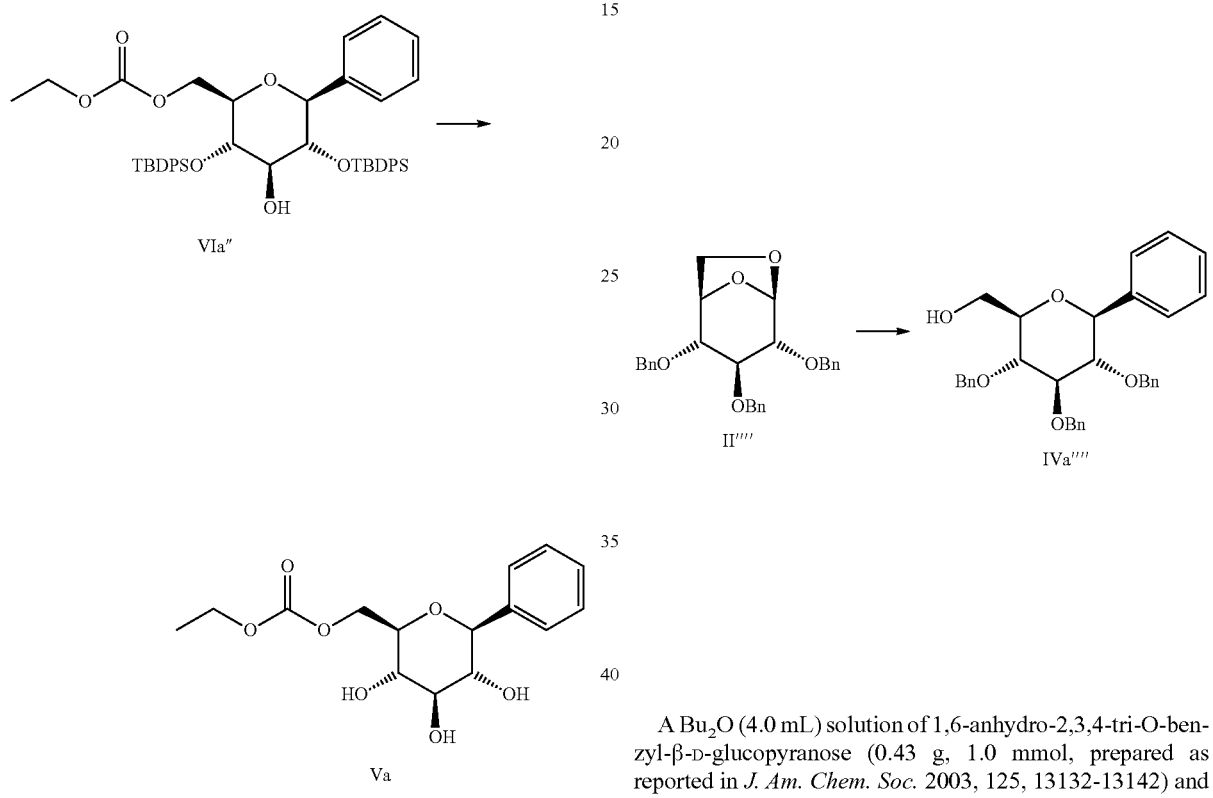

A mixture of TBAF (1.87 mL, 1.87 mmol, 1.0 M in THF) and 2,4-di-O-tert-butyldiphenylsilyl-6-O-(ethoxycarbonyl)-1-C-phenyl-β-D-glucopyranoside (492 mg, 0.62 mmol) in THF (4.2 mL) was stirred at ambient temperature for 2 hours. After the reaction was complete, CaCO$_3$ (1.2 g) was added, followed by Dowex® 50WX8-400 ion exchange resin (3.7 g) and then MeOH (8.7 mL). After stirring and then filtration, the filtrate was concentrated and the residue was purified by column chromatography (eluting with 4:1 EtOAc/n-heptane) affording 6-O-(ethoxycarbonyl)-1-C-phenyl-β-D-glucopyranoside (180 mg, 92%).

$^1$H NMR (400 MHz, CDCl$_3$) δ 7.37-7.29 (m, 5H), 4.46-4.42 (m, 2H), 4.38 (dd, J=12.0, 4.4 Hz, 1H), 4.22-4.16 (m, 2H), 4.13-4.11 (m, 2H), 3.65-3.50 (m, 3H), 3.44-3.40 (m, 1H), 3.25 (br, 1H), 1.29 (t, J=7.2 Hz, 3H); $^{13}$C NMR (100 MHz, CDCl$_3$) δ 155.6 (C), 138.1 (C), 128.49 (CH), 128.47 (CH×2), 127.5 (CH×2), 81.8 (CH), 77.73 (CH), 77.60 (CH), 75.0 (CH), 70.1 (CH), 66.9 (CH$_2$), 64.4 (CH$_2$), 14.2 (CH$_3$); LCMS (ESI) m/z 313 (100, [M+H]$^+$), 314 (20, [M+H+1]$^+$), 330 (100, [M+NH$_4$]$^+$), 331 (20, [M+NH$_4$+1]$^+$), 335 (100, [M+Na]$^+$), 336 (50, [M+Na+1]$^+$).

Example 52

Synthesis of 2,3,4-tri-O-benzyl-1-C-phenyl-β-D-glucopyranoside(((2R,3R,4R,5S,6S)-3,4,5-tris(benzyloxy)-6-phenyltetrahydro-2H-pyran-2-yl)methanol; (1S)-1-C-phenyl 2,3,4-tri-O-benzyl-glucoside; (IVa''''))

A Bu$_2$O (4.0 mL) solution of 1,6-anhydro-2,3,4-tri-O-benzyl-β-D-glucopyranose (0.43 g, 1.0 mmol, prepared as reported in J. Am. Chem. Soc. 2003, 125, 13132-13142) and Ph$_3$Al (2.2 mL, 2.2 mmol, 1.0 M in Bu$_2$O) was heated at 150° C. (external bath temperature) for 6 hours. After cooling to ambient temperature, THF (10 mL), then diatomaceous earth (1 g), then 15% aqueous NaOH (1 mL) and then Na$_2$SO$_4$ (2 g) were added sequentially to the product mixture and the resulting suspension was stirred and then filtered. The filtrate was concentrated to give a yellow oil which was purified by silica gel column chromatography (eluting with 1:20 EtOAc/n-heptane) affording the product 2,3,4-tri-O-benzyl-1-C-phenyl-β-D-glucopyranoside (0.32 g, 64%) as a white solid.

$^1$H NMR (400 MHz, CDCl$_3$) δ 7.48-7.31 (m, 15H), 7.24-7.19 (m, 3H), 6.95-6.92 (m, 2H), 5.00 (d, J=11.2 Hz, 1H), 4.95 (d, J=10.8 Hz, 1H), 4.94 (d, J=11.2 Hz, 1H), 4.74 (d, J=10.8 Hz, 1H), 4.41 (d, J=10.0 Hz, 1H), 4.31 (d, J=9.6 Hz, 1H), 3.93 (ddd, J=11.8, 6.1, 2.6 Hz, 1H), 3.87 (dd, J=9.0, 9.0 Hz, 1H), 3.81-3.70 (m, 3H), 3.59-3.53 (m, 2H), 1.97 (dd, J=6.8, 6.8, 1H, OH); $^{13}$C NMR (100 MHz, CDCl$_3$) δ 139.0 (C), 138.6 (C), 138.0 (C), 137.6 (C), 128.54 (CH×2), 128.52 (CH), 128.47 (CH×4), 128.26 (CH×2), 128.23 (CH×2), 128.1 (CH×2), 128.0 (CH), 127.744 (CH×2), 127.735 (CH), 127.69 (CH×2), 127.67 (CH), 86.6 (CH), 84.3 (CH), 81.7 (CH), 79.4 (CH), 78.3 (CH), 75.7 (CH$_2$), 75.2 (CH$_2$), 74.9 (CH$_2$), 62.4

(CH$_2$); LCMS (ESI) m/z 528 (100, [M+NH$_4$]$^+$), 529 (35, [M+NH$_4$+1]$^+$), 533 (5, [M+Na]$^+$).

Example 53

Synthesis of 2,3,4-tri-O-benzyl-1-C-phenyl-β-D-glucopyranoside(((2R,3R,4R,5S,6S)-3,4,5-tris(benzyloxy)-6-phenyltetrahydro-2H-pyran-2-yl)methanol; (1S)-1-C-phenyl 2,3,4-tri-O-benzyl-glucoside; (IVa''''))

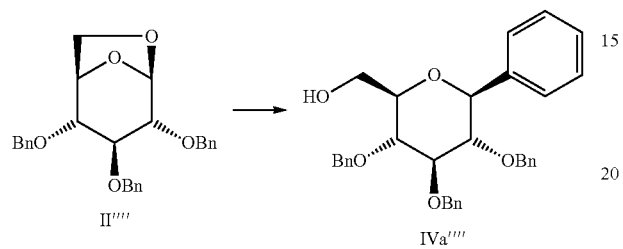

A PhOMe (4.0 mL) solution of 1,6-anhydro-2,3,4-tri-O-benzyl-β-D-glucopyranose (0.43 g, 1.0 mmol) and Ph$_3$Al (2.2 mL, 2.2 mmol, 1.0 M in Bu$_2$O) was heated at 150° C. (external bath temperature) for 6 hours. After cooling to ambient temperature, THF (10 mL), then diatomaceous earth (1 g), then 15% aqueous NaOH (1 mL) and then Na$_2$SO$_4$ (2 g) were added sequentially to the product mixture and the resulting suspension was stirred and then filtered and the filtrate was concentrated to give a yellow oil which was purified by silica gel column chromatography (eluting with 1:20 EtOAc/n-heptane) affording the product 2,3,4-tri-O-benzyl-1-C-phenyl-β-D-glucopyranoside (0.31 g, 62%) as a white solid.

Example 54

Synthesis of 2,3,4-tri-O-benzyl-1-C-phenyl-β-D-glucopyranoside(((2R,3R,4R,5S,6S)-3,4,5-tris(benzyloxy)-6-phenyltetrahydro-2H-pyran-2-yl)methanol; (1S)-1-C-phenyl 2,3,4-tri-O-benzyl-glucoside; (IVa''''))

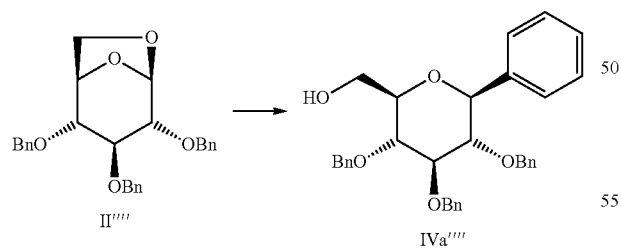

A PhMe (4 mL) solution of 1,6-anhydro-2,3,4-tri-O-benzyl-β-D-glucopyranose (0.2 g, 0.46 mmol) and Ph$_3$Al (0.9 mL, 0.90 mmol, 1.0 M in Bu$_2$O) was heated under reflux. After the starting material was consumed (as determined by TLC analysis), the reaction mixture was cooled to 0° C. and was poured over a mixture of ice and water (50 mL). The resulting mixture was extracted with EtOAc (20 mL), washed with 1 N HCl (10 mL) and then with brine (10 mL), dried over Na$_2$SO$_4$ and concentrated under reduced pressure. Column chromatography of the crude residue (eluting with 2:8 EtOAc/n-heptane) afforded 2,3,4-tri-O-benzyl-1-C-phenyl-β-D-glucopyranoside (82 mg, 35%).

Example 55

Synthesis of 1-C-phenyl-β-D-glucopyranoside((2R,3S,4R,5R,6S)-2-(hydroxymethyl)-6-phenyltetrahydro-2H-pyran-3,4,5-triol; (1S)-1-C-phenyl Glucoside; (Ia))

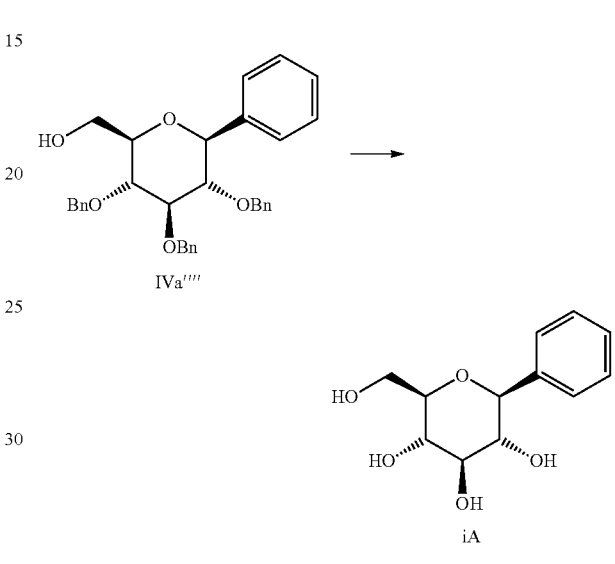

To a solution of 2,3,4-tri-O-benzyl-1-C-phenyl-β-D-glucopyranoside (40 mg, 0.08 mmol) in a mixture of MeOH (1.5 mL) and THF (1.5 mL) was added 5% Pd/C (20 mg) at ambient temperature. The reaction mixture was stirred at ambient temperature under a hydrogen gas atmosphere (about 1 atm) until the starting material was consumed (as determined by TLC analysis). The product mixture was filtered to remove the palladium residues and the filtrate was concentrated and purified by silica gel column chromatography (eluting with 1:10 MeOH/DCM) affording the product 1-C-phenyl-β-D-glucopyranoside (15 mg, 80%).

Example 56

Synthesis of 2,3,4-tri-O-tert-butyldimethylsilyl-1-C-phenyl-β-D-glucopyranoside (IVa''''')

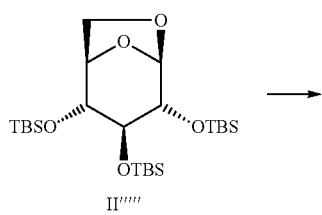

-continued

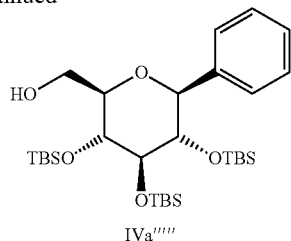

IVa'''''

To a solution of 1,6-anhydro-2,3,4-tri-O-tert-butyldimethylsilyl-β-D-glucopyranose (0.51 g, 1.0 mmol) in PhOMe (4.0 mL) at ambient temperature was added Ph$_3$Al (2.0 ml, 2.0 mmol, 1.0 M in Bu$_2$O), resulting in a light yellow-colored solution. The mixture was heated at 150° C. (external bath temperature) for 23 hours. After cooling to ambient temperature, THF (10 mL), then diatomaceous earth (1 g), then 15% aqueous NaOH (1 mL), and then Na$_2$SO$_4$ (2 g) were sequentially added to the product mixture and the resulting suspension was filtered and the filtrate was concentrated to give a yellow oil. The oil was purified by silica gel column chromatography (eluting with 1:20 EtOAc/n-heptane) to give the product 1-C-phenyl-2,3,4-tri-O-tert-butyldimethylsilyl-β-D-glucopyranoside (69 mg, 12%) as a light yellow oil.

$^1$H NMR (400 MHz, CDCl$_3$) δ 7.44-7.42 (m, 2H), 7.38-7.34 (m, 2H), 7.32-7.30 (m, 1H), 4.66 (d, J=5.6 Hz, 1H), 4.00 (dd, J=9.2, 4.4 Hz, 1H), 3.94-3.90 (m, 2H), 3.85-3.79 (m, 3H), 2.34 (dd, J=6.0, 6.0 Hz, 1H, OH), 0.98 (s, 9H), 0.94 (s, 9H), 0.88 (s, 9H), 0.16 (s, 6H), 0.15 (s, 3H), −0.03 (s, 6H), −0.27 (s, 3H); $^{13}$C NMR (100 MHz, CDCl$_3$) δ 141.5 (C), 128.1 (CH×2), 127.7 (CH), 127.6 (CH×2), 81.8 (CH), 81.3 (CH), 78.0 (CH), 77.9 (CH), 71.9 (CH), 64.4 (CH$_2$), 25.9 (CH$_3$×9), 17.96 (C), 17.95 (C), 17.87 (C), −4.1 (CH), −4.2 (CH), −4.3 (CH), −4.6 (CH), −4.9 (CH), −5.1 (CH); LCMS (ESI) m/z 583 (100, [M+H]$^+$), 584 (44, [M+H+1]$^+$), 605 (46, [M+Na]$^+$).

Example 57

Synthesis of Triphenylaluminum (Ph$_3$Al)

To a suspension of AlCl$_3$ (1.25 g, 9.4 mmol) in diisopropyl ether (20 mL) was added phenylmagnesium bromide (10.8 mL, 27 mmol, 2.5 M in Et$_2$O) at 0-5° C. The mixture was stirred at room temperature for 3-4 hours. The solvent was removed using a high-vacuum pump affording a white solid. To the solid was added PhMe (15 mL) and the mixture was stirred for 15 min, and then the resulting slurry was filtered under an atmosphere of nitrogen. The clear filtrate was evaporated to about ⅓$^{rd}$ of the original volume and the resulting solid was filtered affording 1.36 g of crude product. A slurry of the crude product and PhMe (15 mL) was stirred, and was then filtered. The filtrate was evaporated to about ⅓$^{rd}$ of the original volume and the resulting solid was filtered affording the desired product (0.56 g, 18%).

$^1$H NMR (400 MHz, CDCl$_3$) δ 7.71-7.74 (m, 6H), 7.23-7.26 (m, 9H), 4.05 (q, J=7.6 Hz, 4H), 1.14 (t, J=7.6 Hz, 6H).

Example 58

Synthesis of tri-(4-methylphenyl)aluminum (p-Tol$_3$Al)

To a solution of 4-methylphenylmagnesium bromide (9 mL, 9 mmol, 1.0 M in THF) was added a solution of AlCl$_3$ (6 mL, 3 mmol, 0.5 M in THF) at 0° C. The mixture was stirred at room temperature for 15 hours. The solution was removed from the solids by cannula and the solvent was evaporated under a strong stream of dry nitrogen gas. The residue was washed twice with n-hexane (10 mL each) and filtered in an enclosed system (Schlenk filtration) to avoid exposure of the moisture sensitive organometallic product to the atmosphere. The filtered solid was dried under reduced pressure affording the title product (0.81 g, 72%).

$^1$H NMR (400 MHz, CDCl$_3$) δ 7.70 (d, J=7.6 Hz, 6H), 7.17 (d, J=7.6 Hz, 6H), 4.01-4.11 (m, THF signals), 2.37 (s, 3H), 1.93-2.03 (m, THF signals).

Example 59

Synthesis of Ph$_3$Al and its use in an arylation reaction to provide 1-C-phenyl-β-D-glucopyranoside ((2R,3S,4R,5R,6S)-2-(hydroxymethyl)-6-phenyltetrahydro-2H-pyran-3,4,5-triol; (1S)-1-C-phenyl glucoside; (Ia))

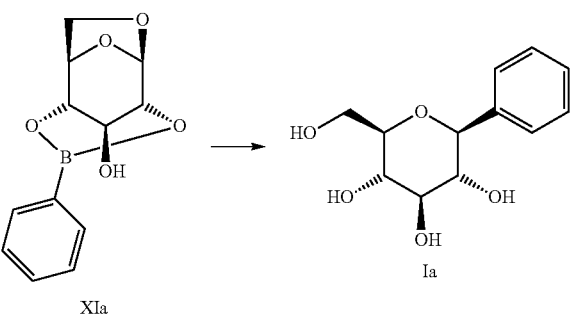

XIa → Ia

To a solution of AlCl$_3$ (133 mg; 1.0 mmol) in Bu$_2$O (4.0 mL) was added phenylmagnesium bromide (1.2 mL, 3.1 mmol, 2.6 M in Et$_2$O) at ambient temperature. After stirring at ambient temperature overnight, the product mixture was purged with a strong stream of nitrogen gas to evaporate the THF and Et$_2$O. Bu$_2$O (5.0 mL) was added to the residue and the mixture was stirred overnight, then filtered and the filtrate was purged with a strong stream of nitrogen gas to provide Ph$_3$Al as a solid.

To a solution of 1,6-anhydro-β-D-glucopyranose 2,4-O-phenylboronate (248 mg; 1.0 mmol) in PhCN (3 ml) was added Ph$_3$Al obtained above and the mixture was heated at 170° C. (external bath temperature). After heating for 4 hours, the HPLC assay analysis indicated a 65% yield of 1-C-phenyl-β-D-glucopyranoside.

What is claimed is:
1. A process for the preparation of the compound of formula IV:

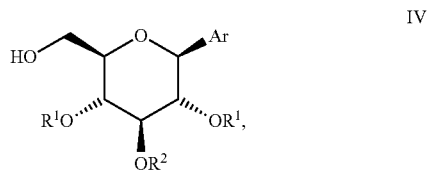

IV said process comprising contacting a compound of formula II:

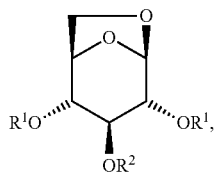

II with a metalated aryl compound under conditions sufficient to form said compound of formula IV, wherein Ar is a member selected from the group consisting of an aromatic ring, an aromatic heterocyclic ring, a biaryl ring system, a fused aromatic ring, a polyaromatic system, two or more aromatic rings bridged by a methylene group, and a meta-substituted diarylmethane system;

each $R^1$ is hydrogen or a protecting group;

$R^2$ is a member selected from the group consisting of hydrogen and a protecting group which is identical to or different from $R^1$.

2. A process in accordance with claim 1, wherein said metalated aryl compound represented by the formula $[Ar_n M^1 Y^1_p] M^2_q$, wherein Ar is a member selected from the group consisting of an aromatic ring, an aromatic heterocyclic ring, a biaryl ring system, a fused aromatic ring, a polyaromatic system, two or more aromatic rings bridged by a methylene group, and a meta-substituted diarylmethane system;

$M^1$ is selected from the group consisting of metals, metalloids, poor metals, alkaline earth metals, and lanthanides;

$Y^1$ is not present, or is one or more anions independently selected from the group consisting of halides, phenoxides, alkoxides, sulfonates, sulfates, carboxylates, carbanions, cyanide and cyanate;

$M^2$ is not present, or is one or more cations;

the subscript n is an integer or a non-integer number from 1 to 6;

the subscript p is an integer or a non-integer number from 0 to 6, and n+p is the total number of anions;

the subscript q is an integer or a non-integer number from 0 to 4, and is the total number of cations; and wherein the process is optionally carried out in the presence of metallic or non-metallic Lewis acid $M^3 Y^2_r$, wherein $M^3$ is a metal, a metalloid or a non-metal; $Y^2$ is an anion; and the subscript r is an integer of from 1 to 7.

3. A process for the preparation of the compound of formula I:

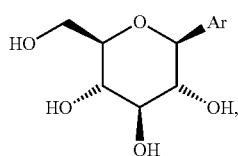

I said process comprising contacting a compound of formula III:

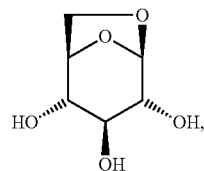

III with a metalated aryl compound of formula $[Ar_n M^1 Y^1_p] M^2_q$ under conditions sufficient to form said compound of formula I, wherein the process is optionally carried out in the presence of metallic or non-metallic Lewis acid $M^3 Y^2_r$, wherein Ar, $M^1$, $M^2$, $M^3$, $Y^1$, $Y^2$, n, p, q, and r are defined as in claim 2.

4. The process according to claim 1, wherein $R^1$ and $R^2$ are protecting groups, said process further comprising removing $R^1$ and $R^2$ groups from the compound of formula IV to provide the compound of formula I:

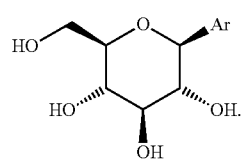

I

5. A process for the preparation of the compound of formula V comprising:

a) contacting the compound of formula IV:

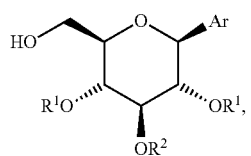

IV with $R^3 X$, and optionally $R^4 X$ when $R^2$ is H, under conditions sufficient to provide the compound of formula VI:

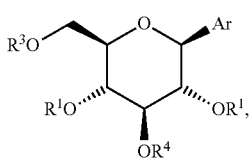

VI b) removing the $R^1$ groups and the $R^4$ group (when $R^4$ is a protecting group) from the compound of formula VI to provide the compound of formula V (wherein $R^4$ is H):

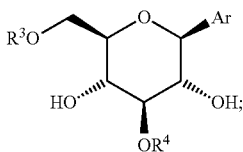

wherein $R^1$ is a protecting group;
$R^2$ is H or a protecting group that is the same or different from $R^1$;
X is a leaving group;
Ar is an aromatic ring, an aromatic heterocyclic ring, a biaryl ring system, a fused aromatic ring, a polyaromatic system, two or more aromatic rings bridged by methylene group, or a meta-substituted diarylmethane system;
$R^3$ is —COR, —$CO_2R$, —$CO_2CH_2OCOR$, —$CH_2OCOR$, —$P(O)(OR)_2$, —$P(O)(OH)O^-$, —$SO_2OR$, —$SO_3^-$, —$PO_3^{2-}$, —CONHR, —CON$(R)_2$, —$CO_2COR$, or —$CO_2CO_2R$;
$R^4$ is $R^2$, $R^3$ or H; and
R is a branched or unbranched $C_1$-$C_{20}$ alkyl, a $C_3$-$C_{20}$ cycloalkyl or a $C_3$-$C_8$ cycloalkyl$C_1$-$C_8$ alkyl.

6. The process according to claim 5, wherein the compound of formula VI is prepared by contacting a compound of formula II:

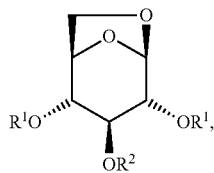

with a metalated aryl compound under conditions sufficient to form said compound of formula IV, wherein
Ar is a member selected from the group consisting of an aromatic ring, an aromatic heterocyclic ring, a biaryl ring system, a fused aromatic ring, a polyaromatic system, two or more aromatic rings bridged by a methylene group, and a meta-substituted diarylmethane system;
$R^1$ is hydrogen or a protecting group;
$R^2$ is a member selected from the group consisting of hydrogen or a protecting group which is identical or different from $R^1$.

7. The process according to claim 6, wherein the metalated aryl compound is represented by the formula $[Ar_nM^1Y^1_p]M^2_q$, wherein
Ar is a member selected from the group consisting of an aromatic ring, an aromatic heterocyclic ring, a biaryl ring system, a fused aromatic ring, a polyaromatic system, two or more aromatic rings bridged by a methylene group, and a meta-substituted diarylmethane system;
$M^1$ is selected from the group consisting of metals, metalloids, poor metals, alkali earth metals, and lanthanides;
$Y^1$ is not present or is one or more anions independently selected from the group consisting of halides, phenoxides, alkoxides, sulfonates, carboxylates, sulfates, carbanions, cyanide and cyanate $M^2$ is not present or is one or more cations;
the subscript n is an integer or a non-integer number from 1 to 6;
the subscript p is an integer or a non-integer number from 0 to 6, and n+p is the total number of anions;
the subscript q is an integer or a non-integer number from 0 to 7 and is the total number of cations; and
wherein the process is optionally carried out in the presence of metallic or non-metallic Lewis acid $M^3Y^2_r$, wherein $M^3$ is a metal, a metalloid or a non-metal; $Y^2$ is an anion; and the subscript r is an integer of from 1 to 7.

8. The process according to claim 1, further comprising wherein the process is carried out in the presence of a metallic or a non-metallic Lewis acid $M^3Y^2_r$.

9. The process according to claim 2, wherein $M^1$ is selected from metals, metalloids, and alkaline earth metals.

10. The process according to claim 2, wherein when $M^1$ is Al, the subscript n is a number from 1 to 4.

11. The process according to claim 10, with the proviso that when $R^2$ is not H or $R^2$ is H but the compound of formula II is deprotonated with a base prior to the arylation reaction, the aryl group subscript n ranges from 1.5 to 3; and $Y^1$ is not present or $Y^1$ is a halide, sulfonate, phenolate, carboxylate, alkoxide, sulfate, carbanion, cyanide or cyanate.

12. The process according to claim 11 wherein the aryl group subscript n ranges from 1.75 to 2.75 and $Y^1$ is a halide, sulfonate, or phenolate.

13. The process according to claim 10, with the proviso that when $R^2$ is H and the compound of formula II is not deprotonated prior to the arylation reaction, the aryl group subscript n ranges from 1.5 to 4; and $Y^1$ is not present or $Y^1$ is a halide.

14. The process according to claim 13 wherein the aryl group subscript n ranges from 1.75 to 3.25 and $Y^1$ is a not present or $Y^1$ is a halide, sulfonate, or phenolate.

15. The process according to claim 3, with the proviso that when $M^1$ is aluminum, the compound of formula III is reacted with a base prior to the arylation reaction and the aryl group subscript n ranges from 1.5 to 3; and $Y^1$ is not present or $Y^1$ is a halide, sulfonate, phenoxide, carboxylate, alkoxide, sulfate, carbanion, cyanide or cyanate.

16. The process according to claim 1, wherein the process is carried out in the presence of a Lewis base additive or in the presence of a Lewis base solvent selected from ethers, nitriles, and mixtures thereof.

17. The process according to claim 1, wherein the process is stereoselective.

18. The process according to claim 1, further comprising where the metalated aryl compound represented by the formula $[Ar_nM^1Y^1_p]M^2_q$ is prepared prior to the contacting with the compounds of formula II or III by mixing a triarylaluminum compound of formula $Ar_3Al$ with a trisubstituted aluminum(III) compound of formula $AlY^1_3$, where $Y^1$ is a halide, phenolate or sulfonate, in a suitable solvent.

19. The process according to claim 1, further comprising where the metalated aryl compound represented by the formula $[Ar_nM^1Y^1_p]M^2_q$ is prepared prior to the contacting with the compounds of formula II or III by mixing an aryl lithium compound of formula ArLi or aryl Grignard reagent of formula $ArMgY^1$, where $Y^1$ is a halide, with a trisubstituted aluminum(III) compound of formula $AlY^1_3$ where $Y^1$ is a halide, phenolate or sulfonate in a suitable solvent.

20. The process according to claim 19 where the lithium halide or magnesium halide salt by-products that are formed upon preparation of the metalated aryl compound represented by the formula $[Ar_nM^1Y^1_p]M^2_q$ are removed by purification of the metalated aryl compound represented by the formula $[Ar_nM^1Y^1_p]M^2_q$.

21. The process according to claim 18 where the compound of formula II, when $R^2$=H, is deprotonated with a base, prior to contacting with the metalated aryl compound represented by the formula $[Ar_nM^1Y^1_p]M^2_q$.

22. The process according to claim 21 where the base is an organolithium compound.

23. The process according to claim 21 where the base is an organolithium compound which is n-BuLi.

24. The process according to claim 1 when $R^1$ and $R^2$ are both protecting groups and a metalated aryl compound represented by the formula $[Ar_nM^1Y^1_p]M^2_q$ is a triarylaluminum compound of formula $Ar_3Al$.

25. The process according to claim 1, further comprising where the contacting with the compounds of formula II or III with a metalated aryl compound represented by the formula $[Ar_nM^1Y^1_p]M^2_q$ is conducted in a solvent selected from ethers, nitriles, halobenzenes, and mixtures thereof at a temperature above ambient temperature.

26. The process according to claim 25 where the temperature above ambient temperature is within the range of 80° C. to 180° C.

27. The process of claim 18 where $Y^1$ is a halide.

28. The process of claim 27 where the halide is chloride.

29. The process of claim 18 where the mole ratio of the triarylaluminum compound of formula $Ar_3Al$ to the trisubstituted aluminum(III) compound of formula $AlY^1_3$ is from about 1:1 to 20:1.

30. The process of claim 18 where the mole ratio of the triarylaluminum compound of formula $Ar_3Al$ to the trisubstituted aluminum(III) compound of formula $AlY^1_3$ is from about 1.5:1 to 15:1.

* * * * *